US006991935B2

(12) United States Patent
Henderson et al.

(10) Patent No.: US 6,991,935 B2

(45) **Date of Patent: *Jan. 31, 2006**

(54) TARGET CELL-SPECIFIC ADENOVIRAL VECTORS CONTAINING E3 AND METHODS OF USE THEREOF

(75) Inventors: Daniel R. Henderson, Palo Alto, CA (US); De-Chao Yu, Foster City, CA (US)

(73) Assignee: Cell Genesys, Inc., San Francisco, CA (US)

( * ) Notice: Subject to any disclaimer, the term of this patent is extended or adjusted under 35 U.S.C. 154(b) by 222 days.

This patent is subject to a terminal disclaimer.

(21) Appl. No.: 10/226,820

(22) Filed: Aug. 21, 2002

(65) Prior Publication Data

US 2003/0118555 A1 Jun. 26, 2003

Related U.S. Application Data

(63) Continuation of application No. 09/474,699, filed on Dec. 29, 1999, now Pat. No. 6,495,130.

(60) Provisional application No. 60/114,262, filed on Dec. 30, 1998.

(51) Int. Cl.

| | |
|---|---|
| *C12N 15/63* | (2006.01) |
| *C12N 15/85* | (2006.01) |
| *C12N 15/09* | (2006.01) |
| *A61K 48/00* | (2006.01) |

(52) U.S. Cl. .................. 435/320.1; 424/93.1; 424/93.2; 424/93.6; 435/235.1; 435/456; 435/325; 435/455

(58) Field of Classification Search .............. 435/320.1, 435/235.1, 455, 456, 325; 424/93.1, 93.2, 424/93.6

See application file for complete search history.

(56) References Cited

U.S. PATENT DOCUMENTS

| | | | | |
|---|---|---|---|---|
| 5,585,362 A | | 12/1996 | Wilson et al. | |
| 5,648,478 A | | 7/1997 | Henderson | |
| 5,698,443 A | | 12/1997 | Henderson et al. | |
| 5,830,686 A | | 11/1998 | Henderson | |
| 5,871,726 A | | 2/1999 | Henderson et al. | |
| 5,998,205 A | | 12/1999 | Hallenbeck et al. | |
| 6,020,191 A | * | 2/2000 | Scaria et al. | 435/320.1 |
| 6,057,299 A | | 5/2000 | Henderson | |
| 6,197,293 B1 | | 3/2001 | Henderson et al. | |
| 6,254,862 B1 | | 7/2001 | Little et al. | |
| 6,495,130 B1 | * | 12/2002 | Henderson et al. | 424/93.2 |

FOREIGN PATENT DOCUMENTS

| | | |
|---|---|---|
| CA | 2205078 | 11/1997 |
| EP | 0 808 905 A3 | 11/1997 |
| EP | 0 808 905 A2 | 11/1997 |
| WO | WO 95/11984 A3 | 5/1995 |
| WO | WO 95/11984 A2 | 5/1995 |
| WO | WO 95/14100 A2 | 5/1995 |
| WO | WO 95/14100 A3 | 5/1995 |
| WO | WO 95/19434 A1 | 7/1995 |
| WO | WO 96/17053 A1 | 6/1996 |
| WO | WO 96/34969 A1 | 11/1996 |
| WO | WO 97/01358 A1 | 1/1997 |
| WO | WO 98/04132 A1 | 2/1998 |
| WO | WO 98/05797 A1 | 2/1998 |
| WO | WO 98/37189 A1 | 8/1998 |
| WO | WO 98/39464 A3 | 9/1998 |
| WO | WO 98/39464 A2 | 9/1998 |
| WO | WO 98/39465 A3 | 9/1998 |
| WO | WO 98/39465 A2 | 9/1998 |
| WO | WO 98/39466 A3 | 9/1998 |
| WO | WO 98/39466 A2 | 9/1998 |
| WO | WO 98/39467 A2 | 9/1998 |
| WO | WO 98/39467 A3 | 9/1998 |
| WO | WO 99/06576 A1 | 2/1999 |
| WO | WO 99/25860 A1 | 5/1999 |
| WO | WO 00/15820 A1 | 3/2000 |
| WO | WO 00/20041 A1 | 4/2000 |

OTHER PUBLICATIONS

Ilan et al, PNAS 1997;94:2587–92.*

Abe, M. and Kufe, D. (1990) "Transcriptional regulation of DF3 gene expression in human MCF–7 breast carcinoma" *J. Cell. Physiol.* 143:226–231.

Abe, M. and Kufe, D. (1993) "Characterization of cis–acting elements regulating transcription of the human DF3 breast carcinoma–associated antigen (MUC1) gene" *Proc. Natl. Acad. Sci. USA* 90:282–286.

Amberg et al. (1997) "Fiber genes of adenoviruses with tropism for the eye and the genital tract" *Virology* 227:239–244.

Ausubel et al., Eds. (1987) in: Current Protocols in Molecular Biology, Suppl. 30, Section 7.7.18, Table 7.7.1.

Bailey et al. (1993) "Enteric adenovirus type 40: expression of E1B proteins in vitro and in vivo" *Virology* 193:631–641.

Bailey et al. (1994) "Cell type specific regulation of expression from the Ad40 E1b promoter in recombinant Ad5/Ad40 viruses" *Virology* 202:695–706.

(Continued)

*Primary Examiner*—Q. Janice Li

(74) *Attorney, Agent, or Firm*—DLA Piper Rudnick Gray Cary US LLP

(57) ABSTRACT

The invention provides adenoviral vectors (preferably replication competent) comprising both an E3 sequence and at least one adenoviral gene under transcriptional control of a target cell-specific transcriptional response element. These vectors display significantly improved cytotoxicity, which is especially useful in the cancer context, in which selective destruction of target cells is desirable. The invention further provides host cells comprising the vectors. The invention further provides methods of using the adenoviral vectors.

19 Claims, 57 Drawing Sheets

OTHER PUBLICATIONS

Behringer et al. (1988) "Dwarf mice produced by genetic ablation of growth hormone–expressing cells" *Genes Dev.* 2:453–461.

Bischoff et al. (1996) "An adenovirus mutant that replicates selectively in p53–deficient human tumor cells" *Science* 274:373–376.

Bridge et al. (1989) "Redundant control of adenovirus late gene expression by early region 4" *J. Virol.* 63(2):631–638.

Bunn et al. (1996) "Oxygen sensing and molecular adaptation to hypoxia" *Physiol. Rev.* 76(3):839–885.

Bursch et al. (1990) "Determination of the length of the histological stages of apoptosis in normal liver and in altered hepatic foot of rats" *Carcinogenesis* 11(5):847–853.

Bursch et al. (1992) "Cell death by apoptosis and it protective role against disease" *Trends Pharm. Sci.* 13:245–251.

Cannio et al. (1991) "A cell–type specific and enhancer–dependent silencer in the regulation of the expression of the human urokinase plasminogen activator gene" *Nucl. Acids Res.* 19:2303–2308.

Chengalvata et al. (1997) "Replication and immunogenicity of Ad7–, Ad4–, and Ad5–hepatitis B virus surface antigen recombinants, with or without a portion of E3 region, in chimpanzees" *Vaccine* 15:335–339.

Dachs et al. (1997) "Targeting gene expression to hypoxic tumor cells" *Nat. Med.* 3:515–520.

Dachs, G. and Stratford, I. (1996) "The molecular response of mammalian cells to hypoxia and the potential for exploitation in cancer therapy" *Br. J. Cancer Suppl.* 74:S126–S132.

Dai, J. and Burnstein, K. (1996) "Two androgen response elements in the androgen receptor coding region are required for cell–specific up–regulation of receptor messenger RNA" *Mol. Endocrinol.* 10:1582–1594.

Dodd et al. (1983) "Characterization and cloning of rat dorsal prostate mRNAs. Androgen regulation of rwo closely related abundant mRNAs" *J. Biol. Chem.* 258:10731–10737.

Elsing et al. (1998) "The adenovirus E3/10.4K–14.5K proteins down–modulate the apoptosis receptor Fas/Apo–1 by inducing its internalization" *Proc. Natl. Acad. Sci. USA* 95:10072–10077.

Firth et al. (1994) "Oxygen–regulated control elements in the phosphoglycerate kinase 1 and lactate dehydrogenase A genes: similarities with the erythropoietin 3' enhancer" *Proc. Natl. Acad. Sci. USA* 91:6496–6500.

Flint, S.J. (1982) "Expression of adenoviral genetic information in productively infected cells" *Biochem. Biophys. Acta* 651:175–208.

Flint, S.J. (1986) "Regulation of adenovirus mRNA formation" *Adv. Virus Res.* 31:169–228.

Folkman, J. (1990) "What is the evidence that tumors are angiogenesis dependent?" *J. Natl. Can. Inst.* 82:4–6.

Foster et al. (1997) "Characterization of prostatic epithelial cell lines derived from transgenic adenocarcinoma of the mouse prostate (TRAMP) model" *Cancer Res.* 57:3325–3330.

Frankel et al. (1989) "Selection and Characterization of ricin toxin A–chain mutations in *Saccharomyces cerevisiae" Mol. Cell. Biol.* 9:415–420.

Ginsberg, H.S. (1996) "The ups and downs of adenovirus vectors" *Bull. NY Acad. Med. Summer* 73(1):53–58.

Girling et al. (1989) "A core protein epitope of the polymorphic epithelial mucin detected by the monoclonal antibody SM–3 is selectively exposed in a range of primary carcinomas" *Int. J. Cancer* 43:1072–1076.

Grand, R.J. (1987) "The structure and functions of the adenovirus early region 1 proteins" *Biochem. J.* 241:25–38.

Greenberg et al. (1994) "The rat probasin gene promoter directs hormonally and developmentally regulated expression of a heterologous gene specifically to the prostate in transgenic mice" *Mol. Endocrinol.* 8:230–239.

Greenberg et al. (1995) "Prostate cancer in a transgenic mouse" *Proc. Natl. Acad. Sci. USA* 92:3439–3443.

Grooteclaes et al. (1994) "The 6–kilobase c–erbB2 promoter contains positive and negative regulatory elements functional in human mammary cell lines" *Cancer Res.* 54:4193–4199.

Guillemin, K and Krasnow, M. (1997) "The hypoxic response: huffing and HIFing" *Cell* 89:9–12.

Hallahan et al. (1995) "Spatial and temporal control of gene therapy using ionizing radiation" *Nat. Med.* 1:786–791.

Hilkens, J. (1988) "Biochemistry and function of mucins in malignant disease" *Cancer Rev.* 11–12:25–54.

Horwitz et al. (1995) "Model systems for studying the effects of adenovirus E3 genes on virulence in vivo" *Curr. Topics Microbiol. Immunol.* 199(Pt 1):195–211.

Hudson et al. (1990) "Studies and inducible regulation of the human c–erb B2/neu promoter" *J. Biol. Chem.* 265:4389–4393.

Ido et al. (1995) "Gene therapy for hepatoma cells using a retrovirus vector carrying herpes simplex virus thymidine kinase gene under the control of human alpha–fetoprotein gene promoter" *Cancer Res.* 55:3105–3109.

Ilan et al. (1997) "Insertion of the adenoviral E3 region into a recombinant viral vector prevents antiviral humoral and cellular immune responses and permits long–term gene expression" *Proc. Natl. Acad. Sci. USA* 94:2587–2592.

Ishii et al. (1987) "Characterization of the promoter region of the human c–erbB–2 protooncogene" *Proc. Natl. Acad. Sci. USA* 84:4374–4378.

Jiang et al. (1997) "V–SRC induces expression of hypoxia–inducible factor 1 (HIF–1) and transcription of genes encoding vascular endothelial growth factor and enolase 1: Involvement of HIF–1 in tumor progression" *Cancer Res.* 57:5328–5335.

Johnson et al. (1994) "Autoregulatory control of E2F1 expression in response to positive and negative regulators of cell cycle progression" *Genes Dev.* 8:1514–1525.

Jones, N. and Shenk, T. (1979) "Isolation of adenovirus type 5 host range deletion mutants defective for transformation of rat embryo cells" *Cell* 17:683–689.

Kallinowski, F. (1996) "The role of tumor hypoxia for the development of future treatment concepts for locally advanced cancer" *Cancer J.* 9:37–40.

Katsuragi et al. (1989) "A case of gall bladder cancer with high level alpha–fetoprotein" *Rinsho Hoshasen* 34:371–374, English Abstract.

Kawamoto et al. (1992) "Alpha–fetoprotein–producing pancreatic cancer—a case report and review of 28 cases" *Hepatogastroenterol.* 39:282–286.

Kovarik et al. (1993) "Analysis of the tissue–specific promoter of the MUC1 gene" *J. Biol. Chem.* 268:9917–9926.

Kovarik et al. (1996) "Two GC boxes (Sp1 sites) are involved in regulation of the activity of the epithelium–specific MUC1 promoter" *J. Biol. Chem.* 271:18140–18147.

Koyama et al. (1996) "Biochemical characterization of α–fetoprotein and other serum proteins produced by a uterine endometrial adenocarcinoma" *Jpn. J. Cancer Res.* 87:612–617.

Kufe et al. (1984) "Differential reactivity of a novel monoclonal antibody (DF3) with human malignant versus benign breast tumors" *Hybridoma* 3:223–232.

Lamb et al. (1985) "Nucleotide sequence of cloned cDNA coding for preproricin" *Eur. J. Biochem.* 148:265–270.

Lee et al. (1995) "The constitutive expression of the immunomodulatory gp19K protein in E1–, E3–adenoviral vectors strongly reduces the host cytotoxic T cell response against the vector" *Gene Ther.* 2:256–262.

Lundwall et al. (1987) "Molecular cloning of human prostate specific antigen cDNA" *FEBS Lett.* 214:317–322.

Lundwall, A. (1989) "Characterization of the gene for prostate–specific antigen, a human glandular kallikrein" *Biochem. Biophys. Res. Commun.* 161:1151–1159.

Lundy et al. (1985) "Monoclonal antibody DF3 correlates with tumor differentiation and hormone receptor status in breast cancer patients" *Breast Can. Res. Treat.* 5:269–276.

Matusik et al. (1986) "Regulation of prostatic genes: role of androgens and zinc in gene expression" *Biochem. Cell. Biol.* 64:601–607.

Maxwell et al. (1987) "Cloning, sequence determination, and expression in transfected cells of the coding sequence for the tox 176 attenuated diphtheria toxin A chain" *Mol. Cell. Biol.* 7:1576–1579.

McKinnon et al. (1982) "Tn5 mutagenesis of the transforming genes of human adenovirus type 5" *Gene* 19:33–42.

Messing et al. (1992) "$P_0$ promoter directs expression of reporter and toxin genes to Schwann cells of transgenic mice" *Neuron* 8:507–520.

Miller et al. (May 1997) "Progress in transcriptionally targeted and regulatable vectors for genetic therapy" *Hum. Gene Ther.* 8:803–815.

Morris, B.J. (1989) "hGK–1: a kallikrein gene expressed in human prostate" *Clin. Exp. Pharm. Physiol.* 16:345–351.

Murtha et al. (1993) "Androgen induction of a human prostate–specific kallikrein, hKLK2: characterization of an androgen response element in the 5' promoter region of the gene" *Biochem.* 32:6459–6464.

Nettelback et al. (Apr. 2000) "Gene therapy designer promoters for tumour targeting" *TIG* 16(4):174–181.

Nevins, J.R. (1989) "Mechanisms of viral–mediated trans–activation of transcription" *Adv. Virus Res.* 37:35–83.

Palmiter et al. (1987) "Cell lineage ablation in transgenic mice by cell–specific expression of a toxin gene" *Cell* 50:435–443.

Perisic et al. (1989) "Stable binding of Drosophila heat shock factor to head–to–head and tail–to–tail repeats of a conserved 5 bp recognition unit" *Cell* 59:797–806.

Piatak et al. (1988) "Expression of soluble and fully functional ricin A chain in *Escherichia coli* is temperature–sensitive" *J. Biol. Chem.* 263:4837–4843.

Poller et al. (1996) "Stabilization of transgene expression by incorporation of E3 region genes into an adenoviral factor IX vector and by transient anti–CD4 treatment of the host" *Gene Ther.* 3:521–530.

Qiu et al. (1990) "In situ hybridization of prostate–specific antigen mRNA in human prostate" *J. Urol.* 144:1550–1556.

Rennie et al. (1993) "Characterization of two cis–acting DNA elements involved in the androgen regulation of the probasin gene" *Mol. Endocrinol.* 7:23–36.

Riccio et al. (1985) "The human urokinase–plasminogen activator gene and its promoter" *Nucl. Acids Res.* 13:2759–2771.

Riegman et al. (1991) "The promoter of the prostate–specific antigen gene contains a functional androgen responsive element" *Mol. Endocrinol.* 5:1921–1930.

Rodriguez et al. (1997) "Prostate attenuated replication competent adenovirus (ARCA) CN706: a selective cytotoxic for prostate–specific antigen–positive prostate cancer cells" *Cancer Res.* 57:2559–2563.

Sambrook et al., Eds. (1989) in: Molecular Cloning, A Laboratory Manual, $2^{nd}$ Ed., Cold Spring Harbor Laboratory Press, Cold Spring Harbor, NY, p. 7.52.

Schedlich et al. (1987) "Primary structure of a human glandular kallikrein gene" *DNA* 6:429–437.

Schowalter et al. (1997) "Heterologous expression of adenovirus E3–gp19K in an E1a–deleted adenovirus vector inhibits MHC I expression in vitro, but does not prolong transgene expression in vivo" *Gene Ther.* 4:351–360.

Schrewe et al. (1990) "Cloning of the complete gene for carcinoembryonic antigen: analysis of its promoter indicates a region conveying cell type–specific expression" *Mol. Cell. Biol.* 10:2738–2748.

Schuur et al. (1996) "Prostate–specific antigen expression is regulated by an upstream enhancer" *J. Biol. Chem.* 271:7043–7051.

Scott et al. (1994) "Binding of an ETS–related protein within the DNase I hypersensitive site of the HER2/neu promoter in human breast cancer cells" *J. Biol. Chem.* 269:19848–19858.

Shisler et al. (1997) "The adenovirus E3–10.4K/14.5K complex mediates loss of cell surface Fas (CD95) and resistance to Fas–induced apoptosis" *J. Virol.* 71:8299–8306.

Swaminathan, S and Thimmapaya, B. (1995) "Regulation of adenovirus E2 transcription unit" *Curr Top Microbiol Immunol.* 199(Pt 3):177–194.

Sweetland et al. (1988) "Post–castration rebound of an androgen regulated prostatic gene" *Mol. Cell. Biochem.* 84:3–15.

Tal et al. (1987) "Human HER2 (neu) promoter: evidence for multiple mechanisms for transcriptional initiation" *Mol. Cell. Biol.* 7:2597–2601.

Taylor–Papadimitriou et al. (1990) "Mucin antigens: molecular structure and potential use in immunotherapy" *J. Nucl. Med. Allied Sci.* 34:144–150.

Tollefson et al. (1996) "The E3–11.6–kDa adenovirus death protein (ADP) is required for efficient cell death: characterization of cells infected with adp mutants" *Virology* 220:152–162.

Tsai–Morris et al. (1988) "5' flanking sequence and genomic structure of Egr–1, a murine mitogen inducible zinc finger encoding gene" *Nucl. Acids Res.* 16:8835–8846.

Verma et al. (1997) "Gene therapy—promises, problems and prospects" *Nature* 389:239–242.

Virtanen et al. (1984) "mRNAs from human adenovirus 2 early region 4" *J. Virol.* 51:822–831.

Von Herrath et al. (1997) "Expression of adenoviral E3 transgenes in beta cells prevents autoimmune diabetes" *Proc. Natl. Acad. Sci. USA* 94:9808–9813.

Wadsworth et al. (1997) "Adenovirus vector–infected cells can escape adenovirus antigen–specific cytotoxic T–lymphocyte killing in vivo" *J. Virol.* 71:5189–5196.

Watanabe et al. (1987) "Cell–specific enhancer activity in a far upstream region of the human α–fetoprotein gene" *J. Biol. Chem.* 262:4812–4818.

Weinberg, D. and Katner, G. (1983) *Proc. Natl. Acad. Sci. USA* 80:5383–5386.

Welch, W.J. (1990) "The mammalian stress response: cell physiology and biochemistry of stress proteins" in: Stress Proteins in Biology and Medicine, Morimoto et al., Eds., Cold Spring Harbor Laboratory Press, Cold Spring Harbor, NY, pp. 223–278.

Wold et al. (1991) "Region E3 of adenovirus: a cassette of genes involved in host immunosurveillance and virus–cell interactions" *Virology* 184:1–8.

Wold et al. (1995) "E3 transcription unit of adenovirus" *Curr. Top. Microbiol. Immunol.* 199(Pt 1):237–274.

Wolf et al. (1992) "Transcriptional regulation of prostate kallikrein–like genes by androgen" *Mol. Endocrinol.* 6:753–762.

Young et al. (1992) "Tissue–specific and hormonal regulation of human prostate–specific glandular kallikrein" *Biochem.* 31:818–824.

Yu et al. (1999) "The addition of adenovirus type 5 region E3 enables calydon virus 787 to eliminate distant prostate tumor xenografts" *Cancer Res.* 59:4200–4203.

Zhang et al. (1997) "Identification of two novel cis–elements in the promoter of the prostate–specific antigen gene that are required to enhance androgen receptor–mediated transactivation" *Nucl. Acids Res.* 25:3143–3150.

Zotter et al. (1988) "Tissue and tumor distribution of human polymorphic epithelial mucin" *Cancer Rev.* 11–12:55–101.

* cited by examiner

Region E3 of Adenovirus ccccgaggca gtgcatgagg ctcagggcgt gcgtgagtcg cagcgagacc ccggggtgca ggccgga

```
gggcccaaaa ttagcaagtg accacgtggt tctgaagcca gtggcctaag gaccaccctt      60
gcagaaccgt ggtctccttg tcacagtcta ggcagcctct ggcttagcct ctgtttcttt     120
cataaccttt ctcagcgcct gctctgggcc agaccagtgt tgggaggagt cgctactgag     180
ctcctagatt ggcaggggag gcagatggag aaaaggagtg tgtgtggtca gcattggagc     240
agaggcagca gtgggcaata gaggaagtga gtaaatcctt gggagggctc cctagaagtg     300
atgtgttttc tttttttgtt ttagagacag gatctcgctc tgtcgcccag gctggtgtgc     360
agtggcatga tcatagctca ctgcagcctc gacttctcgg gctcaagcaa tcctcccacc     420
tcagcctccc aagtagctgg gactacgggc acacgccacc atgcctggct aatttttgta     480
tttttgtag agatgggtct tcaccatgtt gatcaggctg gtctcgaact cctgggctca      540
tgcgatccac cccgccagct gattacaggg attccggtgg tgagccaccg cgcccagacg     600
ccacttcatc gtattgtaaa cgtctgttac ctttctgttc ccctgtctac tggactgtga     660
gctccttagg gccacgaatt gaggatgggg cacagagcaa gctctccaaa cgtttgttga     720
atgagtgagg gaatgaatga gttcaagcag atgctatacg ttggctgttg gagattttgg     780
ctaaaatggg acttgcagga aagcccgacg tccccctcgc catttccagg caccgctctt     840
cagcttgggc tctgggtgag cgggataggg ctgggtgcag gattaggata atgtcatggg     900
tgaggcaagt tgaggatgga agaggtggct gatggctggg ctgtggaact gatgatcctg     960
aaaagaagag gggacagtct ctggaaatct aagctgaggc tgttgggggc tacaggttga    1020
gggtcacgtg cagaagagag gctctgttct gaacctgcac tatagaaagg tcagtgggat    1080
gcgggagcgt cggggcgggg cggggcctat gttcccgtgt ccccacgcct ccagcagggg    1140
acgcccgggc tgggggcggg gagtcagacc gcgcctggta ccatccggac aaagcctgcg    1200
cgcgccccgc cccgccattg gccgtaccgc cccgcgccgc cgccccatcc cgcccctcgc    1260
cgccgggtcc ggcgcgttaa agccaatagg aaccgccgcc gttgttcccg tcacggacgg    1320
ggcagccaat tgtggcggcg ctcggcggct cgtggctctt tcgcggcaaa aaggatttgg    1380
cgcgtaaaag tggccgggac tttgcaggca gcggcggccg gggcggagc gggatcgagc     1440
cctcgccgag gcctgccgcc atgggcccgc gccgccgccg ccgcctgtca cccgggccgc    1500
gcgggccgtg agcgtcatg                                                 1519
```

FIG. 22*i*

```
aagcttctag ttttcttttc ccggtgacat cgtggaaagc actagcatct ctaagcaatg     60
atctgtgaca atattcacag tgtaatgcca tccagggaac tcaactgagc cttgatgtcc    120
agagattttt gtgttttttt ctgagactga gtctcgctct gtgccaggct ggagtgcagt    180
ggtgcaacct tggctcactg caagctccgc ctcctgggtt cacgccattc tcctgcctca    240
gcctcctgag tagctgggac tacaggcacc cgccaccacg cctggctaat tttttgtat     300
ttttagtaga gatggggttt cactgtgtta gccaggatgg tctcagtctc ctgacctcgt    360
gatctgccca ccttggcctc ccaaagtgct gggatgacag gcgtgagcca ccgcgcctgg    420
ccgatatcca gagatttttt gggggctcc atcacacaga catgttgact gtcttcatgg     480
ttgactttta gtatccagcc cctctagaaa tctagctgat atagtgtggc tcaaaacctt    540
cagcacaaat cacaccgtta gactatctgg tgtggcccaa accttcaggt gaacaaaggg    600
actctaatct ggcaggatat tccaaagcat tagagatgac ctcttgcaaa gaaaaagaaa    660
tggaaaagaa aaagaaagaa aggaaaaaaa aaaaaaaaaa gagatgacct ctcaggctct    720
gaggggaaac gcctgaggtc tttgagcaag gtcagtcctc tgttgcacag tctccctcac    780
agggtcattg tgacgatcaa atgtggtcac gtgtatgagg caccagcaca tgcctggctc    840
tggggagtgc cgtgtaagtg tatgcttgca ctgctgaatg cttgggatgt gtcagggatt    900
atcttcagca cttacagatg ctcatctcat cctcacagca tcactatggg atgggtatta    960
ctggcctcat ttgatggaga aagtggctgt ggctcagaaa gggggacca ctagaccagg    1020
gacactctgg atgctgggga ctccagagac catgaccact caccaactgc agagaaatta   1080
attgtggcct gatgtccctg tcctggagag ggtggaggtg gaccttcact aacctcctac   1140
cttgaccctc tcttttaggg ctctttctga cctccaccat ggtactagga ccccattgta   1200
ttctgtaccc tcttgactct atgaccccca ctgcccactg catccagctg ggtcccctcc   1260
tatctctatt cccagctggc cagtgcagtc tcagtgccca cctgtttgtc agtaactctg   1320
aaggggctga cattttactg acttgcaaac aaataagcta actttccaga gttttgtgaa   1380
tgctggcaga gtccatgaga ctcctgagtc agaggcaaag gcttttactg ctcacagctt   1440
agcagacagc atgaggttca tgttcacatt agtacacctt gcccccccca aatcttgtag   1500
ggtgaccaga gcagtctagg tggatgctgt gcagaagggg tttgtgccac tggtgagaaa   1560
cctgagatta ggaatcctca atcttatact gggacaactt gcaaacctgc tcagcctttg   1620
tctctgatga agatattatc ttcatgatct tggattgaaa acagacctac tctggaggaa   1680
```

FIG. 22*ii*

```
catattgtat cgattgtcct tgacagtaaa caaatctgtt gtaagagaca ttatctttat    1740
tatctaggac agtaagcaag cctggatctg agagagatat catcttgcaa ggatgcctgc    1800
tttacaaaca tccttgaaac aacaatccag aaaaaaaaag gtgttgctgt ctttgctcag    1860
aagacacaca gatacgtgac agaaccatgg agaattgcct cccaacgctg ttcagccaga    1920
gccttccacc cttgtctgca ggacagtctc aacgttccac cattaaatac ttcttctatc    1980
acatcctgct tctttatgcc taaccaaggt tctaggtccc gatcgactgt gtctggcagc    2040
actccactgc caaacccaga ataaggcagc gctcaggatc ccgaaggggc atggctgggg    2100
atcagaactt ctgggtttga gtgaggagtg ggtccaccct cttgaatttc aaaggaggaa    2160
gaggctggat gtgaaggtac tgggggaggg aaagtgtcag ttccgaactc ttaggtcaat    2220
gagggaggag actggtaagg tcccagctcc cgaggtactg atgtgggaat ggcctaagaa    2280
tctcatatcc tcaggaagaa ggtgctggaa ttctgagggg tagagttctg ggtatatttg    2340
tggcttaagg ctctttggcc cctgaaggca gaggctggaa ccattaggtc cagggtttgg    2400
ggtgatagta atgggatctc ttgattcctc aagagtctga ggatcgaggg ttgcccattc    2460
ttccatcttg ccacctaatc cttactccac ttgagggtat caccagccct tctagctcca    2520
tgaaggtccc ctgggcaagc acaatctgag catgaaagat gccccagagg ccttgggtgt    2580
catccactca tcatccagca tcacactctg agggtgtggc cagcaccatg acgtcatgtt    2640
gctgtgacta tccctgcacc gtgcctctcc agccacctgc caaccgtaga gctgcccatc    2700
ctcctctggt gggagtggcc tgcatggtgc caggctgagg cctagtgtca gacagggagc    2760
ctggaatcat agggatccag gactcaaaag tgctagagaa tggccatatg tcaccatcca    2820
tgaaatctca aaggcttctg ggtggagggc acagggacct gaacttatgg tttcccaagt    2880
ctattgctct cccaagtgag tctcccagat acgaggcact gtgccagcat cagccttatc    2940
tccaccacat cttgtaaaag gactacccag ggccctgatg aacaccatgg tgtgtacagg    3000
agtagggggt ggaggcacgg actcctgtga ggtcacagcc aagggagcat catcatgggt    3060
ggggaggagg caatggacag gcttgagaac ggggatgtgg ttgtatttgg ttttctttgg    3120
ttagataaag tactgggtat aggattgaga gtggagtatg aagaccagtt aggatggagg    3180
atcagattgg agttgggtta gataaagtgc tgggtatagg attgagagtg gagtatgaag    3240
accagttagg atagaggatc agattggagt tgggttagag atggggtaaa attgtgctcc    3300
ggatgagttt gggattgaca ctgtggaggt ggtttgggat ggcatggctt tgggatggaa    3360
```

FIG. 22iii

```
atagatttgt tttgatgttg gctcagacat ccttggggar tgaactgggg atgaagctgg 3420
gtttgatttt ggaggtagaa gacgtggaag tagctgtcag atttgacagt ggccatgagt 3480
tttgtttgat ggggaatcaa acaatggggg aagacataag ggttggcttg ttaggttaag 3540
ttgcgttggg ttgatggggt cggggctgtg tataatgcag ttggattggt ttgtattaaa 3600
ttgggttggg tcaggttttg gttgaggatg agttgaggat atgcttgggg acaccggatc 3660
catgaggttc tcactggagt ggagacaaac ttcctttcca ggatgaatcc agggaagcct 3720
taattcacgt gtaggggagg tcaggccact ggctaagtat atccttccac tccagctcta 3780
agatggtctt aaattgtgat tatctatatc cacttctgtc tccctcactg tgcttggagt 3840
ttacctgatc actcaactag aaacagggga agattttatc aaattctttt tttttttttt 3900
tttttttga gacagagtct cactctgttg cccaggctgg agtgcagtgg cgcagtctcg 3960
gctcactgca acctctgcct cccaggttca agtgattctc ctgcctcagc ctcctgagtt 4020
gctgggatta caggcatgca gcaccatgcc cagctaattt ttgtattttt agtagagatg 4080
gggtttcacc aatgtttgcc aggctggcct cgaactcctg acctggtgat ccacctgcct 4140
cagcctccca aagtgctggg attacaggcg tcagccaccg cgcccagcca cttttgtcaa 4200
attcttgaga cacagctcgg gctggatcaa gtgagctact ctggttttat tgaacagctg 4260
aaataaccaa ctttttggaa attgatgaaa tcttacggag ttaacagtgg aggtaccagg 4320
gctcttaaga gttcccgatt ctcttctgag actacaaatt gtgattttgc atgccacctt 4380
aatctttttt tttttttttt taaatcgagg tttcagtctc attctatttc ccaggctgga 4440
gttcaatagc gtgatcacag ctcactgtag ccttgaactc ctggccttaa gagattctcc 4500
tgcttcggtc tcccaatagc taagactaca gtagtccacc accatatcca gataattttt 4560
aaatttttg gggggccggg cacagtggct cacgcctgta atcccaacac catgggaggc 4620
tgagatgggt ggatcacgag gtcaggagtt tgagaccagc ctgaccaaca tggtgaaact 4680
ctgtctctac taaaaaaaaa aaaaatagaa aaattagccg ggcgtggtgg cacacggcac 4740
ctgtaatccc agctactgag gaggctgagg caggagaatc acttgaaccc agaaggcaga 4800
ggttgcaatg agccgagatt gcgccactgc actccagcct gggtgacaga gtgagactct 4860
gtctcaaaaa aaaaaaattt tttttttttt tttgtagaga tggatcttgc tttgtttctc 4920
tggttggcct tgaactcctg gcttcaagtg atcctcctac cttggcctcg gaaagtgttg 4980
ggattacagg cgtgagccac catgactgac ctgtcgttaa tcttgaggta cataaacctg 5040
gctcctaaag gctaaaggct aaatatttgt tggagaaggg gcattggatt ttgcatgagg 5100
```

FIG. 22iv

```
atgattctga cctgggaggg caggtcagca ggcatctctg ttgcacagat agagtgtaca   5160
ggtctggaga acaaggagtg gggggttatt ggaattccac attgtttgct gcacgttgga   5220
ttttgaaatg ctagggaact ttgggagact catatttctg ggctagagga tctgtggacc   5280
acaagatctt tttatgatga cagtagcaat gtatctgtgg agctggattc tgggttggga   5340
gtgcaaggaa aagaatgtac taaatgccaa gacatctatt tcaggagcat gaggaataaa   5400
agttctagtt tctggtctca gagtggtgca gggatcaggg agtctcacaa tctcctgagt   5460
gctggtctct tagggcacac tgggtcttgg agtgcaaagg atctaggcac gtgaggcttt   5520
gtatgaagaa tcggggatcg tacccacccc ctgtttctgt ttcatcctgg gcatgtctcc   5580
tctgcctttg tcccctagat gaagtctcca tgagctacaa gggcctggtg catccagggt   5640
gatctagtaa ttgcagaaca gcaagtgcta gctctccctc cccttccaca gctctgggtg   5700
tgggaggggg ttgtccagcc tccagcagca tggggagggc cttggtcagc ctctgggtgc   5760
cagcagggca ggggcggagt cctggggaat gaaggtttta tagggctcct gggggaggct   5820
ccccagcccc aagctt                                                   5836
```

FIG. 23*i*

```
aagcttttta gtgctttaga cagtgagctg gtctgtctaa cccaagtgac ctgggctcca      60
tactcagccc cagaagtgaa gggtgaagct gggtggagcc aaaccaggca agcctaccct     120
cagggctccc agtggcctga gaaccattgg acccaggacc cattacttct agggtaagga     180
aggtacaaac accagatcca accatggtct gggggacag ctgtcaaatg cctaaaaata      240
tacctgggag aggagcaggc aaactatcac tgccccaggt tctctgaaca gaaacagagg     300
ggcaacccaa agtccaaatc caggtgagca ggtgcaccaa atgcccagag atatgacgag     360
gcaagaagtg aaggaaccac ccctgcatca aatgttttgc atgggaagga gaagggggtt     420
gctcatgttc ccaatccagg agaatgcatt tgggatctgc cttcttctca ctccttggtt     480
agcaagacta agcaaccagg actctggatt tggggaaaga cgtttatttg tggaggccag     540
tgatgacaat cccacgaggg cctaggtgaa gagggcagga aggctcgaga cactggggac     600
tgagtgaaaa ccacacccat gatctgcacc acccatggat gctccttcat tgctcacctt     660
tctgttgata tcagatggcc ccattttctg taccttcaca gaaggacaca ggctagggtc     720
tgtgcatggc cttcatcccc ggggccatgt gaggacagca ggtgggaaag atcatgggtc     780
ctcctgggtc ctgcagggcc agaacattca tcacccatac tgacctccta gatgggaatg     840
gcttccctgg ggctgggcca acggggcctg ggcaggggag aaaggacgtc aggggacagg     900
gaggaagggt catcgagacc cagcctggaa ggttcttgtc tctgaccatc caggatttac     960
ttccctgcat ctacctttgg tcattttccc tcagcaatga ccagctctgc ttcctgatct    1020
cagcctccca ccctggacac agcaccccag tccctggccc ggctgcatcc acccaatacc    1080
ctgataaccc aggacccatt acttctaggg taaggagggt ccaggagaca gaagctgagg    1140
aaaggtctga agaagtcaca tctgtcctgg ccagagggga aaaaccatca gatgctgaac    1200
caggagaatg ttgacccagg aaagggaccg aggacccaag aaaggagtca gaccaccagg    1260
gtttgcctga gaggaaggat caaggccccg agggaaagca gggctggctg catgtgcagg    1320
acactggtgg ggcatatgtg tcttagattc tccctgaatt cagtgtccct gccatggcca    1380
gactctctac tcaggcctgg acatgctgaa ataggacaat ggccttgtcc tctctcccca    1440
ccatttggca agagacataa aggacattcc aggacatgcc ttcctgggag gtccaggttc    1500
tctgtctcac acctcaggga ctgtagttac tgcatcagcc atggtaggtg ctgatctcac    1560
ccagcctgtc caggcccttc cactctccac tttgtgacca tgtccaggac cacccctcag    1620
atcctgagcc tgcaaatacc cccttgctgg gtgggtggat tcagtaaaca gtgagctcct    1680
```

FIG. 23*ii*

```
atccagcccc cagagccacc tctgtcacct tcctgctggg catcatccca ccttcacaag    1740
cactaaagag catggggaga cctggctagc tgggtttctg catcacaaag aaaataatcc    1800
cccaggttcg gattcccagg gctctgtatg tggagctgac agacctgagg ccaggagata    1860
gcagaggtca gccctaggga gggtgggtca tccacccagg ggacaggggt gcaccagcct    1920
tgctactgaa agggcctccc caggacagcg ccatcagccc tgcctgagag ctttgctaaa    1980
cagcagtcag aggaggccat ggcagtggct gagctcctgc tccaggcccc aacagaccag    2040
accaacagca caatgcagtc cttccccaac gtcacaggtc accaaaggga aactgaggtg    2100
ctacctaacc ttagagccat caggggagat aacagcccaa tttcccaaac aggccagttt    2160
caatcccatg acaatgacct ctctgctctc attcttccca aaataggacg ctgattctcc    2220
cccaccatgg atttctccct tgtcccggga gccttttctg ccccctatga tctgggcact    2280
cctgacacac acctcctctc tggtgacata tcagggtccc tcactgtcaa gcagtccaga    2340
aaggacagaa ccttggacag cgcccatctc agcttcaccc ttcctccttc acagggttca    2400
gggcaaagaa taaatggcag aggccagtga gcccagagat ggtgacaggc agtgacccag    2460
gggcagatgc ctggagcagg agctggcggg gccacaggga gaaggtgatg caggaaggga    2520
aacccagaaa tgggcaggaa aggaggacac aggctctgtg gggctgcagc ccagggttgg    2580
actatgagtg tgaagccatc tcagcaagta aggccaggtc ccatgaacaa gagtgggagc    2640
acgtggcttc ctgctctgta tatggggtgg gggattccat gccccataga accagatggc    2700
cggggttcag atggagaagg agcaggacag gggatcccca ggataggagg accccagtgt    2760
ccccacccag gcaggtgact gatgaatggg catgcagggt cctcctgggc tgggctctcc    2820
ctttgtccct caggattcct tgaaggaaca tccggaagcc gaccacatct acctggtggg    2880
ttctggggag tccatgtaaa gccaggagct tgtgttgcta ggaggggtca tggcatgtgc    2940
tgggggcacc aaagagagaa acctgagggc aggcaggacc tggtctgagg aggcatggga    3000
gcccagatgg ggagatggat gtcaggaaag gctgccccat cagggagggt gatagcaatg    3060
gggggtctgt gggagtgggc acgtgggatt ccctgggctc tgccaagttc cctcccatag    3120
tcacaacctg gggacactgc ccatgaaggg gcgcctttgc ccagccagat gctgctggtt    3180
ctgcccatcc actaccctct ctgctccagc cactctgggt ctttctccag atgccctgga    3240
cagccctggc ctgggcctgt cccctgagag gtgttgggag aagctgagtc tctggggaca    3300
ctctcatcag agtctgaaag gcacatcagg aaacatccct ggtctccagg actaggcaat    3360
```

FIG. 23*iii*

```
gaggaaaggg ccccagctcc tccctttgcc actgagaggg tcgaccctgg gtggccacag   3420
tgacttctgc gtctgtccca gtcaccctga aaccacaaca aaacccccagc cccagaccct  3480
gcaggtacaa tacatgtggg gacagtctgt acccagggga agccagttct ctcttcctag   3540
gagaccgggc ctcagggctg tgcccggggc aggcgggggc agcacgtgcc tgtccttgag   3600
aactcgggac cttaagggtc tctgctctgt gaggcacagc aaggatcctt ctgtccagag   3660
atgaaagcag ctcctgcccc tcctctgacc tcttcctcct tcccaaatct caaccaacaa   3720
ataggtgttt caaatctcat catcaaatct tcatccatcc acatgagaaa gcttaaaacc   3780
caatggattg acaacatcaa gagttggaac aagtggacat ggagatgtta cttgtggaaa   3840
tttagatgtg ttcagctatc gggcaggaga atctgtgtca aattccagca tggttcagaa   3900
gaatcaaaaa gtgtcacagt ccaaatgtgc aacagtgcag gggataaaac tgtggtgcat   3960
tcaaactgag ggatattttg gaacatgaga aaggaaggga ttgctgctgc acagaacatg   4020
gatgatctca cacatagagt tgaaagaaag gagtcaatcg cagaatagaa aatgatcact   4080
aattccacct ctataaagtt tccaagagga aaacccaatt ctgctgctag agatcagaat   4140
ggaggtgacc tgtgccttgc aatggctgtg agggtcacgg gagtgtcact tagtgcaggc   4200
aatgtgccgt atcttaatct gggcagggct ttcatgagca cataggaatg cagacattac   4260
tgctgtgttc atttacttc accggaaaag aagaataaaa tcagccgggc gcggtggctc    4320
acgcctgtaa tcccagcact ttagaaggct gaggtgggca gattacttga ggtcaggagt   4380
tcaagaccac cctggccaat atggtgaaac cccggctcta ctaaaaatac aaaaattagc   4440
tgggcatggt ggtgcgcgcc tgtaatccca gctactcggg aggctgaggc tggacaattg   4500
cttggaccca ggaagcagag gttgcagtga gccaagattg tgccactgca ctccagcttg   4560
ggcaacagag ccagactctg taaaaaaaaa aaaaaaaaaa aaaaaaagaa agaaagaaaa   4620
agaaaagaaa gtataaaatc tctttgggtt aacaaaaaaa gatccacaaa acaaacacca   4680
gctcttatca aacttacaca actctgccag agaacaggaa acacaaatac tcattaactc   4740
acttttgtgg caataaaacc ttcatgtcaa aaggagacca ggacacaatg aggaagtaaa   4800
actgcaggcc ctacttgggt gcagagaggg aaaatccaca aataaaacat taccagaagg   4860
agctaagatt tactgcattg agttcattcc ccaggtatgc aaggtgattt taacacctga   4920
aaatcaatca ttgcctttac tacatagaca gattagctag aaaaaaatta caactagcag   4980
aacagaagca atttggcctt cctaaaattc cacatcatat catcatgatg gagacagtgc   5040
agacgccaat gacaataaaa agagggacct ccgtcacccg gtaaacatgt ccacacagct   5100
```

FIG. 23*iv*

```
ccagcaagca cccgtcttcc cagtgaatca ctgtaacctc ccctttaatc agccccaggc   5160
aaggctgcct gcgatggcca cacaggctcc aacccgtggg cctcaacctc ccgcagaggc   5220
tctcctttgg ccaccccatg gggagagcat gaggacaggg cagagccctc tgatgcccac   5280
acatggcagg agctgacgcc agagccatgg gggctggaga gcagagctgc tggggtcaga   5340
gcttcctgag gacacccagg cctaagggaa ggcagctccc tggatggggg caaccaggct   5400
ccgggctcca acctcagagc ccgcatggga ggagccagca ctctaggcct ttcctagggt   5460
gactctgagg ggaccctgac acgacaggat cgctgaatgc acccgagatg aaggggccac   5520
cacgggaccc tgctctcgtg gcagatcagg agagagtggg acaccatgcc aggcccccat   5580
ggcatggctg cgactgaccc aggccactcc cctgcatgca tcagcctcgg taagtcacat   5640
gaccaagccc aggaccaatg tggaaggaag gaaacagcat cccctttagt gatggaaccc   5700
aaggtcagtg caaagagagg ccatgagcag ttaggaaggg tggtccaacc tacagcacaa   5760
accatcatct atcataagta gaagccctgc tccatgaccc ctgcatttaa ataaacgttt   5820
gttaaatgag tcaaattccc tcaccatgag agctcacctg tgtgtaggcc catcacacac   5880
acaaacacac acacacacac acacacacac acacacacac acagggaaag tgcaggatcc   5940
tggacagcac caggcaggct tcacaggcag agcaaacagc gtgaatgacc catgcagtgc   6000
cctgggcccc atcagctcag agaccctgtg agggctgaga tggggctagg caggggagag   6060
acttagagag ggtggggcct ccagggaggg ggctgcaggg agctgggtac tgccctccag   6120
ggagggggct gcagggagct gggtactgcc ctccagggag gggggctgcag ggagctgggt   6180
actgccctcc agggaggggg ctgcagggag ctgggtactg ccctccaggg agggggctgc   6240
agggagctgg gtactgccct ccagggaggc aggagcactg ttcccaacag agagcacatc   6300
ttcctgcagc agctgcacag acacaggagc ccccatgact gccctgggcc agggtgtgga   6360
ttccaaattt cgtgccccat tgggtgggac ggaggttgac cgtgacatcc aaggggcatc   6420
tgtgattcca aacttaaact actgtgccta caaaatagga aataacccta ctttttctac   6480
tatctcaaat tccctaagca caagctagca ccctttaaat caggaagttc agtcactcct   6540
ggggtcctcc catgcccccca gtctgacttg caggtgcaca gggtggctga catctgtcct   6600
tgctcctcct cttggctcaa ctgccgcccc tcctgggggt gactgatggt caggacaagg   6660
gatcctagag ctggccccat gattgacagg aaggcaggac ttggcctcca ttctgaagac   6720
taggggtgtc aagagagctg ggcatcccac agagctgcac aagatgacgc ggacagaggg   6780
```

FIG. 23v

```
tgacacaggg ctcagggctt cagacgggtc gggaggctca gctgagagtt cagggacaga    6840
cctgaggagc ctcagtggga aaagaagcac tgaagtggga agttctggaa tgttctggac    6900
aagcctgagt gctctaagga aatgctccca ccccgatgta gcctgcagca ctggacggtc    6960
tgtgtacctc cccgctgccc atcctctcac agcccccgcc tctagggaca caactcctgc    7020
cctaacatgc atctttcctg tctcattcca cacaaaaggg cctctggggt ccctgttctg    7080
cattgcaagg agtggaggtc acgttcccac agaccaccca gcaacagggt cctatggagg    7140
tgcggtcagg aggatcacac gtcccccat gcccagggga ctgactctgg gggtgatgga     7200
ttggcctgga ggccactggt cccctctgtc cctgagggga atctgcaccc tggaggctgc    7260
cacatccctc ctgattcttt cagctgaggg cccttcttga aatcccaggg aggactcaac    7320
ccccactggg aaaggcccag tgtggacggt tccacagcag cccagctaag gcccttggac    7380
acagatcctg agtgagagaa cctttaggga cacaggtgca cggccatgtc cccagtgccc    7440
acacagagca ggggcatctg gaccctgagt gtgtagctcc cgcgactgaa cccagccctt    7500
ccccaatgac gtgacccctg gggtggctcc aggtctccag tccatgccac caaaatctcc    7560
agattgaggg tcctcccttg agtccctgat gcctgtccag gagctgcccc ctgagcaaat    7620
ctagagtgca gagggctggg attgtggcag taaaagcagc cacatttgtc tcaggaagga    7680
aagggaggac atgagctcca ggaagggcga tggcgtcctc tagtgggcgc ctcctgttaa    7740
tgagcaaaaa ggggccagga gagttgagag atcagggctg gccttggact aaggctcaga    7800
tggagaggac tgaggtgcaa agaggggct gaagtagggg agtggtcggg agagatggga    7860
ggagcaggta aggggaagcc ccagggaggc cgggggaggg tacagcagag ctctccactc    7920
ctcagcattg acatttgggg tggtcgtgct agtggggttc tgtaagttgt agggtgttca    7980
gcaccatctg gggactctac ccactaaatg ccagcaggac tccctcccca agctctaaca    8040
accaacaatg tctccagact ttccaaatgt cccctggaga gcaaaattgc ttctggcaga    8100
atcactgatc tacgtcagtc tctaaaagtg actcatcagc gaaatccttc acctcttggg    8160
agaagaatca caagtgtgag aggggtagaa actgcagact tcaaaatctt tccaaaagag    8220
ttttacttaa tcagcagttt gatgtcccag gagaagatac atttagagtg tttagagttg    8280
atgccacatg gctgcctgta cctcacagca ggagcagagt gggttttcca agggcctgta    8340
accacaactg gaatgacact cactggggtta cattacaaag tggaatgtgg ggaattctgt    8400
agactttggg aagggaaatg tatgacgtga gcccacagcc taaggcagtg gacagtccac    8460
tttgaggctc tcaccatcta ggagacatct cagccatgaa catagccaca tctgtcatta    8520
```

FIG. 23*vi*

```
gaaaacatgt tttattaaga ggaaaaatct aggctagaag tgctttatgc tctttttttct    8580
ctttatgttc aaattcatat actttagat cattccttaa agaagaatct atccccctaa    8640
gtaaatgtta tcactgactg gatagtgttg gtgtctcact cccaacccct gtgtggtgac    8700
agtgccctgc ttccccagcc ctgggccctc tctgattcct gagagctttg ggtgctcctt    8760
cattaggagg aagagaggaa gggtgttttt aatattctca ccattcaccc atccacctct    8820
tagacactgg gaagaatcag ttgcccactc ttggatttga tcctcgaatt aatgacctct    8880
atttctgtcc cttgtccatt tcaacaatgt gacaggccta agaggtgcct tctccatgtg    8940
atttttgagg agaaggttct caagataagt tttctcacac ctctttgaat tacctccacc    9000
tgtgtcccca tcaccattac cagcagcatt tggacccttt ttctgttagt cagatgcttt    9060
ccacctcttg agggtgtata ctgtatgctc tctacacagg aatatgcaga ggaaatagaa    9120
aaagggaaat cgcattacta ttcagagaga agaagacctt tatgtgaatg aatgagagtc    9180
taaaatccta agagagccca tataaaatta ttaccagtgc taaaactaca aaagttacac    9240
taacagtaaa ctagaataat aaaacatgca tcacagttgc tggtaaagct aaatcagata    9300
tttttttctt agaaaaagca ttccatgtgt gttgcagtga tgacaggagt gcccttcagt    9360
caatatgctg cctgtaattt ttgttccctg gcagaatgta ttgtcttttc tccctttaaa    9420
tcttaaatgc aaaactaaag gcagctcctg ggccccctcc ccaaactcag ctgcctgcaa    9480
ccagccccac gaagagcaga ggcctgagct tccctggtca aaatacgggg ctagggagct    9540
taaccttgct cgataaagct gtgttcccag aatgtcgctc ctgttcccag gggcaccagc    9600
ctggagggtg gtgagcctca ctggtggcct gatgcttacc ttgtgccctc acaccagtgg    9660
tcactggaac cttgaacact tggctgtcgc ccggatctgc agatgtcaag aacttctgga    9720
agtcaaatta ctgcccactt ctccagggca gatacctgtg aacatccaaa accatgccac    9780
agaaccctgc ctggggtcta caacacatat ggactgtgag caccaagtcc agccctgaat    9840
ctgtgaccac ctgccaagat gcccctaact gggatccacc aatcactgca catggcaggc    9900
agcgaggctt ggaggtgctt cgccacaagg cagccccaat ttgctgggag tttcttggca    9960
cctggtagtg gtgaggagcc ttgggaccct caggattact ccccttaagc atagtgggga   10020
cccttctgca tccccagcag gtgccccgct cttcagagcc tctctctctg aggtttaccc   10080
agacccctgc accaatgaga ccatgctgaa gcctcagaga gagagatgga gctttgacca   10140
ggagccgctc ttccttgagg gccagggcag ggaaagcagg aggcaccacc aggagtggga   10200
```

FIG. 23*vii*

```
acaccagtgt ctaacgccct gatgagaaca gggtggtctc tcccatatgc ccataccagg   10260
cctgtgaaca gaatcctcct tctgcagtga caatgtctga gaggacgaca tgtttcccag   10320
cctaacgtgc agccatgccc atctacccac tgcctactgc aggacagcac caacccagga   10380
gctgggaagc tgggagaaga catggaatac ccatggcttc tcaccttcct ccagtccagt   10440
gggcaccatt tatgcctagg acacccacct gccggcccca ggctcttaag agttaggtca   10500
cctaggtgcc tctgggaggc cgaggcagga gaattgcttg aacccgggag gcagaggttg   10560
cagtgagccg agatcacacc actgcactcc agcctgggtg acagaatgag actctgtctc   10620
aaaaaaaaag agaaagatag catcagtggc taccaagggc taggggcagg ggaaggtgga   10680
gagttaatga ttaatagtat gaagtttcta tgtgagatga tgaaaatgtt ctggaaaaaa   10740
aaatatagtg gtgaggatgt agaatattgt gaatataatt aacggcattt aattgtacac   10800
ttaacatgat taatgtggca tattttatct tatgtatttg actacatcca agaaacactg   10860
ggagagggaa agcccaccat gtaaaataca cccaccctaa tcagatagtc ctcattgtac   10920
ccaggtacag gcccctcatg acctgcacag gaataactaa ggatttaagg acatgaggct   10980
tcccagccaa ctgcaggtgc acaacataaa tgtatctgca aacagactga gagtaaagct   11040
gggggcacaa acctcagcac tgccaggaca cacacccttc tcgtggattc tgactttatc   11100
tgacccggcc cactgtccag atcttgttgt gggattggga caagggaggt cataaagcct   11160
gtccccaggg cactctgtgt gagcacacga gacctcccca ccccccccacc gttaggtctc   11220
cacacataga tctgaccatt aggcattgtg aggaggactc tagcgcgggc tcagggatca   11280
caccagagaa tcaggtacag agaggaagac ggggctcgag gagctgatgg atgacacaga   11340
gcagggttcc tgcagtccac aggtccagct caccctggtg taggtgcccc atccccctga   11400
tccaggcatc cctgacacag ctccctcccg gagcctcctc ccaggtgaca catcagggtc   11460
cctcactcaa gctgtccaga gagggcagca ccttggacag cgcccacccc acttcactct   11520
tcctccctca cagggctcag ggctcagggc tcaagtctca gaacaaatgg cagaggccag   11580
tgagcccaga gatggtgaca gggcaatgat ccaggggcag ctgcctgaaa cgggagcagg   11640
tgaagccaca gatgggagaa gatggttcag gaagaaaaat ccaggaatgg gcaggagagg   11700
agaggaggac acaggctctg tggggctgca gcccaggatg ggactaagtg tgaagacatc   11760
tcagcaggtg aggccaggtc ccatgaacag agaagcagct cccacctccc ctgatgcacg   11820
gacacacaga gtgtgtggtg ctgtgccccc agagtcgggc tctcctgttc tggtccccag   11880
ggagtgagaa gtgaggttga cttgtccctg ctcctctctg ctaccccaac attcaccttc   11940
```

FIG. 23viii

```
tcctcatgcc cctctctctc aaatatgatt tggatctatg tccccgccca aatctcatgt   12000
caaattgtaa accccaatgt tggaggtggg gccttgtgag aagtgattgg ataatgcggg   12060
tggattttct gctttgatgc tgtttctgtg atagagatct cacatgatct ggttgtttaa   12120
aagtgtgtag cacctctccc ctctctctct ctctctctta ctcatgctct gccatgtaag   12180
acgttcctgt ttccccttca ccgtccagaa tgattgtaag ttttctgagg cctccccagg   12240
agcagaagcc actatgcttc ctgtacaact gcagaatgat gagcgaatta aacctctttt   12300
ctttataaat tacccagtct caggtatttc tttatagcaa tgcgaggaca gactaataca   12360
atcttctact cccagatccc cgcacacgct tagccccaga catcactgcc cctgggagca   12420
tgcacagcgc agcctcctgc cgacaaaagc aaagtcacaa aaggtgacaa aaatctgcat   12480
ttggggacat ctgattgtga aagagggagg acagtacact tgtagccaca gagactgggg   12540
ctcaccgagc tgaaacctgg tagcactttg gcataacatg tgcatgaccc gtgttcaatg   12600
tctacagatc agtgttgagt aaaacagcct ggtctggggc cgctgctgtc cccacttccc   12660
tcctgtccac cagagggcgg cagagttcct cccaccctgg agcctcccca ggggctgctg   12720
acctccctca gccgggccca cagcccagca gggtccaccc tcacccgggt cacctcggcc   12780
cacgtcctcc tcgccctccg agctcctcac acggactctg tcagctcctc cctgcagcct   12840
atcggccgcc cacctgaggc ttgtcggccg cccacttgag gcctgtcggc tgccctctgc   12900
aggcagctcc tgtcccctac accccctcct tccccgggct cagctgaaag ggcgtctccc   12960
agggcagctc cctgtgatct ccaggacagc tcagtctctc acaggctccg acgcccccta   13020
tgctgtcacc tcacagccct gtcattacca ttaactcctc agtcccatga agttcactga   13080
gcgcctgtct cccggttaca ggaaaactct gtgacaggga ccacgtctgt cctgctctct   13140
gtggaatccc agggcccagc ccagtgcctg acacggaaca gatgctccat aaatactggt   13200
taaatatgtg ggagatctct aaaaagaagc atatcacctc cgtgtggccc ccagcagtca   13260
gagtctgttc catgtggaca caggggcact ggcaccagca tgggaggagg ccagcaagtg   13320
cccgcagctg ccccaggaat gaggcctcaa cccccagagc ttcagaaggg aggacagagg   13380
cctgcaggga atagatcctc cggcctgacc ctgcagccta atccagagtt cagggtcagc   13440
tcacaccacg tcgaccctgg tcagcatccc tagggcagtt ccagacaagg ccggaggtct   13500
cctcttgccc tccagggggt gacattgcac acagacatca ctcaggaaac ggattcccct   13560
ggacaggaac ctggctttgc taaggaagtg gaggtggagc ctggtttcca tcccttgctc   13620
```

FIG. 23*ix*

```
caacagaccc ttctgatctc tcccacatac ctgctctgtt cctttctcgg tcctatgagg   13680
accctgttct gccaggggtc cctgtgcaac tccagactcc ctcctggtac caccatgggg   13740
aaggtggggt gatcacagga cagtcagcct cgcagagaca gagaccaccc aggactgtca   13800
gggagaacat ggacaggccc tgagccgcag ctcagccaac agacacggag agggagggtc   13860
cccctggagc cttccccaag gacagcagag cccagagtca cccacctccc tccaccacag   13920
tcctctcttt ccaggacaca caagacacct ccccctccac atgcaggatc tggggactcc   13980
tgagacctct gggcctgggt ctccatccct gggtcagtgg cggggttggt ggtactggag   14040
acagagggct ggtccctccc cagccaccac ccagtgagcc tttttctagc ccccagagcc   14100
acctctgtca ccttcctgtt gggcatcatc ccaccttccc agagccctgg agagcatggg   14160
gagacccggg accctgctgg gtttctctgt cacaaaggaa aataatcccc ctggtgtgac   14220
agacccaagg acagaacaca gcagaggtca gcactgggga agacaggttg tcctcccagg   14280
ggatgggggt ccatccacct tgccgaaaag atttgtctga ggaactgaaa atagaaggga   14340
aaaaagagga gggacaaaag aggcagaaat gagaggggag gggacagagg acacctgaat   14400
aaagaccaca cccatgaccc acgtgatgct gagaagtact cctgccctag gaagagactc   14460
agggcagagg gaggaaggac agcagaccag acagtcacag cagccttgac aaaacgttcc   14520
tggaactcaa gctcttctcc acagaggagg acagagcaga cagcagagac catggagtct   14580
ccctcggccc ctccccacag atggtgcatc ccctggcaga ggctcctgct cacaggtgaa   14640
gggaggacaa cctgggagag ggtgggagga gggagctggg gtctcctggg taggacaggg   14700
ctgtgagacg gacagagggc tcctgttgga gcctgaatag ggaagaggac atcagagagg   14760
gacaggagtc acaccagaaa aatcaaattg aactggaatt ggaaaggggc aggaaaacct   14820
caacagttct attttcctag ttaattgtca ctggccacta cgtttttaaa aatcataata   14880
actgcatcag atgacacttt aaataaaaac ataaccaggg catgaaacac tgtcctcatc   14940
cgcctaccgc ggacattgga aaataagccc caggctgtgg agggccctgg gaaccctcat   15000
gaactcatcc acaggaatct gcagcctgtc ccaggcactg gggtgcaacc aagatc       15056
```

FIG. 24*i*

```
gaattcagaa ataggggaag gttgaggaag gacactgaac tcaaagggga tacagtgatt     60
ggtttatttg tcttctcttc acaacattgg tgctggagga attcccaccc tgaggttatg    120
aagatgtctg aacacccaac acatagcact ggagatatga gctcgacaag agtttctcag    180
ccacagagat tcacagccta gggcaggagg acactgtacg ccaggcagaa tgacatggga    240
attgcgctca cgattggctt gaagaagcaa ggactgtggg aggtgggctt tgtagtaaca    300
agagggcagg gtgaactctg attcccatgg gggaatgtga tggtcctgtt acaaattttt    360
caagctggca gggaataaaa cccattacgg tgaggacctg tggagggcgg ctgccccaac    420
tgataaagga aatagccagg tgggggcctt tcccattgta ggggggacat atctggcaat    480
agaagccttt gagacccttt agggtacaag tactgaggca gcaaataaaa tgaaatctta    540
tttttcaact ttatactgca tgggtgtgaa gatatatttg tttctgtaca gggggtgagg    600
gaaaggaggg gaggaggaaa gttcctgcag gtctggtttg gtcttgtgat ccaggggtc     660
ttggaactat ttaaattaaa ttaaattaaa acaagcgact gttttaaatt aaattaaatt    720
aaattaaatt ttactttatt ttatcttaag ttctgggcta catgtgcagg acgtgcagct    780
ttgttacata ggtaaacgtg tgccatggtg gtttgctgta cctatcaacc catcacctag    840
gtattaagcc cagcatgcat tagctgtttt tcctgacgct ctccctctcc ctgactccca    900
caacaggccc cagtgtgtgt tgttcccctc cctgtgtcca tgtgttctca ttgttcagct    960
cccacttata agtgagaaca tgtggtgttt ggttttctgt ttctgtgtta gtttgctgag   1020
gataatggct tccacctcca tccatgttcc tgcaaaggac gtgatcttat tctttttat    1080
ggttgcatag aaattgtttt tacaaatcca attgatattg tatttaatta caagttaatc   1140
taattagcat actagaagag attacagaag atattaggta cattgaatga ggaaatatat   1200
aaaataggac gaaggtgaaa tattaggtag gaaaagtata atagttgaaa gaagtaaaaa   1260
aaaatatgca tgagtagcag aatgtaaaag aggtgaagaa cgtaatagtg actttttaga   1320
ccagattgaa ggacagagac agaaaaattt taaggaattg ctaaaccatg tgagtgttag   1380
aagtacagtc aataacatta aagcctcagg aggagaaaag aataggaaag gaggaaatat   1440
gtgaataaat agtagagaca tgtttgatgg attttaaaat atttgaaaga cctcacatca   1500
aaggattcat accgtgccat tgaagaggaa gatggaaaag ccaagaagcc agatgaaagt   1560
tagaaatatt attggcaaag cttaaatgtt aaaagtccta gagagaaagg atggcagaaa   1620
tattggcggg aaagaatgca gaacctagaa tataaattca tcccaacagt ttggtagtgt   1680
```

FIG. 24ii

```
gcagctgtag cctttctag ataatacact attgtcatac atcgcttaag cgagtgtaaa 1740
atggtctcct cactttattt atttatatat ttatttagtt ttgagatgga gcctcgctct 1800
gtctcctagg ctggagtgca atagtgcgat accactcact gcaacctctg cctcctctgt 1860
tcaagtgatt ttcttacctc agcctcccga gtagctggga ttacaggtgc gtgccaccac 1920
acccggctaa tttttgtatt ttttgtagag acggggtttt gccatgttgg ccaggctggt 1980
cttgaactcc tgacatcagg tgatccacct gccttggcct cctaaagtgc tgggattaca 2040
ggcatgagcc accgtgccca accactttat ttattttta tttttatttt taaatttcag 2100
cttctatttg aaatacaggg ggcacatata taggattgtt acatgggtat attgaactca 2160
ggtagtgatc atactaccca acaggtaggt tttcaaccca ctccccctct tttcctcccc 2220
attctagtag tgtgcagtgt ctattgttct catgtttatg tctatgtgtg ctccaggttt 2280
agctcccacc tgtaagtgag aacgtgtggt atttgatttt ctgtccctgt gttaattcac 2340
ttaggattat ggcttccagc tccattcata ttgctgtaaa ggatatgatt cattttcat 2400
ggccatgcag tattccatat tgcgtataga tcacattttc tttcttttt tttttgaga 2460
cggagtcttg ctttgctgcc taggctggag tgcagtagca cgatctcggc tcactgcaag 2520
cttcacctcc ggggttcacg tcattcttct gtctcagctt cccaagtagc tgggactaca 2580
ggcgcccgcc accacgtccg gctaattttt ttgtgtgttt ttagtagaga tggggtttc 2640
actgtgttag ccaggatggt cttgatctcc tgaccttgtg gtccacctgc ctcggtctcc 2700
caaagtgctg ggattacagg ggtgagccac tgcgcccggc ccatatatac cacattttct 2760
ttaaccaatc caccattgat gggcaactag gtagattcca tggattccac agttttgcta 2820
ttgtgtgcag tgtggcagta gacatatgaa tgaatgtgtc tttttggtat aatgatttgc 2880
attcctttgg gtatacagtc attaatagga gtgctgggtt gaacggtggc tctgtttaaa 2940
attctttgag aattttccaa actgtttgcc atagagagca aactaattta catttccacg 3000
aacagtatat aagcattccc ttttctccac agctttgtca tcatggtttt ttttttctt 3060
tattttaaaa aagaatatgt tgttgttttc ccagggtaca tgtgcaggat gtgcaggttt 3120
gttacatagg tagtaaacgt gagccatggt ggtttgctgc acctgtcaac ccattacctg 3180
ggtatgaagc cctgcctgca ttagctcttt tccctaatgc tctcactact gccccaccct 3240
caccctgaca gggcaaacag acaacctaca gaatgggagg aaatttttgc aatctattca 3300
tctgacaaag gtcaagaata tccagaatct acaaggaact taagcaaatt tttactttt 3360
```

FIG. 24*iii*

```
aataatagcc actctgactg gcgtgaaatg gtatctcatt gtggttttca tttgaatttc   3420
tctgatgatc agtgacgatg agcatttttt catatttgtt ggctgcttgt acgtcttttg   3480
agaagtgtct cttcatgcct tttggccact ttaatgggat tatttttgc ttttagttt    3540
aagttcctta tagattctgg atattagact tcttattgga tgcatagttt gtgaatactc   3600
tcttccattc tgtaggttgt ctgtttactc tattgatggc ttcttttgct gtgccgaagc   3660
atcttagttt aattagaaac cacctgccaa tttttgtttt tgttgcaatt gcttttgggg   3720
acttagtcat aaactctttg ccaaggtctg ggtcaagaag agtatttcct aggttttctt   3780
ctagaatttt gaaagtctga atgtaaacat ttgcattttt aatgcatctt gagttagttt   3840
ttgtatatgt gaaaggtcta ctctcatttt ctttccctct ttctttcttt ctttcttttc   3900
tttctttctt tctttctttc tttctttctt tctttctttc tttcttttg tccttctttc    3960
tttctttctt tctctttctt tctctctttc ttttttttt ttgatggagt attgctctgt    4020
tgcccaggct gcagtgcagc ggcacgatct cggctcactg caacctctgc ctcctgggtt   4080
caactgattc tcctgcatca gccttccaag tagctgggat tataggcgcc cgccaccacg   4140
cccgactaat ttttgtattt ttagtagaga cggggttgtg ccatgttggc caggctggtt   4200
tgaaactcct gacctcaaac gatctgcctg ccttggcctc ccaaagtgct gggattacag   4260
gtgtgagcca ctgtgcccag ccaagaatgt catttctaa gaggtccaag aacctcaaga    4320
tattttggga ccttgagaag agaggaattc atacaggtat tacaagcaca gcctaatggc   4380
aaatctttgg catggcttgg cttcaagact ttaggctctt aaaagtcgaa tccaaaaatt   4440
tttataaaag ctccagctaa gctaccttaa aaggggcctg tatggctgat cactcttctt   4500
gctatacttt acacaaataa acaggccaaa tataatgagg ccaaaattta ttttgcaaat   4560
aaattggtcc tgctatgatt tactcttggt aagaacaggg aaaatagaga aaaatttaga   4620
ttgcatctga ccttttttc tgaattttta tatgtgccta caatttgagc taaatcctga    4680
attattttct ggttgcaaaa actctctaaa gaagaacttg gttttcattg tcttcgtgac   4740
acatttatct ggctctttac tagaacagct ttcttgtttt tggtgttcta gcttgtgtgc   4800
cttacagttc tactcttcaa attattgtta tgtgtatctc atagttttcc ttcttttgag   4860
aaaactgaag ccatggtatt ctgaggacta gagatgactc aacagagctg gtgaatctcc   4920
tcatatgcaa tccactgggc tcgatctgct tcaaattgct gatgcactgc tgctaaagct   4980
atacatttaa aaccctcact aaaggatcag ggaccatcat ggaagaggag gaaacatgaa   5040
attgtaagag ccagattcgg ggggtagagt gtggaggtca gagcaactcc accttgaata   5100
```

FIG. 24*iv*

```
agaaggtaaa gcaacctatc ctgaaagcta acctgccatg gtggcttctg attaacctct 5160
gttctaggaa gactgacagt ttgggtctgt gtcattgccc aaatctcatg ttaaattgta 5220
atccccagtg ttcggaggtg ggacttggtg gtaggtgatt cggtcatggg agtagatttt 5280
cttctttgtg gtgttacagt gatagtgagt gagttctcgt gagatctggt catttaaaag 5340
tgtgtggccc ctcccctccc tctcttggtc ctcctactgc catgtaagat acctgctcct 5400
gctttgcctt ctaccataag taaaagcccc ctgaggcctc cccagaagca gatgccacca 5460
tgcttcctgt acagcctgca gaaccatcag ccaattaaac ctcttttctg tataaattac 5520
cagtcttgag tatctcttta cagcagtgtg agaacggact aatacaaggg tctccaaaat 5580
tccaagttta tgtattcttt cttgccaaat agcaggtatt taccataaat cctgtcctta 5640
ggtcaaacaa ccttgatggc atcgtacttc aattgtctta cacattcctt ctgaatgact 5700
cctcccctat ggcatataag ccctgggtct tgggggataa tggcagaggg gtccaccatc 5760
ttgtctggct gccacctgag acacggacat ggcttctgtt ggtaagtctc tattaaatgt 5820
ttctttctaa gaaactggat ttgtcagctt gtttctttgg cctctcagct tcctcagact 5880
ttggggtagg ttgcacaacc ctgcccacca cgaaacaaat gtttaatatg ataaatatgg 5940
atagatataa tccacataaa taaaagctct tggagggccc tcaataattg ttaagagtgt 6000
aaatgtgtcc aaagatggaa aatgtttgag aactactgtc ccagagattt tcctgagttc 6060
tagagtgtgg gaatatagaa cctggagctt ggcttcttca gcctagaatc aggagtatgg 6120
ggctgaagtc tgaagcttgg cttcagcagt ttggggttgg cttccggagc acatatttga 6180
catgttgcga ctgtgatttg gggtttggta tttgctctga atcctaatgt ctgtccttga 6240
ggcatctaga atctgaaatc tgtggtcaga attctattat cttgagtagg acatctccag 6300
tcctggttct gccttctagg gctggagtct gtagtcagtg acccggtctg gcatttcaac 6360
ttcatataca gtgggctatc ttttggtcca tgtttcaacc aaacaaccga ataaaccatt 6420
agaacctttc cccacttccc tagctgcaat gttaaaccta ggatttctgt ttaataggtt 6480
catatgaata atttcagcct gatccaactt tacattcctt ctaccgttat tctacaccca 6540
ccttaaaaat gcattcccaa tatattccct ggattctacc tatatatggt aatcctggct 6600
ttgccagttt ctagtgcatt aacatacctg atttacattc ttttacttta aagtggaaat 6660
aagagtccct ctgcagagtt caggagttct caagatggcc cttacttctg acatcaattg 6720
agatttcaag ggagtcgcca agatcatcct caggttcagt gattgctggt agccctcata 6780
```

FIG. 24v

```
taactcaatg aaagctgtta tgctcatggc tatggtttat tacagcaaaa gaatagagat    6840
gaaaatctag caagggaaga gttgcatggg gcaaagacaa ggagagctcc aagtgcagag    6900
attcctgttg ttttctccca gtggtgtcat ggaaagcagt atcttctcca tacaatgatg    6960
tgtgataata ttcagtgtat tgccaatcag ggaactcaac tgagccttga ttatattgga    7020
gcttggttgc acagacatgt cgaccacctt catggctgaa ctttagtact tagcccctcc    7080
agacgtctac agctgatagg ctgtaaccca acattgtcac cataaatcac attgttagac    7140
tatccagtgt ggcccaagct cccgtgtaaa cacaggcact ctaaacaggc aggatatttc    7200
aaaagcttag agatgacctc ccaggagctg aatgcaaaga cctggcctct ttgggcaagg    7260
agaatccttt accgcacact ctccttcaca gggttattgt gaggatcaaa tgtggtcatg    7320
tgtgtgagac accagcacat gtctggctgt ggagagtgac ttctatgtgt gctaacattg    7380
ctgagtgcta agaaagtatt aggcatggct ttcagcactc acagatgctc atctaatcct    7440
cacaacatgg ctacagggtg ggcactacta gcctcatttg acagaggaaa ggactgtgga    7500
taagaagggg gtgaccaata ggtcagagtc attctggatg caaggggctc cagaggacca    7560
tgattagaca ttgtctgcag agaaattatg gctggatgtc tctgccccgg aaagggggat    7620
gcactttcct tgacccccta tctcagatct tgactttgag gttatctcag acttcctcta    7680
tgataccagg agcccatcat aatctctctg tgtcctctcc ccttcctcag tcttactgcc    7740
cactcttccc agctccatct ccagctggcc aggtgtagcc acagtaccta actctttgca    7800
gagaactata aatgtgtatc ctacagggga gaaaaaaaaa aagaactctg aaagagctga    7860
cattttaccg acttgcaaac acataagcta acctgccagt tttgtgctgg tagaactcat    7920
gagactcctg ggtcagaggc aaaagatttt attacccaca gctaaggagg cagcatgaac    7980
tttgtgttca catttgttca ctttgccccc caattcatat gggatgatca gagcagttca    8040
ggtggatgga cacaggggtt tgtggcaaag gtgagcaacc taggcttaga aatcctcaat    8100
cttataagaa ggtactagca aacttgtcca gtctttgtat ctgacggaga tattatcttt    8160
ataattgggt tgaaagcaga cctactctgg aggaacatat tgtatttatt gtcctgaaca    8220
gtaaacaaat ctgctgtaaa atagacgtta actttattat ctaaggcagt aagcaaacct    8280
agatctgaag gcgataccat cttgcaaggc tatctgctgt acaaatatgc ttgaaaagat    8340
ggtccagaaa agaaaacggt attattgcct ttgctcagaa gacacacaga aacataagag    8400
aaccatggaa aattgtctcc caacactgtt cacccagagc cttccactct tgtctgcagg    8460
acagtcttaa catcccatca ttagtgtgtc taccacatct ggcttcaccg tgcctaacca    8520
```

FIG. 24vi

```
agatttctag gtccagttcc ccaccatgtt tggcagtgcc ccactgccaa ccccagaata    8580
agggagtgct cagaattccg aggggacatg ggtggggatc agaacttctg ggcttgagtg    8640
cagaggggc ccatactcct tggttccgaa ggaggaagag gctggaggtg aatgtccttg     8700
gaggggagga atgtgggttc tgaactctta aatccccaag ggaggagact ggtaaggtcc    8760
cagcttccga ggtactgacg tgggaatggc ctgagaggtc taagaatccc gtatcctcgg    8820
gaaggagggg ctgaaattgt gaggggttga gttgcagggg tttgttagct tgagactcct    8880
tggtgggtcc ctgggaagca aggactggaa ccattggctc cagggtttgg tgtgaaggta    8940
atgggatctc ctgattctca aagggtcaga ggactgagag ttgcccatgc tttgatcttt    9000
ccatctactc cttactccac ttgagggtaa tcacctactc ttctagttcc acaagagtgc    9060
gcctgcgcga gtataatctg cacatgtgcc atgtcccgag gcctggggca tcatccactc    9120
atcattcagc atctgcgcta tgcgggcgag gccggcgcca tgacgtcatg tagctgcgac    9180
tatccctgca gcgcgcctct cccgtcacgt cccaaccatg gagctgtgga cgtgcgtccc    9240
ctggtggatg tggcctgcgt ggtgccaggc cggggcctgg tgtccgataa agatcctaga    9300
accacaggaa accaggactg aaaggtgcta gagaatggcc atatgtcgct gtccatgaaa    9360
tctcaaggac ttctgggtgg agggcacagg agcctgaact tacgggtttg ccccagtcca    9420
ctgtcctccc aagtgagtct cccagatacg aggcactgtg ccagcatcag cttcatctgt    9480
accacatctt gtaacaggga ctacccagga ccctgatgaa caccatggtg tgtgcaggaa    9540
gaggggtga aggcatggac tcctgtgtgg tcagagccca gagggggcca tgacgggtgg     9600
ggaggaggct gtggactggc tcgagaagtg ggatgtggtt gtgtttgatt tcctttggcc    9660
agataaagtg ctggatatag cattgaaaac ggagtatgaa gaccagttag aatggagggt    9720
caggttggag ttgagttaca gatggggtaa aattctgctt cggatgagtt tggggattgg    9780
caatctaaag gtggtttggg atggcatggc tttgggatgg aaataggttt gtttttatgt    9840
tggctgggaa gggtgtgggg attgaattgg ggatgaagta ggtttagttt tggagataga    9900
atacatggag ctggctattg catgcgagga tgtgcattag tttggtttga tctttaaata    9960
aaggaggcta ttagggttgt cttgaattag attaagttgt gttgggttga tgggttgggc    10020
ttgtgggtga tgtggttgga ttgggctgtg ttaaattggt ttgggtcagg ttttggttga    10080
ggttatcatg gggatgagga tatgcttggg acatggattc aggtggttct cattcaagct    10140
gaggcaaatt tcctttcaga cggtcattcc agggaacgag tggttgtgtg ggggaaatca    10200
```

FIG. 24*vii*

```
ggccactggc tgtgaatatc cctctatcct ggtcttgaat tgtgattatc tatgtccatt  10260
ctgtctcctt cactgtactt ggaattgatc tggtcattca gctggaaatg ggggaagatt  10320
ttgtcaaatt cttgagacac agctgggtct ggatcagcgt aagccttcct tctggtttta  10380
ttgaacagat gaaatcacat tttttttttc aaaatcacag aaatcttata gagttaacag  10440
tggactctta taataagagt taacaccagg actcttattc ttgattcttt tctgagacac  10500
caaaatgaga tttctcaatg ccaccctaat tctttttttt tttttttttt tttttgagac  10560
acagtctggg tcttttgctc tgtcactcag gctggagcgc agtggtgtga tcatagctca  10620
ctgaaccctt gacctcctgg acttaaggga tcctcctgct tcagcctcct gagtagatgg  10680
ggctacaggt gcttgccacc acacctggct aattaaattt tttttttttt tttgtagaga  10740
aagggtctca ctttgttgcc ctggctgatc ttgaacttct gacttcaagt gattcttcag  10800
ccttggactc ccaaagcact gggattgctg gcatgagcca ctcaccgtgc ctggcttgca  10860
gcttaatctt ggagtgtata aacctggctc ctgatagcta gacatttcag tgagaaggag  10920
gcattggatt ttgcatgagg acaattctga cctaggaggg caggtcaaca ggaatccccg  10980
ctgtacctgt acgttgtaca ggcatggaga atgaggagtg aggaggccgt accggaaccc  11040
catattgttt agtggacatt ggattttgaa ataataggga acttggtctg ggagagtcat  11100
atttctggat tggacaatat gtggtatcac aaggttttat gatgagggag aaatgtatgt  11160
ggggaaccat tttctgagtg tggaagtgca agaatcagag agtagctgaa tgccaacgct  11220
tctatttcag gaacatggta agttggaggt ccagctctcg ggctcagacg ggtataggga  11280
ccaggaagtc tcacaatccg atcattctga tatttcaggg catattaggt ttggggtgca  11340
aaggaagtac ttgggactta ggcacatgag actttgtatt gaaaatcaat gattggggct  11400
ggccgtggtg ctcacgcctg taatctcatc actttgggag accgaagtgg gaggatggct  11460
tgatctcaag agttggacac cagcctaggc aacatggcca gaccctctct ctacaaaaaa  11520
attaaaaatt agctggatgt ggtggtgcat gcttgtggtc tcagctatcc tggaggctga  11580
gacaggagaa tcggttgagt ctgggagttc aaggctacag ggagctgcga tcacgccgct  11640
gcactccagc ctgggaaaca gagtgagact gtctcagaat ttttttaaaa aagaatcagt  11700
gatcatccca acccctgttg ctgttcatcc tgagcctgcc ttctctggct ttgttcccta  11760
gatcacatct ccatgatcca taggccctgc ccaatctgac ctcacaccgt gggaatgcct  11820
ccagactgat ctagtatgtg tggaacagca agtgctggct ctccctcccc ttccacagct  11880
ctgggtgtgg gagggggttg tccagcctcc agcagcatgg ggagggcctt ggtcagcatc  11940
```

FIG. 24*viii*

```
taggtgccaa cagggcaagg gcggggtcct ggagaatgaa ggctttatag ggctcctcag   12000
ggaggccccc cagccccaaa ctgcaccacc tggccgtgga caccggt                 12047
```

FIG. 25

```
cgagcggccc ctcagcttcg gcgcccagcc ccgcaaggct cccggtgacc actagagggc      60
gggaggagct cctggccagt ggtggagagt ggcaaggaag gaccctaggg ttcatcggag     120
cccaggttta ctcccttaag tggaaatttc ttcccccact cctccttggc tttctccaag     180
gagggaaccc aggctgctgg aaagtccggc tggggcgggg actgtgggtt caggggagaa     240
cggggtgtgg aacgggacag ggagcggtta gaagggtggg gctattccgg gaagtggtgg     300
ggggagggag cccaaaacta gcacctagtc cactcattat ccagccctct tatttctcgg     360
ccgctctgct tcagtggacc cggggagggc ggggaagtgg agtgggagac ctaggggtgg     420
gcttcccgac cttgctgtac aggacctcga cctagctggc tttgttcccc atccccacgt     480
tagttgttgc cctgaggcta aaactagagc ccaggggccc caagttccag actgcccctc     540
ccccctcccc cggagccagg gagtggttgg tgaaaggggg aggccagctg gagaacaaac     600
gggtagtcag ggggttgagc gattagagcc cttgtaccct acccaggaat ggttggggag     660
gaggaggaag aggtaggagg taggggaggg ggcggggttt tgtcacctgt cacctgctcg     720
ctgtgcctag ggcgggcggg cggggagtgg ggggaccggt ataaagcggt aggcgcctgt     780
gcccgctcca cctctcaagc agccagcgcc tgcctgaatc tgttctgccc cctccccacc     840
catttcacca ccaccatg                                                   858
```

FIG. 26

```
aagcttccac aagtgcattt agcctctcca gtattgctga tgaatccaca gttcaggttc      60
aatggcgttc aaaacttgat caaaaatgac cagactttat attcttacac caacatctat     120
ctgattggag gaatggataa tagtcatcat gtttaaacat ctaccattcc agttaagaaa     180
atatgatagc atcttgttct tagtcttttt cttaataggg acataaagcc cacaaataaa     240
aatatgcctg aagaatggga caggcattgg gcattgtcca tgcctagtaa agtactccaa     300
gaacctattt gtatactaga tgacacaatg tcaatgtctg tgtacaactg ccaactggga     360
tgcaagacac tgcccatgcc aatcatcctg aaaagcagct ataaaaagca ggaagctact     420
ctgcaccttg tcagtgaggt ccagatacct acag                                 454
```

FIG. 27

```
gcattgctgt gaactctgta cttaggacta aactttgagc aataacacac atagattgag     60
gattgtttgc tgttagcata caaactctgg ttcaaagctc ctctttattg cttgtcttgg    120
aaaatttgct gttcttcatg gtttctcttt tcactgctat ctatttttct caaccactca    180
catggctaca ataactgtct gcaagcttat gattcccaaa tatctatctc tagcctcaat    240
cttgttccag aagataaaaa gtagtattca aatgcacatc aacgtctcca cttggagggc    300
ttaaagacgt ttcaacatac aaaccgggga gttttgcctg gaatgtttcc taaaatgtgt    360
cctgtagcac atagggtcct cttgttcctt aaaatctaat tacttttagc ccagtgctca    420
tcccacctat ggggagatga gagtgaaaag ggagcctgat taataattac actaagtcaa    480
taggcataga gccaggactg tttgggtaaa ctggtcactt tatcttaaac taaatatatc    540
caaaactgaa catgtactta gttactaagt ctttgacttt atctcattca taccactcag    600
ctttatccag gccacttatg agctctgtgt ccttgaacat aaaatacaaa taaccgctat    660
gctgttaatt attggcaaat gtcccatttt caacctaagg aaataccata aagtaacaga    720
tataccaaca aaaggttact agttaacagg cattgcctga aaagagtata aaagaatttc    780
agcatgattt tccatattgt gcttccacca ctgccaataa ca                        822
```

FIG. 28*i*

```
gaattcttag aaatatgggg gtaggggtgg tggtggtaat tctgttttca ccccataggt      60
gagataagca ttgggttaaa tgtgctttca cacacacatc acatttcata agaattaagg     120
aacagactat gggctggagg actttgagga tgtctgtctc ataacacttg ggttgtatct     180
gttctatggg gcttgtttta agcttggcaa cttgcaacag ggttcactga ctttctcccc     240
aagcccaagg tactgtcctc ttttcatatc tgttttgggg cctctggggc ttgaatatct     300
gagaaaatat aaacatttca ataatgttct gtggtgagat gagtatgaga gatgtgtcat     360
tcatttgtat caatgaatga atgaggacaa ttagtgtata aatccttagt acaacaatct     420
gagggtaggg gtggtactat tcaatttcta tttataaaga tacttatttc tatttattta     480
tgcttgtgac aaatgttttg ttcgggacca caggaatcac aaagatgagt ctttgaattt     540
aagaagttaa tggtccagga ataattacat agcttacaaa tgactatgat ataccatcaa     600
acaagaggtt ccatgagaaa ataatctgaa aggtttaata agttgtcaaa ggtgagaggg     660
ctcttctcta gctagagact aatcagaaat acattcaggg ataattattt gaatagacct     720
taagggttgg gtacattttg ttcaagcatt gatggagaag gagagtgaat atttgaaaac     780
attttcaact aaccaaccac ccaatccaac aaacaaaaaa tgaaaagaat ctcagaaaca     840
gtgagataag agaaggaatt ttctcacaac ccacacgtat agctcaactg ctctgaagaa     900
gtatatatct aatatttaac actaacatca tgctaataat gataataatt actgtcattt     960
tttaatgtct ataagtacca ggcatttaga agatattatt ccatttatat atcaaaataa    1020
```

FIG. 28*ii*

```
acttgagggg atagatcatt ttcatgatat atgagaaaaa ttaaaaacag attgaattat   1080
ttgcctgtca tacagctaat aattgaccat aagacaatta gatttaaatt agttttgaat   1140
ctttctaata ccaaagttca gtttactgtt ccatgttgct tctgagtggc ttcacagact   1200
tatgaaaaag taaacggaat cagaattaca tcaatgcaaa agcattgctg tgaactctgt   1260
acttaggact aaactttgag caataacaca catagattga ggattgtttg ctgttagcat   1320
acaaactctg gttcaaagct cctctttatt gcttgtcttg gaaaatttgc tgttcttcat   1380
ggtttctctt ttcactgcta tctatttttc tcaaccactc acatggctac aataactgtc   1440
tgcaagctta tgattcccaa atatctatct ctagcctcaa tcttgttcca gaagataaaa   1500
agtagtattc aaatgcacat caacgtctcc acttggaggg cttaaagacg tttcaacata   1560
caaaccgggg agttttgcct ggaatgtttc ctaaaatgtg tcctgtagca catagggtcc   1620
tcttgttcct taaaatctaa ttacttttag cccagtgctc atcccaccta tggggagatg   1680
agagtgaaaa gggagcctga ttaataatta cactaagtca ataggcatag agccaggact   1740
gtttgggtaa actggtcact ttatcttaaa ctaaatatat ccaaaactga acatgtactt   1800
agttactaag tctttgactt tatctcattc ataccactca gctttatcca ggccacttat   1860
ttgacagtat tattgcgaaa acttcctaac tggtctcctt atcatagtct tatccccttt   1920
tgaaacaaaa gagacagttt caaaatacaa atatgatttt tattagctcc cttttgttgt   1980
ctataatagt cccagaagga gttataaact ccatttaaaa agtctttgag atgtggccct   2040
tgccaacttt gccaggaatt cccaatatct agtattttct actattaaac tttgtgcctc   2100
ttcaaaactg cattttctct cattccctaa gtgtgcattg ttttccctta ccggttggtt   2160
```

FIG. 28*iii* tttccaccac cttttacatt ttcctggaac actatacccct ccctcttcat ttggcccacc 2220
tctaattttc tttcagatct ccatgaagat gttacttcct ccaggaagcc ttatctgacc 2280
cctccaaaga tgtcatgagt tcctcttttc attctactaa tcacagcatc catcacacca 2340
tgttgtgatt actgatacta ttgtctgttt ctctgattag gcagtaagct caacaagagc 2400
tacatggtgc ctgtctcttg ttgctgatta ttcccatcca aaaacagtgc ctggaatgca 2460
gacttaacat tttattgaat gaataaataa aaccccatct atcgagtgct actttgtgca 2520
agacccggtt ctgaggcatt tatatttatt gatttattta attctcattt aaccatgaag 2580
gaggtactat cactatcctt attttatagt tgataaagat aaagcccaga gaaatgaatt 2640
aactcaccca aagtcatgta gctaagtgac agggcaaaaa ttcaaaccag ttccccaact 2700
ttacgtgatt aatactgtgc tatactgcct ctctgatcat atggcatgga atgcagacat 2760
ctgctccgta aggcagaata tggaaggaga ttggaggatg acacaaaacc agcataatat 2820
cagaggaaaa gtccaaacag gacctgaact gatagaaaag ttgttactcc tggtgtagtc 2880
gcatcgacat cttgatgaac tggtggctga cacaacatac attggcttga tgtgtacata 2940
ttatttgtag ttgtgtgtgt atttttatat atatatttgt aatattgaaa tagtcataat 3000
ttactaaagg cctaccattt gccaggcatt tttacatttg tcccctctaa tcttttgatg 3060
agatgatcag attggattac ttggccttga agatgatata tctacatcta tatctatatc 3120
tatatctata tctatatcta tatctatatc tatatctata tatgtatatc agaaaagctg 3180
aaatatgttt tgtaaagtta taaagatttc agactttata gaatctggga tttgccaaat 3240
gtaacccctt tctctacatt aaacccatgt tggaacaaat acatttatta ttcattcatc 3300

FIG. 28*iv*

```
aaatgttgct gagtcctggc tatgaaccag acactgtgaa agcctttggg atattttgcc    3360
catgcttggg caagcttata tagtttgctt cataaaactc tatttcagtt cttcataact    3420
aatacttcat gactattgct tttcaggtat tccttcataa caaatacttt ggctttcata    3480
tatttgagta aagtccccct tgaggaagag tagaagaact gcactttgta aatactatcc    3540
tggaatccaa acggatagac aaggatggtg ctacctcttt ctggagagta cgtgagcaag    3600
gcctgttttg ttaacatgtt ccttaggaga caaaacttag gagagacacg catagcagaa    3660
aatggacaaa aactaacaaa tgaatgggaa ttgtacttga ttagcattga agaccttgtt    3720
tatactatga taaatgtttg tatttgctgg aagtgctact gacggtaaac ccttttttgtt    3780
taaatgtgtg ccctagtagc ttgcagtatg atctattttt taagtactgt acttagctta    3840
tttaaaaatt ttatgtttaa aattgcatag tgctctttca ttgaagaagt tttgagagag    3900
agatagaatt aaattcactt atcttaccat ctagagaaac ccaatgttaa aactttgttg    3960
tccattattt ctgtctttta ttcaacattt tttttagagg gtgggaggaa tacagaggag    4020
gtacaatgat acacaaatga gagcactctc catgtattgt tttgtcctgt ttttcagtta    4080
acaatatatt atgagcatat ttccatttca ttaaatattc ttccacaaag ttattttgat    4140
ggctgtatat caccctactt tatgaatgta ccatattaat ttatttcctg gtgtgggtta    4200
tttgatttta taatcttacc tttagaataa tgaaacacct gtgaagcttt agaaaatact    4260
ggtgcctggg tctcaactcc acagattctg atttaactgg tctgggttac agactaggca    4320
ttgggaattc aaaaagttcc cccagtgatt ctaatgtgta gccaagatcg ggaacccttg    4380
tagacaggga tgataggagg tgagccactc ttagcatcca tcatttagta ttaacatcat    4440
```

FIG. 28v

```
catcttgagt tgctaagtga atgatgcacc tgacccactt tataaagaca catgtgcaaa 4500
taaaattatt ataggacttg gtttattagg gcttgtgctc taagttttct atgttaagcc 4560
atacatcgca tactaaatac tttaaaatgt accttattga catacatatt aagtgaaaag 4620
tgtttctgag ctaaacaatg acagcataat tatcaagcaa tgataatttg aaatgaattt 4680
attattctgc aacttaggga caagtcatct ctctgaattt tttgtacttt gagagtattt 4740
gttatatttg caagatgaag agtctgaatt ggtcagacaa tgtcttgtgt gcctggcata 4800
tgataggcat ttaatagttt taaagaatta atgtatttag atgaattgca taccaaatct 4860
gctgtctttt ctttatggct tcattaactt aatttgagag aaattaatta ttctgcaact 4920
tagggacaag tcatgtcttt gaatattctg tagtttgagg agaatatttg ttatatttgc 4980
aaaataaaat aagtttgcaa gttttttttt tctgccccaa agagctctgt gtccttgaac 5040
ataaaataca aataaccgct atgctgttaa ttattggcaa atgtcccatt ttcaacctaa 5100
ggaaatacca taaagtaaca gatataccaa caaaaggtta ctagttaaca ggcattgcct 5160
gaaaagagta taaaagaatt tcagcatgat tttccatatt gtgcttccac cactgccaat 5220
aaca                                                              5224
```

293 cells

CV790

CV733

SEQUENCE LISTING

```
<160> NUMBER OF SEQ ID NOS: 23

<210> SEQ ID NO 1
<211> LENGTH: 26
<212> TYPE: DNA
<213> ORGANISM: Artificial Sequence
<220> FEATURE:
<223> OTHER INFORMATION: Synthetic construct
```

-continued

<400> SEQUENCE: 1
tatcggccgg cattgctgtg aactct 26

<210> SEQ ID NO 2
<211> LENGTH: 26
<212> TYPE: DNA
<213> ORGANISM: Artificial Sequence
<220> FEATURE:
<223> OTHER INFORMATION: Synthetic construct

<400> SEQUENCE: 2
ttacggccgc tttgttattg gcagtg 26

<210> SEQ ID NO 3
<211> LENGTH: 31
<212> TYPE: DNA
<213> ORGANISM: Artificial Sequence
<220> FEATURE:
<223> OTHER INFORMATION: Synthetic construct

<400> SEQUENCE: 3
gatctcgaga cccgggaccc tgctgggttt c 31

<210> SEQ ID NO 4
<211> LENGTH: 33
<212> TYPE: DNA
<213> ORGANISM: Artificial Sequence
<220> FEATURE:
<223> OTHER INFORMATION: Synthetic construct

<400> SEQUENCE: 4
gatcaccggt gcttgagttc caggaacgtt ttg 33

<210> SEQ ID NO 5
<211> LENGTH: 36
<212> TYPE: DNA
<213> ORGANISM: Artificial Sequence
<220> FEATURE:
<223> OTHER INFORMATION: Synthetic construct

<400> SEQUENCE: 5
gatcaaccgg taccgacttc tgtagctttg ggaagg 36

<210> SEQ ID NO 6
<211> LENGTH: 34
<212> TYPE: DNA
<213> ORGANISM: Artificial Sequence
<220> FEATURE:
<223> OTHER INFORMATION: Synthetic construct

<400> SEQUENCE: 6
gatcctcgag cccgggttca agcaattctc ctgc 34

<210> SEQ ID NO 7
<211> LENGTH: 67
<212> TYPE: DNA
<213> ORGANISM: Rattus rattus

<400> SEQUENCE: 7
ccccgaggca gtgcatgagg ctcagggcgt gcgtgagtcg cagcgagacc ccggggtgca 60
ggccgga 67

<210> SEQ ID NO 8

-continued

<211> LENGTH: 1519
<212> TYPE: DNA
<213> ORGANISM: Homo Sapien

<400> SEQUENCE: 8
gggcccaaaa ttagcaagtg accacgtggt tctgaagcca gtggcctaag gaccaccctt 60
gcagaaccgt ggtctccttg tcacagtcta ggcagcctct ggcttagcct ctgtttcttt 120
cataaccttt ctcagcgcct gctctgggcc agaccagtgt tgggaggagt cgctactgag 180
ctcctagatt ggcaggggag gcagatggag aaaaggagtg tgtgtggtca gcattggagc 240
agaggcagca gtgggcaata gaggaagtga gtaaatcctt gggagggctc cctagaagtg 300
atgtgttttc tttttttgtt ttagagacag gatctcgctc tgtcgcccag gctggtgtgc 360
agtggcatga tcatagctca ctgcagcctc gacttctcgg gctcaagcaa tcctcccacc 420
tcagcctccc aagtagctgg gactacgggc acacgccacc atgcctggct aatttttgta 480
ttttttgtag agatgggtct tcaccatgtt gatcaggctg gtctcgaact cctgggctca 540
tgcgatccac ccgccagct gattacaggg attccggtgg tgagccaccg cgcccagacg 600
ccacttcatc gtattgtaaa cgtctgttac ctttctgttc ccctgtctac tggactgtga 660
gctccttagg gccacgaatt gaggatgggg cacagagcaa gctctccaaa cgtttgttga 720
atgagtgagg gaatgaatga gttcaagcag atgctatacg ttggctgttg gagattttgg 780
ctaaaatggg acttgcagga aagcccgacg tccccctcgc catttccagg caccgctctt 840
cagcttgggc tctgggtgag cgggataggg ctgggtgcag gattaggata atgtcatggg 900
tgaggcaagt tgaggatgga agaggtggct gatggctggg ctgtggaact gatgatcctg 960
aaaagaagag gggacagtct ctggaaatct aagctgaggc tgttgggggc tacaggttga 1020
gggtcacgtg cagaagagag gctctgttct gaacctgcac tatagaaagg tcagtgggat 1080
gcgggagcgt cggggcgggg cggggcctat gttcccgtgt ccccacgcct ccagcagggg 1140
acgcccgggc tgggggcggg gagtcagacc gcgcctggta ccatccggac aaagcctgcg 1200
cgcgccccgc cccgccattg gccgtaccgc cccgcgccgc cgccccatcc cgcccctcgc 1260
cgccgggtcc ggcgcgttaa agccaatagg aaccgccgcc gttgttcccg tcacggacgg 1320
ggcagccaat tgtggcggcg ctcggcggct cgtggctctt tcgcggcaaa aaggatttgg 1380
cgcgtaaaag tggccgggac tttgcaggca gcggcggccg gggcggagc gggatcgagc 1440 cctcgccgag gcctgccgcc atgggcccgc gccgccgccg ccgcctgtca cccgggccgc 1500
gcgggccgtg agcgtcatg 1519

<210> SEQ ID NO 9
<211> LENGTH: 5836
<212> TYPE: DNA
<213> ORGANISM: Homo Sapien

<400> SEQUENCE: 9
aagcttctag ttttcttttc ccggtgacat cgtggaaagc actagcatct ctaagcaatg 60
atctgtgaca atattcacag tgtaatgcca tccagggaac tcaactgagc cttgatgtcc 120
agagattttt gtgttttttt ctgagactga gtctcgctct gtgccaggct ggagtgcagt 180
ggtgcaacct tggctcactg caagctccgc ctcctgggtt cacgccattc tcctgcctca 240
gcctcctgag tagctgggac tacaggcacc cgccaccacg cctggctaat ttttttgtat 300
ttttagtaga gatggggttt cactgtgtta gccaggatgg tctcagtctc ctgacctcgt 360
gatctgccca ccttggcctc ccaaagtgct gggatgacag gcgtgagcca ccgcgcctgg 420

-continued

```
ccgatatcca gagatttttt gggggctcc atcacacaga catgttgact gtcttcatgg    480
ttgactttta gtatccagcc cctctagaaa tctagctgat atagtgtggc tcaaaacctt    540
cagcacaaat cacaccgtta gactatctgg tgtggcccaa accttcaggt gaacaaaggg    600
actctaatct ggcaggatat tccaaagcat tagagatgac ctcttgcaaa gaaaaagaaa    660
tggaaaagaa aaagaaagaa aggaaaaaaa aaaaaaaaaa gagatgacct ctcaggctct    720
gaggggaaac gcctgaggtc tttgagcaag gtcagtcctc tgttgcacag tctccctcac    780
agggtcattg tgacgatcaa atgtggtcac gtgtatgagg caccagcaca tgcctggctc    840
tggggagtgc cgtgtaagtg tatgcttgca ctgctgaatg cttgggatgt gtcagggatt    900
atcttcagca cttacagatg ctcatctcat cctcacagca tcactatggg atgggtatta    960
ctggcctcat ttgatggaga aagtggctgt ggctcagaaa gggggacca ctagaccagg   1020
gacactctgg atgctgggga ctccagagac catgaccact caccaactgc agagaaatta   1080
attgtggcct gatgtccctg tcctggagag ggtggaggtg gaccttcact aacctcctac   1140
cttgaccctc tcttttaggg ctctttctga cctccaccat ggtactagga ccccattgta   1200
ttctgtaccc tcttgactct atgaccccca ctgcccactg catccagctg ggtcccctcc   1260
tatctctatt cccagctggc cagtgcagtc tcagtgccca cctgtttgtc agtaactctg   1320
aaggggctga cattttactg acttgcaaac aaataagcta actttccaga gttttgtgaa   1380
tgctggcaga gtccatgaga ctcctgagtc agaggcaaag gcttttactg ctcacagctt   1440
agcagacagc atgaggttca tgttcacatt agtacacctt gcccccccca aatcttgtag   1500
ggtgaccaga gcagtctagg tggatgctgt gcagaagggg tttgtgccac tggtgagaaa   1560
cctgagatta ggaatcctca atcttatact gggacaactt gcaaacctgc tcagcctttg   1620
tctctgatga agatattatc ttcatgatct tggattgaaa acagacctac tctggaggaa   1680
catattgtat cgattgtcct tgacagtaaa caaatctgtt gtaagagaca ttatctttat   1740
tatctaggac agtaagcaag cctggatctg agagagatat catcttgcaa ggatgcctgc   1800
tttacaaaca tccttgaaac aacaatccag aaaaaaaaag gtgttgctgt ctttgctcag   1860
aagacacaca gatacgtgac agaaccatgg agaattgcct cccaacgctg ttcagccaga   1920
gccttccacc cttgtctgca ggacagtctc aacgttccac cattaaatac ttcttctatc   1980
acatcctgct tctttatgcc taaccaaggt tctaggtccc gatcgactgt gtctggcagc   2040
actccactgc caaacccaga ataaggcagc gctcaggatc ccgaaggggc atggctgggg   2100
atcagaactt ctgggtttga gtgaggagtg ggtccaccct cttgaatttc aaaggaggaa   2160
gaggctggat gtgaaggtac tgggggaggg aaagtgtcag ttccgaactc ttaggtcaat   2220
gagggaggag actggtaagg tcccagctcc cgaggtactg atgtgggaat ggcctaagaa   2280
tctcatatcc tcaggaagaa ggtgctggaa ttctgagggg tagagttctg ggtatatttg   2340
tggcttaagg ctctttggcc cctgaaggca gaggctggaa ccattaggtc cagggtttgg   2400
ggtgatagta atgggatctc ttgattcctc aagagtctga ggatcgaggg ttgcccattc   2460
ttccatcttg ccacctaatc cttactccac ttgagggtat caccagccct tctagctcca   2520
tgaaggtccc ctgggcaagc acaatctgag catgaaagat gccccagagg ccttgggtgt   2580
catccactca tcatccagca tcacactctg agggtgtggc cagcaccatg acgtcatgtt   2640
gctgtgacta tccctgcacc gtgcctctcc agccacctgc caaccgtaga gctgcccatc   2700
ctcctctggt gggagtggcc tgcatggtgc caggctgagg cctagtgtca gacagggagc   2760
```

-continued

```
ctggaatcat agggatccag gactcaaaag tgctagagaa tggccatatg tcaccatcca   2820
tgaaatctca aaggcttctg ggtggagggc acagggacct gaacttatgg tttcccaagt   2880
ctattgctct cccaagtgag tctcccagat acgaggcact gtgccagcat cagccttatc   2940
tccaccacat cttgtaaaag gactacccag ggccctgatg aacaccatgg tgtgtacagg   3000
agtagggggt ggaggcacgg actcctgtga ggtcacagcc aagggagcat catcatgggt   3060
ggggaggagg caatggacag gcttgagaac ggggatgtgg ttgtatttgg ttttctttgg   3120
ttagataaag tactgggtat aggattgaga gtggagtatg aagaccagtt aggatggagg   3180
atcagattgg agttgggtta gataaagtgc tgggtatagg attgagagtg gagtatgaag   3240
accagttagg atagaggatc agattggagt tgggttagag atggggtaaa attgtgctcc   3300
ggatgagttt gggattgaca ctgtggaggt ggtttgggat ggcatggctt tgggatggaa   3360
atagatttgt tttgatgttg gctcagacat ccttggggar tgaactgggg atgaagctgg   3420
gtttgatttt ggaggtagaa gacgtggaag tagctgtcag atttgacagt ggccatgagt   3480
tttgtttgat ggggaatcaa acaatggggg aagacataag ggttggcttg ttaggttaag   3540
ttgcgttggg ttgatggggt cggggctgtg tataatgcag ttggattggt ttgtattaaa   3600
ttgggttggg tcaggttttg gttgaggatg agttgaggat atgcttgggg acaccggatc   3660
catgaggttc tcactggagt ggagacaaac ttcctttcca ggatgaatcc agggaagcct   3720
taattcacgt gtaggggagg tcaggccact ggctaagtat atccttccac tccagctcta   3780
agatggtctt aaattgtgat tatctatatc cacttctgtc tccctcactg tgcttggagt   3840
ttacctgatc actcaactag aaacagggga agattttatc aaattctttt tttttttttt   3900
ttttttttga gacagagtct cactctgttg cccaggctgg agtgcagtgg cgcagtctcg   3960
gctcactgca acctctgcct cccaggttca agtgattctc ctgcctcagc ctcctgagtt   4020
gctgggatta caggcatgca gcaccatgcc cagctaattt ttgtattttt agtagagatg   4080
gggtttcacc aatgtttgcc aggctggcct cgaactcctg acctggtgat ccacctgcct   4140
cagcctccca aagtgctggg attacaggcg tcagccaccg cgcccagcca cttttgtcaa   4200
attcttgaga cacagctcgg gctggatcaa gtgagctact ctggttttat tgaacagctg   4260
aaataaccaa ctttttggaa attgatgaaa tcttacggag ttaacagtgg aggtaccagg   4320
gctcttaaga gttcccgatt ctcttctgag actacaaatt gtgattttgc atgccacctt   4380
aatctttttt tttttttttt taaatcgagg tttcagtctc attctatttc ccaggctgga   4440
gttcaatagc gtgatcacag ctcactgtag ccttgaactc ctggccttaa gagattctcc   4500
tgcttcggtc tcccaatagc taagactaca gtagtccacc accatatcca gataattttt   4560
aaattttttg gggggccggg cacagtggct cacgcctgta atcccaacac catgggaggc   4620
tgagatgggt ggatcacgag gtcaggagtt tgagaccagc ctgaccaaca tggtgaaact   4680
ctgtctctac taaaaaaaaa aaaaatagaa aaattagccg ggcgtggtgg cacacggcac   4740
ctgtaatccc agctactgag gaggctgagg caggagaatc acttgaaccc agaaggcaga   4800
ggttgcaatg agccgagatt gcgccactgc actccagcct gggtgacaga gtgagactct   4860
gtctcaaaaa aaaaaaattt tttttttttt tttgtagaga tggatcttgc tttgtttctc   4920
tggttggcct tgaactcctg gcttcaagtg atcctcctac cttggcctcg gaaagtgttg   4980
ggattacagg cgtgagccac catgactgac ctgtcgttaa tcttgaggta cataaacctg   5040
gctcctaaag gctaaaggct aaatatttgt tggagaaggg gcattggatt ttgcatgagg   5100
atgattctga cctgggaggg caggtcagca ggcatctctg ttgcacagat agagtgtaca   5160
```

-continued ggtctggaga acaaggagtg gggggttatt ggaattccac attgtttgct gcacgttgga 5220
ttttgaaatg ctagggaact ttgggagact catatttctg ggctagagga tctgtggacc 5280
acaagatctt tttatgatga cagtagcaat gtatctgtgg agctggattc tgggttggga 5340
gtgcaaggaa aagaatgtac taaatgccaa gacatctatt tcaggagcat gaggaataaa 5400
agttctagtt tctggtctca gagtggtgca gggatcaggg agtctcacaa tctcctgagt 5460
gctggtctct tagggcacac tgggtcttgg agtgcaaagg atctaggcac gtgaggcttt 5520
gtatgaagaa tcggggatcg tacccacccc ctgtttctgt ttcatcctgg gcatgtctcc 5580
tctgcctttg tcccctagat gaagtctcca tgagctacaa gggcctggtg catccagggt 5640
gatctagtaa ttgcagaaca gcaagtgcta gctctccctc cccttccaca gctctgggtg 5700
tgggaggggg ttgtccagcc tccagcagca tggggagggc cttggtcagc ctctgggtgc 5760
cagcagggca ggggcggagt cctggggaat gaaggtttta tagggctcct gggggaggct 5820
ccccagcccc aagctt 5836

<210> SEQ ID NO 10
<211> LENGTH: 15056
<212> TYPE: DNA
<213> ORGANISM: Homo Sapien

<400> SEQUENCE: 10
aagcttttta gtgctttaga cagtgagctg gtctgtctaa cccaagtgac ctgggctcca 60
tactcagccc cagaagtgaa gggtgaagct gggtggagcc aaaccaggca agcctaccct 120
cagggctccc agtggcctga gaaccattgg acccaggacc cattacttct agggtaagga 180
aggtacaaac accagatcca accatggtct gggggacag ctgtcaaatg cctaaaaata 240
tacctgggag aggagcaggc aaactatcac tgccccaggt tctctgaaca gaaacagagg 300
ggcaacccaa agtccaaatc caggtgagca ggtgcaccaa atgcccagag atatgacgag 360
gcaagaagtg aaggaaccac ccctgcatca aatgttttgc atgggaagga gaagggggtt 420
gctcatgttc ccaatccagg agaatgcatt tgggatctgc cttcttctca ctccttggtt 480
agcaagacta agcaaccagg actctggatt tggggaaaga cgtttatttg tggaggccag 540
tgatgacaat cccacgaggg cctaggtgaa gagggcagga aggctcgaga cactggggac 600
tgagtgaaaa ccacacccat gatctgcacc acccatggat gctccttcat tgctcacctt 660
tctgttgata tcagatggcc ccattttctg taccttcaca gaaggacaca ggctagggtc 720
tgtgcatggc cttcatcccc ggggccatgt gaggacagca ggtgggaaag atcatgggtc 780
ctcctgggtc ctgcagggcc agaacattca tcacccatac tgacctccta gatgggaatg 840
gcttccctgg ggctgggcca acggggcctg ggcaggggag aaaggacgtc aggggacagg 900
gaggaagggt catcgagacc cagcctggaa ggttcttgtc tctgaccatc caggatttac 960
ttccctgcat ctacctttgg tcattttccc tcagcaatga ccagctctgc ttcctgatct 1020
cagcctccca ccctggacac agcaccccag tccctggccc ggctgcatcc acccaatacc 1080
ctgataaccc aggacccatt acttctaggg taaggagggt ccaggagaca gaagctgagg 1140
aaaggtctga agaagtcaca tctgtcctgg ccagagggga aaaaccatca gatgctgaac 1200
caggagaatg ttgacccagg aaagggaccg aggacccaag aaaggagtca gaccaccagg 1260
gtttgcctga gaggaaggat caaggccccg agggaaagca gggctggctg catgtgcagg 1320
acactggtgg ggcatatgtg tcttagattc tccctgaatt cagtgtccct gccatggcca 1380

-continued

```
gactctctac tcaggcctgg acatgctgaa ataggacaat ggccttgtcc tctctcccca   1440
ccatttggca agagacataa aggacattcc aggacatgcc ttcctgggag gtccaggttc   1500
tctgtctcac acctcaggga ctgtagttac tgcatcagcc atggtaggtg ctgatctcac   1560
ccagcctgtc caggcccttc cactctccac tttgtgacca tgtccaggac cacccctcag   1620
atcctgagcc tgcaaatacc cccttgctgg gtgggtggat tcagtaaaca gtgagctcct   1680
atccagcccc cagagccacc tctgtcacct tcctgctggg catcatccca ccttcacaag   1740
cactaaagag catggggaga cctggctagc tgggtttctg catcacaaag aaaataatcc   1800
cccaggttcg gattcccagg gctctgtatg tggagctgac agacctgagg ccaggagata   1860
gcagaggtca gccctaggga gggtgggtca tccacccagg ggacaggggt gcaccagcct   1920
tgctactgaa agggcctccc caggacagcg ccatcagccc tgcctgagag ctttgctaaa   1980
cagcagtcag aggaggccat ggcagtggct gagctcctgc tccaggcccc aacagaccag   2040
accaacagca caatgcagtc cttccccaac gtcacaggtc accaaaggga aactgaggtg   2100
ctacctaacc ttagagccat caggggagat aacagcccaa tttcccaaac aggccagttt   2160
caatcccatg acaatgacct ctctgctctc attcttccca aaataggacg ctgattctcc   2220
cccaccatgg atttctccct tgtcccggga gccttttctg ccccctatga tctgggcact   2280
cctgacacac acctcctctc tggtgacata tcagggtccc tcactgtcaa gcagtccaga   2340
aaggacagaa ccttggacag cgcccatctc agcttcaccc ttcctccttc acagggttca   2400
gggcaaagaa taaatggcag aggccagtga gcccagagat ggtgacaggc agtgacccag   2460
gggcagatgc ctggagcagg agctggcggg gccacaggga gaaggtgatg caggaaggga   2520
aacccagaaa tgggcaggaa aggaggacac aggctctgtg gggctgcagc ccagggttgg   2580
actatgagtg tgaagccatc tcagcaagta aggccaggtc ccatgaacaa gagtgggagc   2640
acgtggcttc ctgctctgta tatggggtgg gggattccat gccccataga accagatggc   2700
cggggttcag atggagaagg agcaggacag gggatcccca ggataggagg accccagtgt   2760
ccccacccag gcaggtgact gatgaatggg catgcagggt cctcctgggc tgggctctcc   2820
ctttgtccct caggattcct tgaaggaaca tccggaagcc gaccacatct acctggtggg   2880
ttctggggag tccatgtaaa gccaggagct tgtgttgcta ggaggggtca tggcatgtgc   2940
tgggggcacc aaagagagaa acctgagggc aggcaggacc tggtctgagg aggcatggga   3000
gcccagatgg ggagatggat gtcaggaaag gctgccccat cagggagggt gatagcaatg   3060
gggggtctgt gggagtgggc acgtgggatt ccctgggctc tgccaagttc cctcccatag   3120
tcacaacctg ggacactgc ccatgaaggg gcgcctttgc ccagccagat gctgctggtt   3180
ctgcccatcc actaccctct ctgctccagc cactctgggt ctttctccag atgccctgga   3240
cagccctggc ctgggcctgt cccctgagag gtgttgggag aagctgagtc tctggggaca   3300
ctctcatcag agtctgaaag gcacatcagg aaacatccct ggtctccagg actaggcaat   3360
gaggaaaggg ccccagctcc tccctttgcc actgagaggg tcgaccctgg gtggccacag   3420
tgacttctgc gtctgtccca gtcaccctga aaccacaaca aaaccccagc cccagaccct   3480
gcaggtacaa tacatgtggg gacagtctgt acccagggga agccagttct ctcttcctag   3540
gagaccgggc ctcagggctg tgcccggggc aggcgggggc agcacgtgcc tgtccttgag   3600
aactcgggac cttaagggtc tctgctctgt gaggcacagc aaggatcctt ctgtccagag   3660
atgaaagcag ctcctgcccc tcctctgacc tcttcctcct tcccaaatct caaccaacaa   3720
ataggtgttt caaatctcat catcaaatct tcatccatcc acatgagaaa gcttaaaacc   3780
```

-continued

```
caatggattg acaacatcaa gagttggaac aagtggacat ggagatgtta cttgtggaaa   3840
tttagatgtg ttcagctatc gggcaggaga atctgtgtca aattccagca tggttcagaa   3900
gaatcaaaaa gtgtcacagt ccaaatgtgc aacagtgcag gggataaaac tgtggtgcat   3960
tcaaactgag ggatattttg gaacatgaga aaggaaggga ttgctgctgc acagaacatg   4020
gatgatctca cacatagagt tgaaagaaag gagtcaatcg cagaatagaa aatgatcact   4080
aattccacct ctataaagtt tccaagagga aaacccaatt ctgctgctag agatcagaat   4140
ggaggtgacc tgtgccttgc aatggctgtg agggtcacgg gagtgtcact tagtgcaggc   4200
aatgtgccgt atcttaatct gggcagggct ttcatgagca cataggaatg cagacattac   4260
tgctgtgttc attttacttc accggaaaag aagaataaaa tcagccgggc gcggtggctc   4320
acgcctgtaa tcccagcact ttagaaggct gaggtgggca gattacttga ggtcaggagt   4380
tcaagaccac cctggccaat atggtgaaac cccggctcta ctaaaaatac aaaaattagc   4440
tgggcatggt ggtgcgcgcc tgtaatccca gctactcggg aggctgaggc tggacaattg   4500
cttggaccca ggaagcagag gttgcagtga gccaagattg tgccactgca ctccagcttg   4560
ggcaacagag ccagactctg taaaaaaaaa aaaaaaaaaa aaaaaaagaa agaaagaaaa   4620
agaaaagaaa gtataaaatc tctttgggtt aacaaaaaaa gatccacaaa acaaacacca   4680
gctcttatca aacttacaca actctgccag agaacaggaa acacaaatac tcattaactc   4740
acttttgtgg caataaaacc ttcatgtcaa aaggagacca ggacacaatg aggaagtaaa   4800
actgcaggcc ctacttgggt gcagagaggg aaaatccaca aataaaacat taccagaagg   4860
agctaagatt tactgcattg agttcattcc ccaggtatgc aaggtgattt taacacctga   4920
aaatcaatca ttgcctttac tacatagaca gattagctag aaaaaaatta caactagcag   4980
aacagaagca atttggcctt cctaaaattc cacatcatat catcatgatg gagacagtgc   5040
agacgccaat gacaataaaa agagggacct ccgtcacccg gtaaacatgt ccacacagct   5100
ccagcaagca cccgtcttcc cagtgaatca ctgtaacctc ccctttaatc agccccaggc   5160
aaggctgcct gcgatggcca cacaggctcc aacccgtggg cctcaacctc ccgcagaggc   5220
tctcctttgg ccaccccatg ggagagcat gaggacaggg cagagccctc tgatgcccac    5280
acatggcagg agctgacgcc agagccatgg gggctggaga gcagagctgc tggggtcaga   5340
gcttcctgag gacacccagg cctaagggaa ggcagctccc tggatggggg caaccaggct   5400
ccgggctcca acctcagagc ccgcatggga ggagccagca ctctaggcct ttcctagggt   5460
gactctgagg ggaccctgac acgacaggat cgctgaatgc acccgagatg aaggggccac   5520
cacgggaccc tgctctcgtg gcagatcagg agagagtggg acaccatgcc aggcccccat   5580
ggcatggctg cgactgaccc aggccactcc cctgcatgca tcagcctcgg taagtcacat   5640
gaccaagccc aggaccaatg tggaaggaag gaaacagcat ccccttttagt gatggaaccc  5700
aaggtcagtg caaagagagg ccatgagcag ttaggaaggg tggtccaacc tacagcacaa   5760
accatcatct atcataagta gaagccctgc tccatgaccc ctgcatttaa ataaacgttt   5820
gttaaatgag tcaaattccc tcaccatgag agctcacctg tgtgtaggcc catcacacac   5880
acaaacacac acacacacac acacacacac acacacacac acagggaaag tgcaggatcc   5940
tggacagcac caggcaggct tcacaggcag agcaaacagc gtgaatgacc catgcagtgc   6000
cctgggcccc atcagctcag agaccctgtg agggctgaga tggggctagg caggggagag   6060
acttagagag ggtggggcct ccagggaggg ggctgcaggg agctgggtac tgccctccag   6120
```

-continued

```
ggagggggct gcagggagct gggtactgcc ctccagggag ggggctgcag ggagctgggt   6180
actgccctcc agggaggggg ctgcagggag ctgggtactg ccctccaggg agggggctgc   6240
agggagctgg gtactgccct ccagggaggc aggagcactg ttcccaacag agagcacatc   6300
ttcctgcagc agctgcacag acacaggagc cccccatgact gccctgggcc agggtgtgga   6360
ttccaaattt cgtgccccat tgggtgggac ggaggttgac cgtgacatcc aaggggcatc   6420
tgtgattcca aacttaaact actgtgccta caaaatagga aataacccta ctttttctac   6480
tatctcaaat tccctaagca caagctagca ccctttaaat caggaagttc agtcactcct   6540
ggggtcctcc catgccccca gtctgacttg caggtgcaca gggtggctga catctgtcct   6600
tgctcctcct cttggctcaa ctgccgcccc tcctgggggt gactgatggt caggacaagg   6660
gatcctagag ctggccccat gattgacagg aaggcaggac ttggcctcca ttctgaagac   6720
taggggtgtc aagagagctg ggcatcccac agagctgcac aagatgacgc ggacagaggg   6780
tgacacaggg ctcagggctt cagacgggtc gggaggctca gctgagagtt cagggacaga   6840
cctgaggagc ctcagtggga aaagaagcac tgaagtggga agttctggaa tgttctggac   6900
aagcctgagt gctctaagga aatgctccca ccccgatgta gcctgcagca ctggacggtc   6960
tgtgtacctc cccgctgccc atcctctcac agcccccgcc tctagggaca caactcctgc   7020
cctaacatgc atctttcctg tctcattcca cacaaaaggg cctctggggt ccctgttctg   7080
cattgcaagg agtggaggtc acgttcccac agaccaccca gcaacagggt cctatggagg   7140
tgcggtcagg aggatcacac gtccccccat gcccagggga ctgactctgg gggtgatgga   7200
ttggcctgga ggccactggt cccctctgtc cctgagggga atctgcaccc tggaggctgc   7260
cacatccctc ctgattcttt cagctgaggg cccttcttga aatcccaggg aggactcaac   7320
ccccactggg aaaggcccag tgtggacggt tccacagcag cccagctaag gcccttggac   7380
acagatcctg agtgagagaa cctttaggga cacaggtgca cggccatgtc cccagtgccc   7440
acacagagca ggggcatctg gaccctgagt gtgtagctcc cgcgactgaa cccagccctt   7500
ccccaatgac gtgaccctg gggtggctcc aggtctccag tccatgccac caaaatctcc   7560
agattgaggg tcctcccttg agtccctgat gcctgtccag gagctgcccc ctgagcaaat   7620
ctagagtgca gagggctggg attgtggcag taaaagcagc cacatttgtc tcaggaagga   7680
aagggaggac atgagctcca ggaagggcga tggcgtcctc tagtgggcgc ctcctgttaa   7740
tgagcaaaaa ggggccagga gagttgagag atcagggctg gccttggact aaggctcaga   7800
tggagaggac tgaggtgcaa agagggggct gaagtagggg agtggtcggg agagatggga   7860
ggagcaggta aggggaagcc ccagggaggc cgggggaggg tacagcagag ctctccactc   7920
ctcagcattg acatttgggg tggtcgtgct agtggggttc tgtaagttgt agggtgttca   7980
gcaccatctg ggactctac ccactaaatg ccagcaggac tccctcccca agctctaaca   8040
accaacaatg tctccagact ttccaaatgt cccctggaga gcaaaattgc ttctggcaga   8100
atcactgatc tacgtcagtc tctaaaagtg actcatcagc gaaatccttc acctcttggg   8160
agaagaatca caagtgtgag aggggtagaa actgcagact tcaaaatctt tccaaaagag   8220
ttttacttaa tcagcagttt gatgtcccag gagaagatac atttagagtg tttagagttg   8280
atgccacatg gctgcctgta cctcacagca ggagcagagt gggttttcca agggcctgta   8340
accacaactg gaatgacact cactgggtta cattacaaag tggaatgtgg ggaattctgt   8400
agactttggg aagggaaatg tatgacgtga gcccacagcc taaggcagtg gacagtccac   8460
tttgaggctc tcaccatcta ggagacatct cagccatgaa catagccaca tctgtcatta   8520
```

-continued

```
gaaaacatgt tttattaaga ggaaaaatct aggctagaag tgctttatgc tctttttttct   8580
ctttatgttc aaattcatat acttttagat cattccttaa agaagaatct atccccctaa   8640
gtaaatgtta tcactgactg gatagtgttg gtgtctcact cccaacccct gtgtggtgac   8700
agtgccctgc ttccccagcc ctgggccctc tctgattcct gagagctttg ggtgctcctt   8760
cattaggagg aagagaggaa gggtgttttt aatattctca ccattcaccc atccacctct   8820
tagacactgg gaagaatcag ttgcccactc ttggatttga tcctcgaatt aatgacctct   8880
atttctgtcc cttgtccatt tcaacaatgt gacaggccta agaggtgcct tctccatgtg   8940
atttttgagg agaaggttct caagataagt tttctcacac ctctttgaat tacctccacc   9000
tgtgtcccca tcaccattac cagcagcatt tggacccttt ttctgttagt cagatgcttt   9060
ccacctcttg agggtgtata ctgtatgctc tctacacagg aatatgcaga ggaaatagaa   9120
aaagggaaat cgcattacta ttcagagaga agaagacctt tatgtgaatg aatgagagtc   9180
taaaatccta agagagccca tataaaatta ttaccagtgc taaaactaca aaagttacac   9240
taacagtaaa ctagaataat aaaacatgca tcacagttgc tggtaaagct aaatcagata   9300
ttttttttctt agaaaaagca ttccatgtgt gttgcagtga tgacaggagt gcccttcagt   9360
caatatgctg cctgtaattt ttgttccctg gcagaatgta ttgtcttttc tccctttaaa   9420
tcttaaatgc aaaactaaag gcagctcctg ggcccccctcc ccaaactcag ctgcctgcaa   9480
ccagccccac gaagagcaga ggcctgagct tccctggtca aaatacgggg ctagggagct   9540
taaccttgct cgataaagct gtgttcccag aatgtcgctc ctgttcccag gggcaccagc   9600
ctggagggtg gtgagcctca ctggtggcct gatgcttacc ttgtgccctc acaccagtgg   9660
tcactggaac cttgaacact tggctgtcgc ccggatctgc agatgtcaag aacttctgga   9720
agtcaaatta ctgcccactt ctccagggca gatacctgtg aacatccaaa accatgccac   9780
agaaccctgc ctggggtcta caacacatat ggactgtgag caccaagtcc agccctgaat   9840
ctgtgaccac ctgccaagat gcccctaact gggatccacc aatcactgca catggcaggc   9900
agcgaggctt ggaggtgctt cgccacaagg cagccccaat ttgctgggag tttcttggca   9960
cctggtagtg gtgaggagcc ttgggaccct caggattact cccccttaagc atagtgggga  10020
cccttctgca tccccagcag gtgccccgct cttcagagcc tctctctctg aggtttaccc  10080
agacccctgc accaatgaga ccatgctgaa gcctcagaga gagagatgga gctttgacca  10140
ggagccgctc ttccttgagg gccagggcag ggaaagcagg aggcaccacc aggagtggga  10200
acaccagtgt ctaacgccct gatgagaaca gggtggtctc tcccatatgc ccataccagg  10260
cctgtgaaca gaatcctcct tctgcagtga caatgtctga gaggacgaca tgtttcccag  10320
cctaacgtgc agccatgccc atctacccac tgcctactgc aggacagcac caacccagga  10380
gctgggaagc tgggagaaga catggaatac ccatggcttc tcaccttcct ccagtccagt  10440
gggcaccatt tatgcctagg acacccacct gccggcccca ggctcttaag agttaggtca  10500
cctaggtgcc tctgggaggc cgaggcagga gaattgcttg aacccgggag gcagaggttg  10560
cagtgagccg agatcacacc actgcactcc agcctgggtg acagaatgag actctgtctc  10620
aaaaaaaaag agaaagatag catcagtggc taccaagggc taggggcagg ggaaggtgga  10680
gagttaatga ttaatagtat gaagtttcta tgtgagatga tgaaaatgtt ctggaaaaaa  10740
aaatatagtg gtgaggatgt agaatattgt gaatataatt aacggcattt aattgtacac  10800
ttaacatgat taatgtggca tattttatct tatgtatttg actacatcca agaaacactg  10860
```

-continued

```
ggagagggaa agcccaccat gtaaaataca cccaccctaa tcagatagtc ctcattgtac  10920
ccaggtacag gcccctcatg acctgcacag gaataactaa ggatttaagg acatgaggct  10980
tcccagccaa ctgcaggtgc acaacataaa tgtatctgca aacagactga gagtaaagct  11040
gggggcacaa acctcagcac tgccaggaca cacacccttc tcgtggattc tgactttatc  11100
tgacccggcc cactgtccag atcttgttgt gggattggga caagggaggt cataaagcct  11160
gtccccaggg cactctgtgt gagcacacga gacctcccca cccccccacc gttaggtctc  11220
cacacataga tctgaccatt aggcattgtg aggaggactc tagcgcgggc tcagggatca  11280
caccagagaa tcaggtacag agaggaagac ggggctcgag gagctgatgg atgacacaga  11340
gcagggttcc tgcagtccac aggtccagct caccctggtg taggtgcccc atccccctga  11400
tccaggcatc cctgacacag ctccctcccg gagcctcctc ccaggtgaca catcagggtc  11460
cctcactcaa gctgtccaga gagggcagca ccttggacag cgcccacccc acttcactct  11520
tcctccctca cagggctcag ggctcagggc tcaagtctca gaacaaatgg cagaggccag  11580
tgagcccaga gatggtgaca gggcaatgat ccaggggcag ctgcctgaaa cgggagcagg  11640
tgaagccaca gatgggagaa gatggttcag gaagaaaaat ccaggaatgg gcaggagagg  11700
agaggaggac acaggctctg tggggctgca gcccaggatg ggactaagtg tgaagacatc  11760
tcagcaggtg aggccaggtc ccatgaacag agaagcagct cccacctccc ctgatgcacg  11820
gacacacaga gtgtgtggtg ctgtgccccc agagtcgggc tctcctgttc tggtccccag  11880
ggagtgagaa gtgaggttga cttgtccctg ctcctctctg ctaccccaac attcaccttc  11940
tcctcatgcc cctctctctc aaatatgatt tggatctatg tccccgccca aatctcatgt  12000
caaattgtaa accccaatgt tggaggtggg gccttgtgag aagtgattgg ataatgcggg  12060
tggattttct gctttgatgc tgtttctgtg atagagatct cacatgatct ggttgtttaa  12120
aagtgtgtag cacctctccc ctctctctct ctctctctta ctcatgctct gccatgtaag  12180
acgttcctgt ttccccttca ccgtccagaa tgattgtaag ttttctgagg cctccccagg  12240
agcagaagcc actatgcttc ctgtacaact gcagaatgat gagcgaatta aacctctttt  12300
ctttataaat tacccagtct caggtatttc tttatagcaa tgcgaggaca gactaataca  12360
atcttctact cccagatccc cgcacacgct tagccccaga catcactgcc cctgggagca  12420
tgcacagcgc agcctcctgc cgacaaaagc aaagtcacaa aaggtgacaa aaatctgcat  12480
ttggggacat ctgattgtga aagagggagg acagtacact tgtagccaca gagactgggg  12540
ctcaccgagc tgaaacctgg tagcactttg gcataacatg tgcatgaccc gtgttcaatg  12600
tctacagatc agtgttgagt aaaacagcct ggtctggggc cgctgctgtc cccacttccc  12660
tcctgtccac cagagggcgg cagagttcct cccaccctgg agcctcccca ggggctgctg  12720
acctccctca gccgggccca cagcccagca gggtccaccc tcacccgggt cacctcggcc  12780
cacgtcctcc tcgccctccg agctcctcac acggactctg tcagctcctc cctgcagcct  12840
atcggccgcc cacctgaggc ttgtcggccg cccacttgag gcctgtcggc tgccctctgc  12900
aggcagctcc tgtcccctac accccctcct tccccgggct cagctgaaag ggcgtctccc  12960
agggcagctc cctgtgatct ccaggacagc tcagtctctc acaggctccg acgcccccta  13020
tgctgtcacc tcacagccct gtcattacca ttaactcctc agtcccatga agttcactga  13080
gcgcctgtct cccggttaca ggaaaactct gtgacaggga ccacgtctgt cctgctctct  13140
gtggaatccc agggcccagc ccagtgcctg acacggaaca gatgctccat aaatactggt  13200
taaatatgtg ggagatctct aaaaagaagc atatcacctc cgtgtggccc ccagcagtca  13260
```

-continued

```
gagtctgttc catgtggaca caggggcact ggcaccagca tgggaggagg ccagcaagtg  13320

cccgcagctg ccccaggaat gaggcctcaa cccccagagc ttcagaaggg aggacagagg  13380

cctgcaggga atagatcctc cggcctgacc ctgcagccta atccagagtt cagggtcagc  13440

tcacaccacg tcgaccctgg tcagcatccc tagggcagtt ccagacaagg ccggaggtct  13500

cctcttgccc tccagggggt gacattgcac acagacatca ctcaggaaac ggattcccct  13560

ggacaggaac ctggctttgc taaggaagtg gaggtggagc ctggtttcca tcccttgctc  13620

caacagaccc ttctgatctc tcccacatac ctgctctgtt cctttctcgg tcctatgagg  13680

accctgttct gccaggggtc cctgtgcaac tccagactcc ctcctggtac caccatgggg  13740

aaggtggggt gatcacagga cagtcagcct cgcagagaca gagaccaccc aggactgtca  13800

gggagaacat ggacaggccc tgagccgcag ctcagccaac agacacggag agggagggtc  13860

cccctggagc cttccccaag gacagcagag cccagagtca cccacctccc tccaccacag  13920

tcctctcttt ccaggacaca caagacacct ccccctccac atgcaggatc tggggactcc  13980

tgagacctct gggcctgggt ctccatccct gggtcagtgg cggggttggt ggtactggag  14040

acagagggct ggtccctccc cagccaccac ccagtgagcc tttttctagc ccccagagcc  14100

acctctgtca ccttcctgtt gggcatcatc ccaccttccc agagccctgg agagcatggg  14160

gagacccggg accctgctgg gtttctctgt cacaaaggaa aataatcccc ctggtgtgac  14220

agacccaagg acagaacaca gcagaggtca gcactgggga agacaggttg tcctcccagg  14280

ggatggggt ccatccacct tgccgaaaag atttgtctga ggaactgaaa atagaaggga  14340

aaaaagagga gggacaaaag aggcagaaat gagaggggag gggacagagg acacctgaat  14400

aaagaccaca cccatgaccc acgtgatgct gagaagtact cctgccctag gaagagactc  14460

agggcagagg gaggaaggac agcagaccag acagtcacag cagccttgac aaaacgttcc  14520

tggaactcaa gctcttctcc acagaggagg acagagcaga cagcagagac catggagtct  14580

ccctcggccc ctccccacag atggtgcatc ccctggcaga ggctcctgct cacaggtgaa  14640

gggaggacaa cctgggagag ggtgggagga gggagctggg gtctcctggg taggacaggg  14700

ctgtgagacg gacagagggc tcctgttgga gcctgaatag ggaagaggac atcagagagg  14760

gacaggagtc acaccagaaa aatcaaattg aactggaatt ggaaaggggc aggaaaacct  14820

caacagttct attttcctag ttaattgtca ctggccacta cgtttttaaa aatcataata  14880

actgcatcag atgacacttt aaataaaaac ataaccaggg catgaaacac tgtcctcatc  14940

cgcctaccgc ggacattgga aaataagccc caggctgtgg agggccctgg gaaccctcat  15000

gaactcatcc acaggaatct gcagcctgtc ccaggcactg ggtgcaaccc aagatc      15056
```

<210> SEQ ID NO 11
<211> LENGTH: 12047
<212> TYPE: DNA
<213> ORGANISM: Homo Sapien

<400> SEQUENCE: 11

```
gaattcagaa ataggggaag gttgaggaag gacactgaac tcaaagggga tacagtgatt     60

ggtttatttg tcttctcttc acaacattgg tgctggagga attcccaccc tgaggttatg    120

aagatgtctg aacacccaac acatagcact ggagatatga gctcgacaag agtttctcag    180

ccacagagat tcacagccta gggcaggagg acactgtacg ccaggcagaa tgacatggga    240

attgcgctca cgattggctt gaagaagcaa ggactgtggg aggtgggctt tgtagtaaca    300
```

-continued

```
agagggcagg gtgaactctg attcccatgg gggaatgtga tggtcctgtt acaaattttt    360
caagctggca gggaataaaa cccattacgg tgaggacctg tggagggcgg ctgccccaac    420
tgataaagga aatagccagg tgggggcctt tcccattgta ggggggacat atctggcaat    480
agaagccttt gagacccttt agggtacaag tactgaggca gcaaataaaa tgaaatctta    540
tttttcaact ttatactgca tgggtgtgaa gatatatttg tttctgtaca gggggtgagg    600
gaaaggaggg gaggaggaaa gttcctgcag gtctggtttg gtcttgtgat ccagggggtc    660
ttggaactat ttaaattaaa ttaaattaaa acaagcgact gttttaaatt aaattaaatt    720
aaattaaatt ttactttatt ttatcttaag ttctgggcta catgtgcagg acgtgcagct    780
ttgttacata ggtaaacgtg tgccatggtg gtttgctgta cctatcaacc catcacctag    840
gtattaagcc cagcatgcat tagctgtttt tcctgacgct ctccctctcc ctgactccca    900
caacaggccc cagtgtgtgt tgttcccctc cctgtgtcca tgtgttctca ttgttcagct    960
cccacttata agtgagaaca tgtggtgttt ggttttctgt ttctgtgtta gtttgctgag   1020
gataatggct tccacctcca tccatgttcc tgcaaaggac gtgatcttat tctttttat    1080
ggttgcatag aaattgtttt tacaaatcca attgatattg tatttaatta caagttaatc   1140
taattagcat actagaagag attacagaag atattaggta cattgaatga ggaaatatat   1200
aaaataggac gaaggtgaaa tattaggtag gaaaagtata atagttgaaa gaagtaaaaa   1260
aaaatatgca tgagtagcag aatgtaaaag aggtgaagaa cgtaatagtg actttttaga   1320
ccagattgaa ggacagagac agaaaaattt taaggaattg ctaaaccatg tgagtgttag   1380
aagtacagtc aataacatta aagcctcagg aggagaaaag aataggaaag gaggaaatat   1440
gtgaataaat agtagagaca tgtttgatgg attttaaaat atttgaaaga cctcacatca   1500
aaggattcat accgtgccat tgaagaggaa gatggaaaag ccaagaagcc agatgaaagt   1560
tagaaatatt attggcaaag cttaaatgtt aaaagtccta gagagaaagg atggcagaaa   1620
tattggcggg aaagaatgca gaacctagaa tataaattca tcccaacagt ttggtagtgt   1680
gcagctgtag ccttttctag ataatacact attgtcatac atcgcttaag cgagtgtaaa   1740
atggtctcct cactttattt atttatatat ttatttagtt ttgagatgga gcctcgctct   1800
gtctcctagg ctggagtgca atagtgcgat accactcact gcaacctctg cctcctctgt   1860
tcaagtgatt ttcttacctc agcctcccga gtagctggga ttacaggtgc gtgccaccac   1920
acccggctaa tttttgtatt ttttgtagag acggggtttt gccatgttgg ccaggctggt   1980
cttgaactcc tgacatcagg tgatccacct gccttggcct cctaaagtgc tgggattaca   2040
ggcatgagcc accgtgccca accactttat ttattttttta tttttatttt taaatttcag   2100
cttctatttg aaatacaggg ggcacatata taggattgtt acatgggtat attgaactca   2160
ggtagtgatc atactaccca acaggtaggt tttcaaccca ctccccctct tttcctcccc   2220
attctagtag tgtgcagtgt ctattgttct catgtttatg tctatgtgtg ctccaggttt   2280
agctcccacc tgtaagtgag aacgtgtggt atttgatttt ctgtccctgt gttaattcac   2340
ttaggattat ggcttccagc tccattcata ttgctgtaaa ggatatgatt catttttcat   2400
ggccatgcag tattccatat tgcgtataga tcacattttc tttctttttt ttttttgaga   2460
cggagtcttg ctttgctgcc taggctggag tgcagtagca cgatctcggc tcactgcaag   2520
cttcacctcc ggggttcacg tcattcttct gtctcagctt cccaagtagc tgggactaca   2580
ggcgcccgcc accacgtccg gctaattttt ttgtgtgttt ttagtagaga tgggggtttc   2640
actgtgttag ccaggatggt cttgatctcc tgaccttgtg gtccacctgc ctcggtctcc   2700
```

-continued

```
caaagtgctg ggattacagg ggtgagccac tgcgcccggc ccatatatac cacattttct   2760
ttaaccaatc caccattgat gggcaactag gtagattcca tggattccac agttttgcta   2820
ttgtgtgcag tgtggcagta gacatatgaa tgaatgtgtc tttttggtat aatgatttgc   2880
attcctttgg gtatacagtc attaatagga gtgctgggtt gaacggtggc tctgtttaaa   2940
attctttgag aattttccaa actgtttgcc atagagagca aactaattta catttccacg   3000
aacagtatat aagcattccc ttttctccac agctttgtca tcatggtttt tttttttctt   3060
tattttaaaa aagaatatgt tgttgttttc ccagggtaca tgtgcaggat gtgcaggttt   3120
gttacatagg tagtaaacgt gagccatggt ggtttgctgc acctgtcaac ccattacctg   3180
ggtatgaagc cctgcctgca ttagctcttt tccctaatgc tctcactact gccccaccct   3240
caccctgaca gggcaaacag acaacctaca gaatgggagg aaatttttgc aatctattca   3300
tctgacaaag gtcaagaata tccagaatct acaaggaact taagcaaatt tttacttttt   3360
aataatagcc actctgactg gcgtgaaatg gtatctcatt gtggttttca tttgaatttc   3420
tctgatgatc agtgacgatg agcatttttt catatttgtt ggctgcttgt acgtcttttg   3480
agaagtgtct cttcatgcct tttggccact ttaatgggat tattttttgc tttttagttt   3540
aagttcctta tagattctgg atattagact tcttattgga tgcatagttt gtgaatactc   3600
tcttccattc tgtaggttgt ctgtttactc tattgatggc ttcttttgct gtgccgaagc   3660
atcttagttt aattagaaac cacctgccaa tttttgtttt tgttgcaatt gcttttgggg   3720
acttagtcat aaactctttg ccaaggtctg ggtcaagaag agtatttcct aggttttctt   3780
ctagaatttt gaaagtctga atgtaaacat ttgcattttt aatgcatctt gagttagttt   3840
ttgtatatgt gaaaggtcta ctctcatttt ctttccctct ttctttcttt ctttcttttc   3900
tttctttctt tctttctttc tttctttctt tctttctttc tttctttttg tccttctttc   3960
tttctttctt tctctttctt tctctctttc tttttttttt ttgatggagt attgctctgt   4020
tgcccaggct gcagtgcagc ggcacgatct cggctcactg caacctctgc ctcctgggtt   4080
caactgattc tcctgcatca gccttccaag tagctgggat tataggcgcc cgccaccacg   4140
cccgactaat ttttgtattt ttagtagaga cggggttgtg ccatgttggc caggctggtt   4200
tgaaactcct gacctcaaac gatctgcctg ccttggcctc ccaaagtgct gggattacag   4260
gtgtgagcca ctgtgcccag ccaagaatgt cattttctaa gaggtccaag aacctcaaga   4320
tattttggga ccttgagaag agaggaattc atacaggtat tacaagcaca gcctaatggc   4380
aaatctttgg catggcttgg cttcaagact ttaggctctt aaaagtcgaa tccaaaaatt   4440
tttataaaag ctccagctaa gctaccttaa aaggggcctg tatggctgat cactcttctt   4500
gctatacttt acacaaataa acaggccaaa tataatgagg ccaaaattta ttttgcaaat   4560
aaattggtcc tgctatgatt tactcttggt aagaacaggg aaaatagaga aaaatttaga   4620
ttgcatctga cctttttttc tgaattttta tatgtgccta caatttgagc taaatcctga   4680
attattttct ggttgcaaaa actctctaaa gaagaacttg gttttcattg tcttcgtgac   4740
acatttatct ggctctttac tagaacagct ttcttgtttt tggtgttcta gcttgtgtgc   4800
cttacagttc tactcttcaa attattgtta tgtgtatctc atagttttcc ttcttttgag   4860
aaaactgaag ccatggtatt ctgaggacta gagatgactc aacagagctg gtgaatctcc   4920
tcatatgcaa tccactgggc tcgatctgct tcaaattgct gatgcactgc tgctaaagct   4980
atacatttaa aaccctcact aaaggatcag ggaccatcat ggaagaggag gaaacatgaa   5040
```

-continued

```
attgtaagag ccagattcgg ggggtagagt gtggaggtca gagcaactcc accttgaata   5100
agaaggtaaa gcaacctatc ctgaaagcta acctgccatg gtggcttctg attaacctct   5160
gttctaggaa gactgacagt ttgggtctgt gtcattgccc aaatctcatg ttaaattgta   5220
atccccagtg ttcggaggtg ggacttggtg gtaggtgatt cggtcatggg agtagatttt   5280
cttctttgtg gtgttacagt gatagtgagt gagttctcgt gagatctggt catttaaaag   5340
tgtgtggccc ctcccctccc tctcttggtc ctcctactgc catgtaagat acctgctcct   5400
gctttgcctt ctaccataag taaaagcccc ctgaggcctc cccagaagca gatgccacca   5460
tgcttcctgt acagcctgca gaaccatcag ccaattaaac ctcttttctg tataaattac   5520
cagtcttgag tatctcttta cagcagtgtg agaacggact aatacaaggg tctccaaaat   5580
tccaagttta tgtattcttt cttgccaaat agcaggtatt taccataaat cctgtcctta   5640
ggtcaaacaa ccttgatggc atcgtacttc aattgtctta cacattcctt ctgaatgact   5700
cctcccctat ggcatataag ccctgggtct tgggggataa tggcagaggg gtccaccatc   5760
ttgtctggct gccacctgag acacggacat ggcttctgtt ggtaagtctc tattaaatgt   5820
ttctttctaa gaaactggat ttgtcagctt gtttctttgg cctctcagct tcctcagact   5880
ttggggtagg ttgcacaacc ctgcccacca cgaaacaaat gtttaatatg ataaatatgg   5940
atagatataa tccacataaa taaaagctct tggagggccc tcaataattg ttaagagtgt   6000
aaatgtgtcc aaagatggaa aatgtttgag aactactgtc ccagagattt tcctgagttc   6060
tagagtgtgg gaatatagaa cctggagctt ggcttcttca gcctagaatc aggagtatgg   6120
ggctgaagtc tgaagcttgg cttcagcagt ttggggttgg cttccggagc acatatttga   6180
catgttgcga ctgtgatttg gggtttggta tttgctctga atcctaatgt ctgtccttga   6240
ggcatctaga atctgaaatc tgtggtcaga attctattat cttgagtagg acatctccag   6300
tcctggttct gccttctagg gctggagtct gtagtcagtg acccggtctg gcatttcaac   6360
ttcatataca gtgggctatc ttttggtcca tgtttcaacc aaacaaccga ataaaccatt   6420
agaacctttc cccacttccc tagctgcaat gttaaaccta ggatttctgt ttaataggtt   6480
catatgaata atttcagcct gatccaactt tacattcctt ctaccgttat tctacaccca   6540
ccttaaaaat gcattcccaa tatattccct ggattctacc tatatatggt aatcctggct   6600
ttgccagttt ctagtgcatt aacatacctg atttacattc ttttacttta aagtggaaat   6660
aagagtccct ctgcagagtt caggagttct caagatggcc cttacttctg acatcaattg   6720
agatttcaag ggagtcgcca agatcatcct caggttcagt gattgctggt agccctcata   6780
taactcaatg aaagctgtta tgctcatggc tatggtttat tacagcaaaa gaatagagat   6840
gaaaatctag caagggaaga gttgcatggg gcaaagacaa ggagagctcc aagtgcagag   6900
attcctgttg ttttctccca gtggtgtcat ggaaagcagt atcttctcca tacaatgatg   6960
tgtgataata ttcagtgtat tgccaatcag ggaactcaac tgagccttga ttatattgga   7020
gcttggttgc acagacatgt cgaccacctt catggctgaa ctttagtact tagcccctcc   7080
agacgtctac agctgatagg ctgtaaccca acattgtcac cataaatcac attgttagac   7140
tatccagtgt ggcccaagct cccgtgtaaa cacaggcact ctaaacaggc aggatatttc   7200
aaaagcttag agatgacctc ccaggagctg aatgcaaaga cctggcctct ttgggcaagg   7260
agaatccttt accgcacact ctccttcaca gggttattgt gaggatcaaa tgtggtcatg   7320
tgtgtgagac accagcacat gtctggctgt ggagagtgac ttctatgtgt gctaacattg   7380
ctgagtgcta agaaagtatt aggcatggct ttcagcactc acagatgctc atctaatcct   7440
```

-continued

```
cacaacatgg ctacagggtg ggcactacta gcctcatttg acagaggaaa ggactgtgga   7500
taagaagggg gtgaccaata ggtcagagtc attctggatg caaggggctc cagaggacca   7560
tgattagaca ttgtctgcag agaaattatg gctggatgtc tctgccccgg aaagggggat   7620
gcactttcct tgacccccta tctcagatct tgactttgag gttatctcag acttcctcta   7680
tgataccagg agcccatcat aatctctctg tgtcctctcc ccttcctcag tcttactgcc   7740
cactcttccc agctccatct ccagctggcc aggtgtagcc acagtaccta actctttgca   7800
gagaactata aatgtgtatc ctacagggga gaaaaaaaaa aagaactctg aaagagctga   7860
cattttaccg acttgcaaac acataagcta acctgccagt tttgtgctgg tagaactcat   7920
gagactcctg ggtcagaggc aaaagatttt attacccaca gctaaggagg cagcatgaac   7980
tttgtgttca catttgttca ctttgccccc caattcatat gggatgatca gagcagttca   8040
ggtggatgga cacaggggtt tgtggcaaag gtgagcaacc taggcttaga aatcctcaat   8100
cttataagaa ggtactagca aacttgtcca gtctttgtat ctgacggaga tattatcttt   8160
ataattgggt tgaaagcaga cctactctgg aggaacatat tgtatttatt gtcctgaaca   8220
gtaaacaaat ctgctgtaaa atagacgtta actttattat ctaaggcagt aagcaaacct   8280
agatctgaag gcgataccat cttgcaaggc tatctgctgt acaaatatgc ttgaaaagat   8340
ggtccagaaa agaaaacggt attattgcct ttgctcagaa gacacacaga aacataagag   8400
aaccatggaa aattgtctcc caacactgtt cacccagagc cttccactct tgtctgcagg   8460
acagtcttaa catcccatca ttagtgtgtc taccacatct ggcttcaccg tgcctaacca   8520
agatttctag gtccagttcc ccaccatgtt tggcagtgcc ccactgccaa ccccagaata   8580
agggagtgct cagaattccg aggggacatg ggtggggatc agaacttctg ggcttgagtg   8640
cagaggggc ccatactcct tggttccgaa ggaggaagag gctggaggtg aatgtccttg   8700
gaggggagga atgtgggttc tgaactctta aatccccaag ggaggagact ggtaaggtcc   8760
cagcttccga ggtactgacg tgggaatggc ctgagaggtc taagaatccc gtatcctcgg   8820
gaaggagggg ctgaaattgt gaggggttga gttgcagggg tttgttagct tgagactcct   8880
tggtgggtcc ctgggaagca aggactggaa ccattggctc cagggtttgg tgtgaaggta   8940
atgggatctc ctgattctca aagggtcaga ggactgagag ttgcccatgc tttgatcttt   9000
ccatctactc cttactccac ttgagggtaa tcacctactc ttctagttcc acaagagtgc   9060
gcctgcgcga gtataatctg cacatgtgcc atgtcccgag gcctggggca tcatccactc   9120
atcattcagc atctgcgcta tgcgggcgag gccggcgcca tgacgtcatg tagctgcgac   9180
tatccctgca gcgcgcctct cccgtcacgt cccaaccatg gagctgtgga cgtgcgtccc   9240
ctggtggatg tggcctgcgt ggtgccaggc cggggcctgg tgtccgataa agatcctaga   9300
accacaggaa accaggactg aaaggtgcta gagaatggcc atatgtcgct gtccatgaaa   9360
tctcaaggac ttctgggtgg agggcacagg agcctgaact tacgggtttg ccccagtcca   9420
ctgtcctccc aagtgagtct cccagatacg aggcactgtg ccagcatcag cttcatctgt   9480
accacatctt gtaacaggga ctacccagga ccctgatgaa caccatggtg tgtgcaggaa   9540
gagggggtga aggcatggac tcctgtgtgg tcagagccca gagggggcca tgacgggtgg   9600
ggaggaggct gtggactggc tcgagaagtg ggatgtggtt gtgtttgatt tcctttggcc   9660
agataaagtg ctggatatag cattgaaaac ggagtatgaa gaccagttag aatggagggt   9720
caggttggag ttgagttaca gatggggtaa aattctgctt cggatgagtt tggggattgg   9780
```

-continued

```
caatctaaag gtggtttggg atggcatggc tttgggatgg aaataggttt gtttttatgt   9840
tggctgggaa gggtgtgggg attgaattgg ggatgaagta ggtttagttt tggagataga   9900
atacatggag ctggctattg catgcgagga tgtgcattag tttggtttga tctttaaata   9960
aaggaggcta ttagggttgt cttgaattag attaagttgt gttgggttga tgggttgggc  10020
ttgtgggtga tgtggttgga ttgggctgtg ttaaattggt ttgggtcagg ttttggttga  10080
ggttatcatg gggatgagga tatgcttggg acatggattc aggtggttct cattcaagct  10140
gaggcaaatt tcctttcaga cggtcattcc agggaacgag tggttgtgtg ggggaaatca  10200
ggccactggc tgtgaatatc cctctatcct ggtcttgaat tgtgattatc tatgtccatt  10260
ctgtctcctt cactgtactt ggaattgatc tggtcattca gctggaaatg ggggaagatt  10320
ttgtcaaatt cttgagacac agctgggtct ggatcagcgt aagccttcct tctggtttta  10380
ttgaacagat gaaatcacat tttttttttc aaaatcacag aaatcttata gagttaacag  10440
tggactctta taataagagt taacaccagg actcttattc ttgattcttt tctgagacac  10500
caaaatgaga tttctcaatg ccaccctaat tctttttttt tttttttttt tttttgagac  10560
acagtctggg tcttttgctc tgtcactcag gctggagcgc agtggtgtga tcatagctca  10620
ctgaaccctt gacctcctgg acttaaggga tcctcctgct tcagcctcct gagtagatgg  10680
ggctacaggt gcttgccacc acacctggct aattaaattt tttttttttt tttgtagaga  10740
aagggtctca ctttgttgcc ctggctgatc ttgaacttct gacttcaagt gattcttcag  10800
ccttggactc ccaaagcact gggattgctg gcatgagcca ctcaccgtgc ctggcttgca  10860
gcttaatctt ggagtgtata aacctggctc ctgatagcta gacatttcag tgagaaggag  10920
gcattggatt ttgcatgagg acaattctga cctaggaggg caggtcaaca ggaatccccg  10980
ctgtacctgt acgttgtaca ggcatggaga atgaggagtg aggaggccgt accggaaccc  11040
catattgttt agtggacatt ggattttgaa ataataggga acttggtctg ggagagtcat  11100
atttctggat tggacaatat gtggtatcac aaggttttat gatgagggag aaatgtatgt  11160
ggggaaccat tttctgagtg tggaagtgca agaatcagag agtagctgaa tgccaacgct  11220
tctatttcag gaacatggta agttggaggt ccagctctcg ggctcagacg ggtataggga  11280
ccaggaagtc tcacaatccg atcattctga tatttcaggg catattaggt ttggggtgca  11340
aaggaagtac ttgggactta ggcacatgag actttgtatt gaaaatcaat gattggggct  11400
ggccgtggtg ctcacgcctg taatctcatc actttgggag accgaagtgg gaggatggct  11460
tgatctcaag agttggacac cagcctaggc aacatggcca gaccctctct ctacaaaaaa  11520
attaaaaatt agctggatgt ggtggtgcat gcttgtggtc tcagctatcc tggaggctga  11580
gacaggagaa tcggttgagt ctgggagttc aaggctacag ggagctgcga tcacgccgct  11640
gcactccagc ctgggaaaca gagtgagact gtctcagaat ttttttaaaa aagaatcagt  11700
gatcatccca acccctgttg ctgttcatcc tgagcctgcc ttctctggct ttgttcccta  11760
gatcacatct ccatgatcca taggccctgc ccaatctgac ctcacaccgt gggaatgcct  11820
ccagactgat ctagtatgtg tggaacagca agtgctggct ctccctcccc ttccacagct  11880
ctgggtgtgg gagggggttg tccagcctcc agcagcatgg ggagggcctt ggtcagcatc  11940
taggtgccaa cagggcaagg gcggggtcct ggagaatgaa ggctttatag ggctcctcag  12000
ggaggccccc cagccccaaa ctgcaccacc tggccgtgga caccggt                12047
```

<210> SEQ ID NO 12
<211> LENGTH: 858

-continued

<212> TYPE: DNA
<213> ORGANISM: Homo Sapien

<400> SEQUENCE: 12
cgagcggccc ctcagcttcg gcgcccagcc ccgcaaggct cccggtgacc actagagggc 60
gggaggagct cctggccagt ggtggagagt ggcaaggaag gaccctaggg ttcatcggag 120
cccaggttta ctcccttaag tggaaatttc ttcccccact cctccttggc tttctccaag 180
gagggaaccc aggctgctgg aaagtccggc tggggcgggg actgtgggtt caggggagaa 240
cggggtgtgg aacgggacag ggagcggtta gaagggtggg gctattccgg gaagtggtgg 300
ggggagggag cccaaaacta gcacctagtc cactcattat ccagccctct tatttctcgg 360
ccgctctgct tcagtggacc cggggagggc ggggaagtgg agtgggagac ctaggggtgg 420
gcttcccgac cttgctgtac aggacctcga cctagctggc tttgttcccc atccccacgt 480
tagttgttgc cctgaggcta aaactagagc ccaggggccc caagttccag actgcccctc 540
ccccctcccc cggagccagg gagtggttgg tgaaaggggg aggccagctg gagaacaaac 600
gggtagtcag gggg ttgagc gattagagcc cttgtaccct acccaggaat ggttggggag 660
gaggaggaag aggtaggagg taggggaggg ggcggggttt tgtcacctgt cacctgctcg 720
ctgtgcctag ggcgggcggg cggggagtgg ggggaccggt ataaagcggt aggcgcctgt 780
gcccgctcca cctctcaagc agccagcgcc tgcctgaatc tgttctgccc cctccccacc 840
catttcacca ccaccatg 858

<210> SEQ ID NO 13
<211> LENGTH: 454
<212> TYPE: DNA
<213> ORGANISM: Rattus rattus

<400> SEQUENCE: 13
aagcttccac aagtgcattt agcctctcca gtattgctga tgaatccaca gttcaggttc 60
aatggcgttc aaaacttgat caaaaatgac cagactttat attcttacac caacatctat 120
ctgattggag gaatggataa tagtcatcat gtttaaacat ctaccattcc agttaagaaa 180
atatgatagc atcttgttct tagtcttttt cttaataggg acataaagcc cacaaataaa 240
aatatgcctg aagaatggga caggcattgg gcattgtcca tgcctagtaa agtactccaa 300
gaacctattt gtatactaga tgacacaatg tcaatgtctg tgtacaactg ccaactggga 360
tgcaagacac tgcccatgcc aatcatcctg aaaagcagct ataaaaagca ggaagctact 420
ctgcaccttg tcagtgaggt ccagatacct acag 454

<210> SEQ ID NO 14
<211> LENGTH: 822
<212> TYPE: DNA
<213> ORGANISM: Homo Sapien

<400> SEQUENCE: 14
gcattgctgt gaactctgta cttaggacta aactttgagc aataacacac atagattgag 60
gattgtttgc tgttagcata caaactctgg ttcaaagctc ctctttattg cttgtcttgg 120
aaaatttgct gttcttcatg gtttctcttt tcactgctat ctatttttct caaccactca 180
catggctaca ataactgtct gcaagcttat gattcccaaa tatctatctc tagcctcaat 240
cttgttccag aagataaaaa gtagtattca aatgcacatc aacgtctcca cttggagggc 300
ttaaagacgt ttcaacatac aaaccgggga gttttgcctg gaatgtttcc taaaatgtgt 360

-continued

```
cctgtagcac atagggtcct cttgttcctt aaaatctaat tacttttagc ccagtgctca     420

tcccacctat ggggagatga gagtgaaaag ggagcctgat taataattac actaagtcaa     480

taggcataga gccaggactg tttgggtaaa ctggtcactt tatcttaaac taaatatatc     540

caaaactgaa catgtactta gttactaagt ctttgacttt atctcattca taccactcag     600

ctttatccag gccacttatg agctctgtgt ccttgaacat aaaatacaaa taaccgctat     660

gctgttaatt attggcaaat gtcccatttt caacctaagg aaataccata aagtaacaga     720

tataccaaca aaaggttact agttaacagg cattgcctga aaagagtata aaagaatttc     780

agcatgattt tccatattgt gcttccacca ctgccaataa ca                        822


<210> SEQ ID NO 15
<211> LENGTH: 5224
<212> TYPE: DNA
<213> ORGANISM: Homo Sapien

<400> SEQUENCE: 15

gaattcttag aaatatgggg gtaggggtgg tggtggtaat tctgttttca ccccataggt      60

gagataagca ttgggttaaa tgtgctttca cacacacatc acatttcata agaattaagg     120

aacagactat gggctggagg actttgagga tgtctgtctc ataacacttg ggttgtatct     180

gttctatggg gcttgtttta agcttggcaa cttgcaacag ggttcactga ctttctcccc     240

aagcccaagg tactgtcctc ttttcatatc tgttttgggg cctctggggc ttgaatatct     300

gagaaaatat aaacatttca ataatgttct gtggtgagat gagtatgaga gatgtgtcat     360

tcatttgtat caatgaatga atgaggacaa ttagtgtata aatccttagt acaacaatct     420

gagggtaggg gtggtactat tcaatttcta tttataaaga tacttatttc tatttattta     480

tgcttgtgac aaatgttttg ttcgggacca caggaatcac aaagatgagt ctttgaattt     540

aagaagttaa tggtccagga ataattacat agcttacaaa tgactatgat ataccatcaa     600

acaagaggtt ccatgagaaa ataatctgaa aggtttaata agttgtcaaa ggtgagaggg     660

ctcttctcta gctagagact aatcagaaat acattcaggg ataattattt gaatagacct     720

taagggttgg gtacattttg ttcaagcatt gatggagaag gagagtgaat atttgaaaac     780

attttcaact aaccaaccac ccaatccaac aaacaaaaaa tgaaaagaat ctcagaaaca     840

gtgagataag agaaggaatt ttctcacaac ccacacgtat agctcaactg ctctgaagaa     900

gtatatatct aatatttaac actaacatca tgctaataat gataataatt actgtcattt     960

tttaatgtct ataagtacca ggcatttaga agatattatt ccatttatat atcaaaataa    1020

acttgagggg atagatcatt ttcatgatat atgagaaaaa ttaaaaacag attgaattat    1080

ttgcctgtca tacagctaat aattgaccat aagacaatta gatttaaatt agttttgaat    1140

ctttctaata ccaaagttca gtttactgtt ccatgttgct tctgagtggc ttcacagact    1200

tatgaaaaag taaacggaat cagaattaca tcaatgcaaa agcattgctg tgaactctgt    1260

acttaggact aaactttgag caataacaca catagattga ggattgtttg ctgttagcat    1320

acaaactctg gttcaaagct cctctttatt gcttgtcttg gaaaatttgc tgttcttcat    1380

ggtttctctt ttcactgcta tctatttttc tcaaccactc acatggctac aataactgtc    1440

tgcaagctta tgattcccaa atatctatct ctagcctcaa tcttgttcca gaagataaaa    1500

agtagtattc aaatgcacat caacgtctcc acttggaggg cttaaagacg tttcaacata    1560

caaaccgggg agttttgcct ggaatgtttc ctaaaatgtg tcctgtagca catagggtcc    1620

tcttgttcct taaaatctaa ttacttttag cccagtgctc atcccaccta tggggagatg    1680
```

-continued

```
agagtgaaaa gggagcctga ttaataatta cactaagtca ataggcatag agccaggact   1740
gtttgggtaa actggtcact ttatcttaaa ctaaatatat ccaaaactga acatgtactt   1800
agttactaag tctttgactt tatctcattc ataccactca gctttatcca ggccacttat   1860
ttgacagtat tattgcgaaa acttcctaac tggtctcctt atcatagtct tatccccttt   1920
tgaaacaaaa gagacagttt caaaatacaa atatgatttt tattagctcc cttttgttgt   1980
ctataatagt cccagaagga gttataaact ccatttaaaa agtctttgag atgtggccct   2040
tgccaacttt gccaggaatt cccaatatct agtattttct actattaaac tttgtgcctc   2100
ttcaaaactg cattttctct cattccctaa gtgtgcattg ttttccctta ccggttggtt   2160
tttccaccac cttttacatt ttcctggaac actataccct ccctcttcat ttggcccacc   2220
tctaattttc tttcagatct ccatgaagat gttacttcct ccaggaagcc ttatctgacc   2280
cctccaaaga tgtcatgagt tcctcttttc attctactaa tcacagcatc catcacacca   2340
tgttgtgatt actgatacta ttgtctgttt ctctgattag gcagtaagct caacaagagc   2400
tacatggtgc ctgtctcttg ttgctgatta ttcccatcca aaaacagtgc ctggaatgca   2460
gacttaacat tttattgaat gaataaataa aaccccatct atcgagtgct actttgtgca   2520
agacccggtt ctgaggcatt tatatttatt gatttattta attctcattt aaccatgaag   2580
gaggtactat cactatcctt attttatagt tgataaagat aaagcccaga gaaatgaatt   2640
aactcaccca aagtcatgta gctaagtgac agggcaaaaa ttcaaaccag ttccccaact   2700
ttacgtgatt aatactgtgc tatactgcct ctctgatcat atggcatgga atgcagacat   2760
ctgctccgta aggcagaata tggaaggaga ttggaggatg acacaaaacc agcataatat   2820
cagaggaaaa gtccaaacag gacctgaact gatagaaaag ttgttactcc tggtgtagtc   2880
gcatcgacat cttgatgaac tggtggctga cacaacatac attggcttga tgtgtacata   2940
ttatttgtag ttgtgtgtgt atttttatat atatatttgt aatattgaaa tagtcataat   3000
ttactaaagg cctaccattt gccaggcatt tttacatttg tcccctctaa tcttttgatg   3060
agatgatcag attggattac ttggccttga agatgatata tctacatcta tatctatatc   3120
tatatctata tctatatcta tatctatatc tatatctata tatgtatatc agaaaagctg   3180
aaatatgttt tgtaaagtta taaagatttc agactttata gaatctggga tttgccaaat   3240
gtaacccctt tctctacatt aaacccatgt tggaacaaat acatttatta ttcattcatc   3300
aaatgttgct gagtcctggc tatgaaccag acactgtgaa agcctttggg atattttgcc   3360
catgcttggg caagcttata tagtttgctt cataaaactc tatttcagtt cttcataact   3420
aatacttcat gactattgct tttcaggtat tccttcataa caaatacttt ggctttcata   3480
tatttgagta aagtcccccct tgaggaagag tagaagaact gcactttgta aatactatcc   3540
tggaatccaa acggatagac aaggatggtg ctacctcttt ctggagagta cgtgagcaag   3600
gcctgttttg ttaacatgtt ccttaggaga caaaacttag gagagacacg catagcagaa   3660
aatggacaaa aactaacaaa tgaatgggaa ttgtacttga ttagcattga agaccttgtt   3720
tatactatga taaatgtttg tatttgctgg aagtgctact gacggtaaac cctttttgtt   3780
taaatgtgtg ccctagtagc ttgcagtatg atctattttt taagtactgt acttagctta   3840
tttaaaaatt ttatgtttaa aattgcatag tgctctttca ttgaagaagt tttgagagag   3900
agatagaatt aaattcactt atcttaccat ctagagaaac ccaatgttaa aactttgttg   3960
tccattattt ctgtctttta ttcaacattt tttttagagg gtgggaggaa tacagaggag   4020
```

-continued

```
gtacaatgat acacaaatga gagcactctc catgtattgt tttgtcctgt ttttcagtta   4080

acaatatatt atgagcatat ttccatttca ttaaatattc ttccacaaag ttattttgat   4140

ggctgtatat caccctactt tatgaatgta ccatattaat ttatttcctg gtgtgggtta   4200

tttgatttta taatcttacc tttagaataa tgaaacacct gtgaagcttt agaaaatact   4260

ggtgcctggg tctcaactcc acagattctg atttaactgg tctgggttac agactaggca   4320

ttgggaattc aaaaagttcc cccagtgatt ctaatgtgta gccaagatcg ggaacccttg   4380

tagacaggga tgataggagg tgagccactc ttagcatcca tcatttagta ttaacatcat   4440

catcttgagt tgctaagtga atgatgcacc tgacccactt tataaagaca catgtgcaaa   4500

taaaattatt ataggacttg gtttattagg gcttgtgctc taagttttct atgttaagcc   4560

atacatcgca tactaaatac tttaaaatgt accttattga catacatatt aagtgaaaag   4620

tgtttctgag ctaaacaatg acagcataat tatcaagcaa tgataatttg aaatgaattt   4680

attattctgc aacttaggga caagtcatct ctctgaattt tttgtacttt gagagtattt   4740

gttatatttg caagatgaag agtctgaatt ggtcagacaa tgtcttgtgt gcctggcata   4800

tgataggcat ttaatagttt taaagaatta atgtatttag atgaattgca taccaaatct   4860

gctgtctttt ctttatggct tcattaactt aatttgagag aaattaatta ttctgcaact   4920

tagggacaag tcatgtcttt gaatattctg tagtttgagg agaatatttg ttatatttgc   4980

aaaataaaat aagtttgcaa gttttttttt tctgccccaa agagctctgt gtccttgaac   5040

ataaaataca aataaccgct atgctgttaa ttattggcaa atgtcccatt ttcaacctaa   5100

ggaaatacca taaagtaaca gatataccaa caaaaggtta ctagttaaca ggcattgcct   5160

gaaaagagta taaaagaatt tcagcatgat tttccatatt gtgcttccac cactgccaat   5220

aaca                                                                5224
```

<210> SEQ ID NO 16
<211> LENGTH: 29
<212> TYPE: DNA
<213> ORGANISM: Artificial Sequence
<220> FEATURE:
<223> OTHER INFORMATION: Synthetic construct

<400> SEQUENCE: 16

```
gtgaccggtg cattgctgtg aactctgta                                       29
```

<210> SEQ ID NO 17
<211> LENGTH: 27
<212> TYPE: DNA
<213> ORGANISM: Artificial Sequence
<220> FEATURE:
<223> OTHER INFORMATION: Synthetic construct

<400> SEQUENCE: 17

```
ataagtggcc tggataaagc tgagtgg                                         27
```

<210> SEQ ID NO 18
<211> LENGTH: 28
<212> TYPE: DNA
<213> ORGANISM: Artificial Sequence
<220> FEATURE:
<223> OTHER INFORMATION: Synthetic construct

<400> SEQUENCE: 18

```
gtcaccggtc tttgttattg gcagtggt                                        28
```

-continued

```
<210> SEQ ID NO 19
<211> LENGTH: 30
<212> TYPE: DNA
<213> ORGANISM: Artificial Sequence
<220> FEATURE:
<223> OTHER INFORMATION: Synthetic construct

<400> SEQUENCE: 19

atccaggcca cttatgagct ctgtgtcctt                                30


<210> SEQ ID NO 20
<211> LENGTH: 21
<212> TYPE: DNA
<213> ORGANISM: Artificial Sequence
<220> FEATURE:
<223> OTHER INFORMATION: Synthetic construct

<400> SEQUENCE: 20

gagacatatt atctgccacg g                                         21


<210> SEQ ID NO 21
<211> LENGTH: 21
<212> TYPE: DNA
<213> ORGANISM: Artificial Sequence
<220> FEATURE:
<223> OTHER INFORMATION: Synthetic construct

<400> SEQUENCE: 21

cgttaagcaa gtcctcgata c                                         21


<210> SEQ ID NO 22
<211> LENGTH: 24
<212> TYPE: DNA
<213> ORGANISM: Artificial Sequence
<220> FEATURE:
<223> OTHER INFORMATION: Synthetic construct

<400> SEQUENCE: 22

ttggttttgg aggtttctgt gggg                                      24


<210> SEQ ID NO 23
<211> LENGTH: 24
<212> TYPE: DNA
<213> ORGANISM: Artificial Sequence
<220> FEATURE:
<223> OTHER INFORMATION: Synthetic construct

<400> SEQUENCE: 23

aaaggccacc ctatcctccg tatc                                      24
```

TARGET CELL-SPECIFIC ADENOVIRAL VECTORS CONTAINING E3 AND METHODS OF USE THEREOF

CROSS-REFERENCE TO RELATED APPLICATIONS

This application claims the priority benefit of U.S. Provisional Patent Application No. 60/114,262, filed Dec. 30, 1998. The priority application is hereby incorporated herein by reference in its entirety.

STATEMENT OF RIGHTS TO INVENTIONS MADE UNDER FEDERALLY SPONSORED RESEARCH (Not applicable)

TECHNICAL FIELD

This invention relates to the field of adenoviral vectors and transfection. More specifically, the invention relates to target cell-specific adenoviral vectors containing E3.

BACKGROUND ART

In spite of numerous advances in medical research, cancer remains the second leading cause of death in the United States. In the industrialized nations, roughly one in five persons will die of cancer. Traditional modes of clinical care, such as surgical resection, radiotherapy and chemotherapy, have a significant failure rate, especially for solid tumors. Neoplasia resulting in benign tumors can usually be completely cured by removing the mass surgically. If a tumor becomes malignant, as manifested by invasion of surrounding tissue, it becomes much more difficult to eradicate. Once a malignant tumor metastasizes, it is much less likely to be eradicated.

A major, indeed the overwhelming, obstacle to cancer therapy is the problem of selectivity; that is, the ability to inhibit the multiplication of tumor cells, while leaving unaffected the function of normal cells. For example, in prostate cancer therapy, the therapeutic ratio, or ratio of tumor cell killing to normal cell killing of traditional tumor chemotherapy, is only 1.5:1. Thus, more effective treatment methods and pharmaceutical compositions for therapy and prophylaxis of neoplasia are needed.

One possible treatment approach for many of these cancers is gene therapy, whereby a gene of interest is introduced into the malignant cell. Various viral vectors, including adenoviral vectors, have been developed as vehicles for gene therapy. The virtually exclusive focus in development of adenoviral vectors for gene therapy is use of adenovirus merely as a vehicle for introducing the gene of interest, not as an effector in itself. Replication of adenovirus has been viewed as an undesirable result. In the treatment of cancer by replication-defective adenoviruses, the host immune response limits the duration of repeat doses at two levels. First, the capsid proteins of the adenovirus delivery vehicle itself are immunogenic. Second, viral late genes are frequently expressed in transduced cells, eliciting cellular immunity to the virus-infected cells. Thus, the ability to repeatedly administer cytokines, tumor suppressor genes, ribozymes, suicide genes, or genes which convert prodrug to an active drug has been limited by the immunogenicity of both the gene transfer vehicle and the viral gene products of the transfer vehicle as well as the transient nature of gene expression.

Adenovirus can cause persistent infections in humans and animals. The strategies of C type adenovirus (type Ad2 and Ad5) for evading host immune recognition are many, and generally involve E3, a delayed early transcription unit whose transcription is induced by the 289R E1A protein. During early stages of infection, the E3 promoter drives expression of nine alternatively spliced mRNAs that are polyadenylated at one of two sites, E3A and E3B. Wold et al. (1995) *Curr. Topics Microbiol. Immunol.* 199 (Pt.1) :237–274. None of the E3 proteins is apparently required for adenovirus replication in cultured cells or in the lungs of hamsters or cotton rats, but they appear to play a role in evasion of host immune surveillance.

Six proteins which are encoded by the Ad-E3 region have been identified and characterized: (1) a 19-kDa glycoprotein (gp19k) is one of the most abundant adenovirus early proteins, and is known to inhibit transport of the major histocompatibility complex class I molecules to the cell surface, thus impairing both peptide recognition and clearance of Ad-infected cells by cytotoxic T lymphocytes (CTLs); (2) E3 14.7k protein and the E3 10.4k/14.5k complex of proteins inhibit the cytotoxic and inflammatory responses mediated by tumor necrosis factor (TNF); (3) E3 10.4k/14.5k protein complex downregulates the epidermal growth factor receptor, which may inhibit inflammation and activate quiescent infected cells for efficient virus replication; (4) E3 11.6k protein (adenoviral death protein, ADP) from adenovirus 2 and 5 appears to promote cell death and release of virus from infected cells. Other studies have indicated that the E3-encoded 10.4K/14.5K complex proteins down-modulate the apoptosis receptor Fas/Apo-1. Elsing and Burger (1998) *Proc. Natl. Acad. Sci. USA* 95:10072–10077; and Shisler et al. (1997) *J. Virol.* 71:8299–8306. The functions of three E3-encoded proteins—3.6k, 6.7k, and 12.5k—are currently unknown. Wold et al. (1995).

Traditionally, the pervasive dogma regarding the role of E3 in adenoviral vectors for gene therapy was that E3 should be deleted. E3 was viewed as non-essential for replication, and its deletion allowed insertion of foreign genes. Indeed, until quite recently, all adenoviral vectors lacked the E3 region.

More recently, it has been demonstrated that incorporation of E3 genes in the engineered adenovirus reduces the antiviral immune response and prolongs expression of foreign genes delivered by adenoviral vectors. It was shown that insertion of E3 genes in recombinant adenovirus facilitates re-administration of a functional vector for long-term gene expression and correction of an inherited metabolic disorder. Horwitz et al. (1995) *Curr. Topics Microbiol. Immunol.* 199(Pt 1):195–211. Other studies have indicated that, while expression from E3-deleted vectors is essentially turned off eight weeks after gene transfer, an E3-containing vector supported transgene expression with therapeutic levels of human factor IX in vivo for more than 4 months. Poller et al. (1996) *Gene Ther.* 3:521–530. The enhanced stability was attributed to efficient E3 region-mediated suppression of the host's antiviral immune response. More recently, it was demonstrated that a wild-type E3-containing adenoviral vector could direct prolonged expression of a non-immunogenic transgene. Persistence of this gene expression was also attributed to the presence of the E3 region. Wadsworth et al. (1997) *J. Virol.* 71:5189–5196. Further, when a recombinant adenovirus vector encoding hepatitis B surface antigen and containing an intact E3 region was used to infect chimpanzees, greater viral persistence, as indicated by the duration of virus shedding, was observed compared to counterpart vectors lacking E3. This phenomenon was attributed to evasion of host immune response. Chengalvala et al. (1997) *Vaccine* 15:335–339. However, the above-described E3-containing adenoviral vectors were not replication competent and target cell specific. All of these studies employed adenovirus as a vehicle for expressing a transgene.

Use of adenoviral vectors as therapeutic vehicles for cancer has been reported. See, for example, Bischoff et al. (1996) *Science* 274:373–376; WO 96/349969; WO 96/17053. Some of these approaches utilize target cell-type specific transcriptional regulatory elements to selectively drive adenoviral replication (and thus cytotoxicity). U.S. Pat. No. 5,698,443; see also WO 95/11984; WO 96/17053; WO 98/39465; WO 98/39467; WO 98/39466; and WO 98/39464. These vectors were deleted for E3.

Based on the teachings of the prior art, inclusion of E3 is not indicated in the context of using adenoviral vector replication for its cytotoxic effects (as opposed to using an adenoviral vectors as gene delivery vehicles), as suppression of the host's cytotoxic T cell response would not be considered a positive or desirable result. Further, inclusion of E3 into replication-competent adenoviral vectors would not be indicated since the well-accepted understanding in the art is that E3 is not necessary for viral replication.

Besides cancerous cells, it is often desirable to selectively destroy certain unwanted cells or tissues. Apart from surgery, however, which is invasive, there is a dearth of methods available, particularly non-invasive methods, which would allow such selective cytotoxicity and/or suppression.

There is a need for vector constructs that are capable of rapidly eliminating cancerous cells in a minimum number of administrations and which are suitable for use in cancer ablation treatments. There is also a need for an ability to selectively destroy, or impair, unwanted cells, regardless of cell type and/or regardless of anatomical location.

All publications and patent applications cited herein are hereby incorporated by reference in their entirety.

SUMMARY OF THE INVENTION

The invention provides target cell-specific adenoviral vectors (i.e., they are preferentially cytotoxic toward a specific target cell) comprising E3 (or an E3 sequence, or a portion of an E3 region), compositions, host cells, and kits comprising these vectors, and methods using these vectors. Preferably, the vectors are replication competent. These target cell-specific vectors express E3-encoded protein(s) and exhibit significantly greater cytotoxicity and/or enhanced adenoviral production per cell.

Accordingly, in one aspect, the invention provides an adenovirus vector comprising (a) an adenovirus gene under transcriptional control of a target cell-specific transcriptional regulatory element (TRE); and (b) an E3 region. In another aspect, an adenovirus vector of the invention comprises (a) an adenovirus gene under transcriptional control of a target cell-specific transcriptional regulatory element (TRE); and (b) an E3 sequence. In some embodiments the adenoviral gene under transcriptional control of a target cell-specific TRE is one that is essential for adenoviral propagation, such as E1A and/or E1B. In some embodiments, the target cell-specific TRE confers cell type-specific transcriptional regulation on the operably linked adenoviral gene. In other embodiments, the target cell-specific TRE is a cell status-specific TRE.

In other embodiments, the invention provides an adenovirus vector comprising (a) an adenovirus gene under transcriptional control of a target cell-specific transcriptional regulatory element (TRE); and (b) a portion of an E3 region.

In another aspect, the invention provides a replication competent adenovirus vector comprising an E3 sequence (or E3 region) under transcriptional control of a target cell specific TRE.

In another aspect, E3-containing, target-cell-specific adenoviral vectors of the invention further contain one or more transgenes. In some of these embodiments, a transgene can be under transcriptional control of a heterologous TRE, which may be a target cell-specific TRE.

In another aspect, the invention provides an adenoviral vector comprising an E3 region (or a portion of an E3 region, or an E3 sequence) under transcriptional control of a target-cell specific TRE.

In another aspect, the invention provides a host cell comprising an adenovirus vector(s) described herein.

In another aspect, the invention provides compositions comprising an adenovirus vector(s) described herein, preferably further comprising a pharmaceutically acceptable excipient.

In another aspect, the invention provides kits which contain an adenoviral vector(s) described herein.

In another aspect, methods are provided for propagating an adenovirus specific for mammalian cells which permit the function of a target cell-specific TRE, said method comprising combining an adenovirus vector(s) described herein with mammalian cells that permit the function of a target cell-specific TRE, such that the adenovirus vector(s) enters the cell, whereby said adenovirus is propagated.

In another aspect, methods are provided for conferring selective cytotoxicity in target cells, comprising contacting the cells with an adenovirus vector(s) described herein, whereby the vector enters the cell.

The invention further provides methods of suppressing tumor cell growth, more particularly a target tumor cell, comprising contacting a tumor cell with an adenoviral vector of the invention such that the adenoviral vector enters the tumor cell and exhibits selective cytotoxicity for the tumor cell.

In another aspect, methods are provided for detecting a cell which allows the function of a target cell-specific TRE, which comprise contacting a cell in a biological sample with an adenovirus vector(s) of the invention, and detecting replication of the adenovirus vector(s), if any.

BRIEF DESCRIPTION OF THE DRAWINGS

FIG. 20 shows the nucleotide sequence of a hypoxia-responsive element (HRE) from the 5' flanking region of a rat enolase-1 gene (SEQ ID NO:7).

FIG. 21 shows the nucleotide sequence of the 5' flanking region of a human E2F1 gene (SEQ ID NO:8). The asterisk indicates the transcription start site.

FIG. 22 depicts a nucleotide sequence of a PSA-TRE (SEQ ID NO:9).

FIG. 23 depicts a nucleotide sequence of a CEA-TRE (SEQ ID NO:10). The bent arrow above nucleotide 14,466 indicates the transcription start site.

FIG. 24 depicts a nucleotide sequence of a human glandular kallikrein TRE (SEQ ID NO:11).

FIG. 25 depicts a nucleotide sequence of a mucin TRE (SEQ ID NO:12).

FIG. 26 depicts a nucleotide sequence of a rat probasin TRE (SEQ ID NO:13).

FIG. 27 depicts the nucleotide sequence of the AFP-TRE driving expression of E1A in CN733 (SEQ ID NO:14).

FIG. 28 depicts a nucleotide sequence of an AFP-TRE (SEQ ID NO:15).

In FIG. 34A, mice were treated with 3 injections of $4\times10^{9}$ pfu of CN790 (squares, n=7) or vehicle alone (triangles, n=8). Arrows indicate injection times. In FIG. 34B, mice were treated with either CN790 (squares) or vehicle alone (triangles).

MODES FOR CARRYING OUT THE INVENTION

Figure 1:
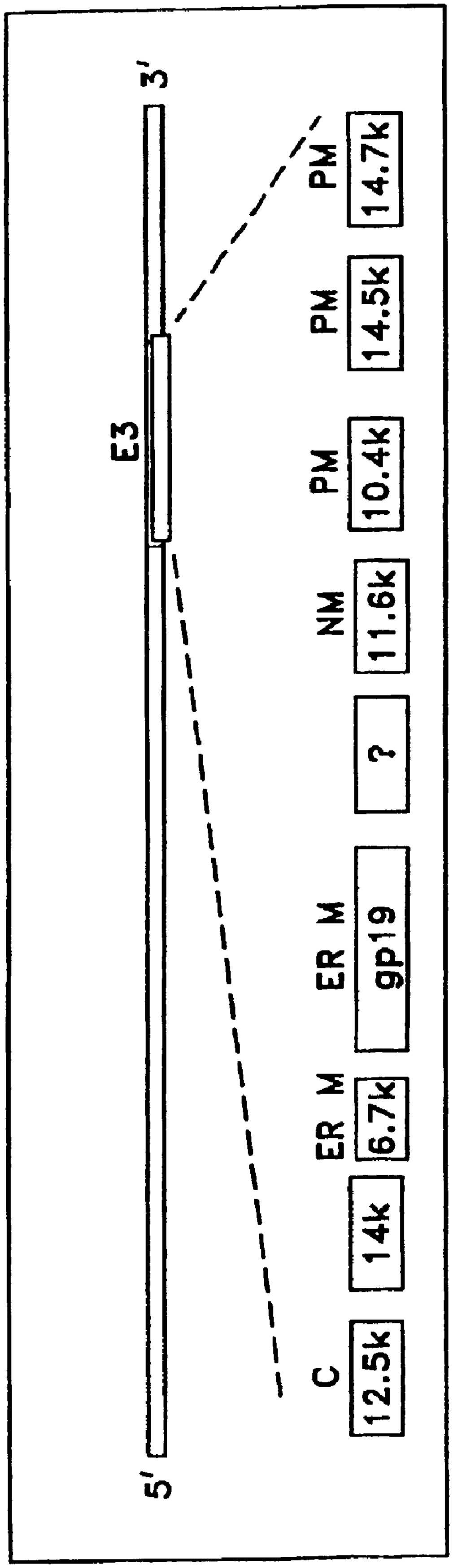
FIG. 1 is a schematic representation of the E3 region of adenovirus. Letters above the boxes indicate known cellular locations of the corresponding polypeptide as follows: C, cytoplasm; ER M, endoplasmic reticulum membrane; NM, nuclear membrane; and PM, plasma membrane.

We have discovered target cell-specific adenovirus vectors which contain an E3 region (or portion of an E3 region). In some embodiments, the adenovirus vectors of the invention contain an E3 sequence. Preferably, the adenovirus vector(s) is replication-competent, and, even more preferably, replicates preferentially in target cells. Inclusion of an E3 region (or E3 sequence, or portion of an E3 region) is contrary to the teachings of the prior art, which clearly indicated that deletion, not inclusion, of E3 would be desirable in this context (i.e., conferring cell-specific cytotoxicity) due to E3's ability to dampen host cytotoxic response against infected cells. Moreover, the prior art teaching and emphasis that E3 is not necessary for viral replication indicates non-inclusion of E3 for replication-competent adenoviral vectors.

We have found that these vectors maintain their high level of specificity and are (a) significantly more cytotoxic; and/or (b) produce higher virus yield including extracellular virus yield; and/or (c) form larger plaques; and/or (d) produce rapid cell death; and/or (e) kill tumors or suppress tumor growth more efficiently in vivo than vectors lacking the E3 region. In addition, these vectors are target cell-specific, i.e., they comprise a target cell-specific transcriptional regulatory element, such as a cell type- or cell status-specific transcriptional regulatory element(s) (TRE), that preferably drive an adenovirus gene essential for propagation, preferably one or more early genes. The vectors of the invention are useful for exerting selective cytotoxicity and/or suppressing cell growth (including tumor growth). This is especially useful in the cancer context, in which targeted cell killing is desirable. This is also useful for targeted cytotoxic effects in other, non-tumor cells, when selective destruction and/or suppression of these cells is desirable. The vectors can also be useful for detecting the presence of cells which permit function of a target cell-specific TRE in, for example, an appropriate biological (such as clinical) sample. Further, the adenovirus vector(s) can optionally selectively produce one or more proteins of interest in a target cell by using a heterologous, i.e., non-adenoviral, TRE.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987, and periodic updates); "PCR: The Polymerase Chain Reaction", (Mullis et al., eds., 1994); "Current Protocols in Immunology" (J. E. Coligan et al., eds., 1991).

For techniques related to adenovirus, see, inter alia, Felgner and Ringold (1989) *Nature* 337:387–388; Berkner and Sharp (1983) *Nucl. Acids Res.* 11:6003–6020; Graham (1984) *EMBO J.* 3:2917–2922; Bett et al. (1993) *J. Virology* 67:5911–5921; Bett et al. (1994) *Proc. Natl. Acad. Sci. USA* 91:8802–8806.

Definitions

An "E3 region" (used interchangeably with "intact E3 region") is a term well understood in the art and means the region of the adenoviral genome that encodes the E3 products (discussed herein). Generally, the E3 region is located between about 28583 and about 30470 of the adenoviral genome. An E3 region (or E3 sequence, defined below) for use in the present invention may be from any adenovirus serotype. The E3 region has been described in various publications, including, for example, Wold et al. (1995) *Curr. Topics Microbiol. Immunol.* 199:237–274.

An "E3 sequence" is a polynucleotide sequence that contains a sequence from an E3 region and excludes a sequence encoding only ADP. Thus, an E3 sequence can include ADP, as long as another portion of the E3 region is included. As is well known in the art, the ADP coding region is located in the E3 region within the adenoviral genome from about 29468 bp to about 29773 bp; including the Y leader, the location of ADP is from about 28375 bp to about 29773 bp for Ad5. Other ADP regions for other serotypes are known in the art. An E3 sequence includes, but is not limited to, deletions; insertions; fusions; and substitutions. An E3 sequence may also comprise an E3 region or a portion of the E3 region. It is understood that, as an "E3 sequence" is not limited to an "E3 region", alternative references herein to an "E3 region" or "E3 sequence" do not indicate that these terms are interchangeable. Assays for determining a functional E3 sequence for purposes of this invention are described herein.

An "E3 containing" vector of the invention refers to any of the embodiments described herein.

A "portion" of the E3 region means less than the entire E3 region, and as such includes polynucleotide deletions as well as polynucleotides encoding one or more polypeptide products of the E3 region. For purposes of this invention, when a "portion" of E3 region includes a polynucleotide encoding ADP, that portion includes at least one other E3 polypeptide product, or a functional fragment of an E3 polypeptide product.

As used herein, a "transcriptional regulatory element", or "TRE" is a polynucleotide sequence, preferably a DNA sequence, that regulates (i.e., controls) transcription of an operably-linked polynucleotide sequence by an RNA polymerase to form RNA. As used herein, a TRE increases transcription of an operably linked polynucleotide sequence in a host cell that allows the TRE to function. The TRE comprises an enhancer element and/or promoter element, which may or may not be derived from the same gene. The promoter and enhancer components of a TRE may be in any orientation and/or distance from the coding sequence of interest, and comprise multimers of the foregoing, as long as the desired transcriptional activity is obtained. As discussed herein, a TRE may or may not lack a silencer element.

As used herein, the term "target cell-specific TRE" is intended to mean that the TRE sequences to which a gene, which may be a gene essential for replication of an adenoviral vector, is operably linked, or to which a transgene is operably linked, functions specifically in that target cell so that transcription (and replication, if the operably linked gene is one essential for adenovirus replication) selectively or preferentially proceeds (i.e., when compared to a non-target cell) in that target cell, or so that a transgene polynucleotide is expressed in that target cell. This can occur by virtue of the presence in that target cell, and not in non-target cells (or significantly less so, or in inactive or less active forms, in non-target cells), of transcription factors that activate transcription driven by the operably linked transcriptional control sequences. It can also occur by virtue of the absence of transcription inhibiting factors that normally occur in non-target cells and prevent transcription driven by the operably linked transcriptional control sequences. "Target cell-specific TRE" includes cell type-specific and cell status-specific TRE, as well as "composite" TREs. The term "composite TRE" includes a TRE which comprises both a cell type-specific and a cell status-specific TRE. A target cell-specific TRE can also include a heterologous component, including, for example, an SV40 or a cytomegalovirus (CMV) promoter(s).

A "cell type-specific TRE" is preferentially functional, i.e., confers transcriptional activation, in a specific type of cell relative to other types of cells of different functionality. "Cell type" is a reflection of a differentiation state of a cell which is, under normal physiological conditions, an irreversible, end-stage state. For example, a prostate-specific antigen TRE is functional in prostate cells, but is not substantially, or significantly, functional in other cell types such as hepatocytes, astrocytes, cardiocytes, lymphocytes, etc. Generally, a cell type-specific TRE is active in only one cell type. When a cell type-specific TRE is active in more than one cell type, its activity is restricted to a limited number of cell types, i.e., it is not active in all cell types. A cell type-specific TRE may or may not be tumor cell specific. The term "cell type-specific", as used herein, is intended to include cell type specificity, tissue specificity, as well as specificity for a cancerous state of a given target cell type. In the latter case, specificity for a cancerous state of a normal cell is in comparison to a normal, non-cancerous counterpart.

As used herein, the term "cell status-specific TRE" is preferentially functional, i.e., confers transcriptional activation on an operably linked polynucleotide in a cell which allows a cell status-specific TRE to function, i.e., a cell which exhibits a particular physiological condition, including, but not limited to, an aberrant physiological state. "Cell status" thus refers to a given, or particular, physiological state (or condition) of a cell, which is reversible and/or progressive. The physiological state may be generated internally or externally; for example, it may be a metabolic state (such as in response to conditions of low oxygen), or it may be generated due to heat or ionizing radiation. "Cell status" is distinct from a "cell type", which relates to a differentiation state of a cell, which under normal conditions is irreversible. Generally (but not necessarily), as discussed herein, a cell status is embodied in an aberrant physiological state, examples of which are given below.

A "normal cell status" or "normal physiological state" is the status of a cell which exists in normal physiological conditions and which is non-dividing or divides in a regulated manner, i.e., a cell in a normal physiological state.

"Normal physiological conditions" are known to those skilled in the art. These conditions may vary, depending on a cell's location in the body. For example, oxygen tension can vary from tissue to tissue. For in vitro analyses for the purposes of determining whether a TRE is responsive to deviations from normal physiological conditions, these conditions generally include an oxygen concentration of about 20% $O_2$, and a temperature of about 37° C. "Regulated cell division" is a term well understood in the art and refers to the normal mitotic activity of a cell. Those skilled in the art understand that normal mitotic activity varies from cell type to cell type. For example, many terminally differentiated cells in tissues exhibit little or no mitotic activity, while hematopoietic cells are generally mitotically active.

The terms "aberrant cell status" and "aberrant physiological state", used interchangeably herein, intend a condition of a cell which is a response to, a result of, or is influenced by, an aberrant physiological condition. An aberrant cell status is neither cell type-specific nor tissue type-specific. An aberrant cell status is defined in relation to a cell of the same type which is in a non-dividing/regulated dividing state and under normal physiological conditions. An "aberrant physiological condition" or "aberrant physiological state", as used herein, intends a condition which deviates from normal physiological conditions, and includes, but is not limited to, a physiological condition that is characterized by alterations in oxygen concentration, such as hypoxic conditions; temperatures which deviate from physiological temperatures; a condition that triggers apoptosis; radiation, including ionizing radiation and UV irradiation; de-regulated cell division, resulting for example, from a lack of, or insufficient amounts of, or inactivity of, a factor which controls cell division, such as, for example, retinoblastoma protein (Rb); variations in timing of cell cycle; infection with a pathogen; exposure to a chemical substance; or a combination of the above-listed conditions. Another example is a mutation that could, or does, exist in any cell type, i.e., its existence does not depend on, or is not related to, the differentiation state of the cell.

A "target cell", as used herein, is one that allows, permits or induces the function of a target cell-specific TRE such that it effects transcriptional activation (and/or enhancement), i.e., increases the level of transcription, of an operably linked polynucleotide. Target cell-specific TREs include cell type-specific TREs and cell status-specific TREs. Preferably, a target cell is a mammalian cell, preferably a human cell. A target cell may or may not be neoplastic.

"A target cell type which allows a TRE to function" or a cell in which the function of a TRE is "sufficiently preserved" or "functionally preserved", or "a cell in which a TRE is functional" is a cell in which the TRE, when operably linked to a promoter (if not included in the TRE) and a reporter gene, increases expression of the reporter gene at least about 2-fold, preferably at least about 5-fold, preferably at least about 10-fold, more preferably at least about 20-fold, more preferably at least about 50-fold, more preferably at least about 100-fold, more preferably at least about 200-fold, even more preferably at least about 400- to about 500-fold, even more preferably at least about 1000-fold, when compared to the expression of the same reporter gene when not operably linked to said TRE. In the context of cell type-specific TREs, a "target cell" is a cell type which allows the function of a cell type-specific TRE. Accordingly, in the context of a cell type-specific TRE, comparison is further made between expression of the reporter gene when operably linked to the cell type-specific TRE when in a target cell type versus when in a different cell type. In the context of cell status-specific TREs, a "target cell" is one which exhibits a given requisite physiological (or environmental) state, which may be an aberrant physiological state. Accordingly, in the context of a cell status-specific TRE, comparison is further made between expression of the reporter when operably linked to a cell status-specific TRE in the target cell in a given physiological state (which may be an aberrant physiological state) versus the same cell when in a normal physiological state (or a physiological state different from the given physiological state). Methods for measuring levels (whether relative or absolute) of expression are known in the art and are described herein.

A "functionally-preserved variant" of a target cell-specific TRE is a target cell-specific TRE which differs from another target cell-specific TRE, but still retains target cell-specific transcription activity, although the degree of activation may be altered (as discussed below). The difference in a target cell-specific TRE can be due to differences in linear sequence, arising from, for example, single base mutation(s), addition(s), deletion(s), and/or modification(s) of the bases. The difference can also arise from changes in the sugar(s), and/or linkage(s) between the bases of a target cell-specific TRE.

As used herein, a TRE derived from a specific gene is referred to by the gene from which it was derived and is a polynucleotide sequence which regulates transcription of an operably linked polynucleotide sequence in a host cell that expresses said gene. For example, as used herein, a "human glandular kallikrein transcriptional regulatory element", or "hKLK2-TRE" is a polynucleotide sequence, preferably a DNA sequence, which increases transcription of an operably linked polynucleotide sequence in a host cell that allows an hKLK2-TRE to function, such as a cell (preferably a mammalian cell, even more preferably a human cell) that expresses androgen receptor, such as a prostate cell. An hKLK2-TRE is thus responsive to the binding of androgen receptor and comprises at least a portion of an hKLK2 promoter and/or an hKLK2 enhancer (i.e., the ARE or androgen receptor binding site).

As used herein, a "probasin (PB) transcriptional regulatory element", or "PB-TRE" is a polynucleotide sequence, preferably a DNA sequence, which selectively increases transcription of an operably-linked polynucleotide sequence in a host cell that allows a PB-TRE to function, such as a cell (preferably a mammalian cell, more preferably a human cell, even more preferably a prostate cell) that expresses androgen receptor. A PB-TRE is thus responsive to the binding of androgen receptor and comprises at least a portion of a PB promoter and/or a PB enhancer (i.e., the ARE or androgen receptor binding site).

As used herein, a "prostate-specific antigen (PSA) transcriptional regulatory element", or "PSA-TRE", or "PSE-TRE" is a polynucleotide sequence, preferably a DNA sequence, which selectively increases transcription of an operably linked polynucleotide sequence in a host cell that allows a PSA-TRE to function, such as a cell (preferably a mammalian cell, more preferably a human cell, even more preferably a prostate cell) that expresses androgen receptor. A PSA-TRE is thus responsive to the binding of androgen receptor and comprises at least a portion of a PSA promoter and/or a PSA enhancer (i.e., the ARE or androgen receptor binding site).

As used herein, a "carcinoembryonic antigen (CEA) transcriptional regulatory element", or "CEA-TRE" is a polynucleotide sequence, preferably a DNA sequence, which selectively increases transcription of an operably linked polynucleotide sequence in a host cell that allows a CEA-TRE to function, such as a cell (preferably a mammalian cell, even more preferably a human cell) that expresses CEA. The CEA-TRE is responsive to transcription factors and/or co-factor(s) associated with CEA-producing cells and comprises at least a portion of the CEA promoter and/or enhancer.

As used herein, an "α-fetoprotein (AFP) transcriptional regulatory element", or "AFP-TRE" is a polynucleotide sequence, preferably a DNA sequence, which selectively increases transcription (of an operably linked polynucleotide sequence) in a host cell that allows an AFP-TRE to function, such as a cell (preferably a mammalian cell, even more preferably a human cell) that expresses AFP. The AFP-TRE is responsive to transcription factors and/or co-factor(s) associated with AFP-producing cells and comprises at least a portion of the AFP promoter and/or enhancer.

As used herein, an "a mucin gene (MUC) transcriptional regulatory element", or "MUC1-TRE" is a polynucleotide sequence, preferably a DNA sequence, which selectively increases transcription (of an operably-linked polynucleotide sequence) in a host cell that allows a MUC1-TRE to function, such as a cell (preferably a mammalian cell, even more preferably a human cell) that expresses MUC1. The MUC1-TRE is responsive to transcription factors and/or co-factor(s) associated with MUC1-producing cells and comprises at least a portion of the MUC1 promoter and/or enhancer.

An "adenovirus vector" or "adenoviral vector" (used interchangeably) comprises a polynucleotide construct of the invention. A polynucleotide construct of this invention may be in any of several forms, including, but not limited to, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, and complexed with compounds such as PEG to immunologically "mask" the molecule and/or increase half-life, and conjugated to a nonviral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent in a target cell.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. Peyrottes et al. (1996) *Nucleic Acids Res.* 24: 1841–8; Chaturvedi et al. (1996) *Nucleic Acids Res.* 24: 2318–23; Schultz et al. (1996) *Nucleic Acids Res.* 24: 2966–73. A phosphorothiate linkage can be used in place of a phosphodiester linkage. Braun et al. (1988) *J. Immunol.* 141: 2084–9; Latimer et al. (1995) *Mol. Immunol.* 32: 1057–1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in *Current Protocols in Molecular Biology* (F. M. Ausubel et al., eds., 1987) Supplement 30, section 7.7.18, Table 7.7.1. A preferred alignment program is ALIGN Plus (Scientific and Educational Software, Pennsylvania), preferably using default parameters, which are as follows: mismatch=2; open gap=0; and extend gap=2. Another preferred program is the BLAST program for alignment of two nucleotide sequences, using default parameters as follows: open gap=5; extension gap—2 penalties; gap×dropoff=50; expect=10; word size=11. The BLAST program is available at the following Internet address: http://www.ncbi.nlm.nih.gov.

A "replication competent" adenoviral vector or adenovirus is a term well-understood in the art and means that the adenoviral vector is able to replicate, or propagate. "Replication" and "propagation" are defined herein.

"Under transcriptional control" is a term well understood in the art and indicates that transcription of a polynucleotide sequence, usually a DNA sequence, depends on its being operably (operatively) linked to an element which contributes to the initiation of, or promotes, transcription. "Operably linked" refers to a juxtaposition wherein the elements are in an arrangement allowing them to function.

As used herein, "cytotoxicity" is a term well understood in the art and refers to a state in which a cell's usual biochemical or biological activities are compromised (i.e., inhibited). These activities include, but are not limited to, metabolism; cellular replication; DNA replication; transcription; translation; uptake of molecules. "Cytotoxicity" includes cell death and/or cytolysis. Assays are known in the art which indicate cytotoxicity, such as dye exclusion, $^3$H-thymidine uptake, and plaque assays.

The term "selective cytotoxicity", as used herein, refers to the cytotoxicity conferred by an adenovirus vector of the present invention on a cell which allows or induces a target cell-specific TRE to function (a target cell) when compared to the cytotoxicity conferred by an adenoviral vector of the present invention on a cell which does not allow a target cell-specific TRE to function (a non-target cell). Such cytotoxicity may be measured, for example, by plaque assays, by reduction or stabilization in size of a tumor comprising target cells, or the reduction or stabilization of serum levels of a marker characteristic of the tumor cells, or a tissue-specific marker, e.g., a cancer marker, such as prostate specific antigen.

In the context of adenovirus or adenovirus vector, a "heterologous polynucleotide" or "heterologous gene" or "transgene" (used interchangeably) is any polynucleotide or gene that is not present in wild-type adenovirus. Preferably, the transgene will also not be expressed or present in the target cell prior to introduction by the adenovirus vector. Examples of preferred transgenes are provided below.

In the context of adenovirus or adenovirus vector, a "heterologous" promoter or enhancer or TRE is one which is not associated with or derived from an adenovirus gene. In the context of adenovirus or adenovirus vector, a "heterologous target cell-specific TRE" is a target cell-specific TRE which is not associated with or derived from an adenovirus gene.

In the context of adenovirus or adenovirus vector, an "endogenous" promoter, enhancer, or TRE is native to or derived from adenovirus.

In the context of a target cell-specific TRE, a "heterologous" promoter or enhancer is one which is not normally associated in a cell with or derived from the target cell-specific TRE. Examples of a heterologous promoter or enhancer are the albumin promoter or enhancer and other viral promoters and enhancers, such as SV40 or CMV, or cell type specific TREs such as a prostate specific TRE (for example, a prostate specific TRE is heterologous with respect to a liver cell specific TRE).

"Suppressing" tumor growth indicates a growth state that is curtailed when compared to growth without contact with, i.e., transfection by, an adenoviral vector described herein. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage.

As used herein, the terms "neoplastic cells", "neoplasia", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign.

A "host cell" includes an individual cell or cell culture which can be or has been a recipient of an adenoviral vector(s) of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with an adenoviral vector of this invention.

"Replication" and "propagation" are used interchangeably and refer to the ability of an adenovirus vector of the invention to reproduce or proliferate. These terms are well understood in the art. For purposes of this invention, replication involves production of adenovirus proteins and is generally directed to reproduction of adenovirus. Replication can be measured using assays standard in the art and described herein, such as a burst assay, plaque assay, or a one-step growth curve. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

"Replicating preferentially" means that the adenovirus replicates more in a target cell than in a non-target cell. Preferably, the adenovirus replicates at least about 10%, more preferably at least about 25%, more preferably at least about 50%, more preferably at least about 100% (i.e., 2-fold) higher, preferably at least about 5-fold higher, more preferably at least about 10-fold higher, still more preferably at least about 50-fold higher, even more preferably at least about 100-fold higher, still more preferably at least about 400-fold to about 500-fold higher, still more preferably at least about 1000-fold higher, most preferably at least about $1\times10^6$ higher.

A polynucleotide sequence that is "depicted in" a SEQ ID NO means that the sequence is present as, or contained within an identical contiguous sequence in the SEQ ID NO. The term encompasses portions, or regions of the SEQ ID NO as well as the entire sequence contained within the SEQ ID NO.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, farm animals, sport animals, rodents, primates, and pets.

An "effective amount" is an amount sufficient to effect beneficial or desired results, including clinical results. An effective amount can be administered in one or more administrations. In the context of a disease state, an effective amount of an adenoviral vector is an amount that is sufficient to palliate, ameliorate, stabilize, reverse, slow or delay the progression of the disease state.

E3-containing Target Cell-specific Adenoviral Vectors

The invention provides target cell-specific adenovirus vectors comprising an E3 sequence and an adenoviral gene under transcriptional control of a target cell-specific TRE. Preferably, the vectors are replication-competent. Even more preferably, the adenoviral gene under transcriptional control of a target cell-specific TRE is one essential for adenoviral replication. Inclusion of the E3 region of adenovirus was found to enhance cytotoxicity of the target cell-specific adenoviral vectors of the present invention.

E3-containing adenoviral vectors of the invention (including adenoviral vectors containing E3 sequences and/or a portion of E3) maintain their high level of specificity and display one or more of the following characteristics relative to adenoviral vectors lacking an E3 region (or portion of E3), i.e., they (a) are more cytotoxic; (b) produce higher virus yield, including intracellular and extracellular virus yield; (c) form larger plaques; (d) produce rapid cell death; (e) kill tumors more efficiently in vivo; and/or (D suppress tumor growth more efficiently in vivo. Any detectable increase is sufficient, although preferably any of these characteristics may be increased (when compared to adenoviral vectors lacking E3) at least about 10%, more preferably at least about 25%, more preferably at least about 50%, more preferably at least about 100% (i.e., 2-fold), more preferably at least about 5-fold, more preferably at least about 10-fold, more preferably at least about 20-fold or more. In some embodiments, cytotoxicity of an E3-containing adenoviral vector of the invention is increased when compared to the cytotoxicity of an adenoviral counterpart lacking E3. It is understood that an E3-containing adenoviral vector of the invention can exhibit the aforementioned increased level(s) of activity with respect to one or more of these characteristics, to the same or different degree relative to an adenoviral counterpart lacking E3. For example, a given E3-containing adenoviral vector may exhibit 2-fold greater cytotoxicity, yet produce a 3-fold higher virus yield than an adenoviral counterpart lacking E3.

Cytotoxicity can be measured by any known method, including, but not limited to, an MTT assay and trypan blue dye exclusion, both of which are described in Example 2. Virus yield can be measured by any known method, including, but not limited to, plaque assay on a cell line permissive for adenoviral replication, as described in Example 2. Whether a given E3-containing adenovirus vector forms larger plaques than a counterpart vector lacking E3 can be determined, for example, by plaque assay and measuring plaque diameter. Whether a given E3-containing adenovirus vector produces rapid cell death relative to a counterpart adenovirus vector lacking E3 can be determined using any known method, including, but not limited to, MTT assay or trypan blue exclusion assay performed over a suitable course of time post-infection, such as 1, 2, 3, 5, or 7 or more days post-infection. Tumor killing and suppression of tumor cell growth can be measured by any known method, including, but not limited to, a tumor xenograft assay as described in Example 2.

It is understood that, for purposes of this invention, not only may an (intact) E3 region or a portion of an E3 region be used, but E3 sequences (which include other forms and arrangements of E3) may be employed, including, but not limited to, deletions; internal deletions; fusions comprising E3 or a portion of E3; insertions (whereby one or more nucleotides are inserted within an E3 sequence); and substitutions, including silent substitutions, as well as substitutions resulting in one or more differences in an amino acid sequence(s). A functional E3 squence may be determined by assaying, for example, for any of the characteristics listed above.

The adenoviral vectors of this invention contain an E3 sequence, which may be an intact E3 region or a portion of an E3 region. It is understood that, as inclusion of E3 confers observable and measurable functionality on the adenoviral vectors, for example, increased replication and production, functionally equivalent (in which functionality is essentially maintained, preserved, or even enhanced or diminished) variants of E3 may be constructed. Functional equivalents of an E3 region include those in which one or more E3 functions is essentially maintained, preserved, or even enhanced or diminished which confer one or more of the following properties on the virus: (a) cytotoxicity; (b) production of virus yield, including intracellular and extracellular virus yield; (c) plaque formation; and (d) production of cell death; (e) killing and/or suppressing of tumors in vivo. For example, portions of E3 may be used. As is explained in the definition of "portion" of E3, a portion may be, non-inclusively, either of the following: (a) deletion, preferably at the 3' end; (b) inclusion of one or more various open reading frames of E3. Five proteins which are encoded by the Ad-E3 region have been identified and characterized: (1) a 19-kDa glycoprotein (gp19k) is one of the most abundant adenovirus early proteins, and is known to inhibit transport of the major histocompatibility complex class I molecules to the cell surface, thus impairing both peptide recognition and clearance of Ad-infected cells by cytotoxic T lymphocytes (CTLs); (2) E3 14.7k protein and the E3 10.4k/14.5k complex of proteins inhibit the cytotoxic and inflammatory responses mediated by tumor necrosis factor (TNF); (3) E3 10.4k/14.5k protein complex downregulates the epidermal growth factor receptor, which may inhibit inflammation and activate quiescent infected cells for efficient virus replication; (4) E3 11.6k protein (adenoviral death protein, ADP) from adenovirus 2 and 5 appears to promote cell death and release of virus from infected cells. The functions of three E3-encoded proteins—3.6k, 6.7k and 12.5k—are unknown. A ninth protein having a molecular weight of 7.5 kDa has been postulated to exist, but has not been detected in cells infected with wild-type adenovirus. Wold et al. (1995) *Curr. Topics Microbiol. Immunol.* 199:237–274. The E3 region is schematically depicted in FIG. 1. These intact, portions, or variants of E3 may be readily constructed using standard knowledge and techniques in the art. Preferably, an intact E3 region is used. Appropriate vectors comprising an intact E3 region are commercially available, e.g., from Microbix. In other embodiments, an E3 region isused which lacks the 10.4k/14.5k complex and the 14.7 protein (i.e., deletion of about bp 29781 to about bp 30847). E3 sequences or portions of E3 can be derived from such vectors using standard techniques of molecular biology, such as restriction and ligation, and polymerase chain reactions. Any of the various serotypes of adenovirus can be used in the present invention, such as Ad2, Ad5, Ad12 and Ad40. For purposes of illustration, serotype Ad5 is exemplified herein.

In the adenovirus vectors of the present invention, E3 (i.e., E3 sequence, which includes E3 region or portion of an E3 region) may or may not be under transcriptional control of native adenoviral transcriptional control element(s). The E3 promoter is located within the coding sequence for virion protein VIII, an essential protein which is highly conserved among adenovirus serotypes. In some embodiments, E3 is under transcriptional control of a heterologous TRE, including, but not limited to, a target cell-specific TRE. In one embodiment, the invention provides an adenoviral vector, preferably replication competent, that comprises an E3 sequence under transcriptional control of a target-cell specific TRE. A number of target cell-specific TREs are known in the art, several of which are described in more detail herein. In other embodiments, the E3 region is under transcriptional control of a target cell-specific TRE, and the vector further comprises an adenoviral gene essential for replication under transcriptional control of a target cell-specific TRE.

Target Cell-specific TREs

Adenoviral vectors of the present invention include, in addition to an E3 sequence, one or more adenoviral genes under transcriptional control of a target cell-specific TRE, and optionally include a transgene, which may also be under transcriptional control of a target cell-specific TRE or other TRE. Preferably, the adenovirus gene(s) under transcriptional control of a target cell-specific TRE is essential for propagation, preferably an early gene(s), such as E1A, E1B, and/or E4. When the adenovirus vector(s) is selectively (i.e., preferentially) replication competent for propagation in target cells, these cells will be preferentially killed upon adenoviral proliferation. Once the target cells are destroyed due to selective cytotoxic and/or cytolytic replication, the adenovirus vector replication is significantly reduced, thus lessening the probability of runaway infection and undesirable bystander effects. In vitro cultures may be retained to monitor the mixture (such as, for example, a biopsy or other appropriate biological sample) for occurrence (i.e., presence) and/or recurrence of the target cell, e.g., a neoplastic cell or other undesired cell. To further ensure cytotoxicity, one or more transgenes having a cytotoxic effect may also be present and under selective transcriptional control. In this embodiment, one may provide higher confidence that the target cells will be destroyed. Target cell-specific TREs include cell type-specific TREs and cell status-specific TREs, either of which may be specific for a neoplastic cell. Alternatively, an adenovirus gene, and optionally, a transgene, can be under transcriptional control of a cell type-specific and a cell status-specific TRE. Such target cell-specific TREs are termed "composite" target cell-specific TREs herein.

Target cell-specific TREs for use in the adenoviral vectors of the present invention can be derived from any species, preferably a mammal. A number of genes have been described which are expressed preferentially in specific cell types. Any of these cell type-specific genes can be used to generate a cell type-specific TRE. Similarly, a number of genes have been described which are expressed in response to, or in association with, a cell status. Any of these cell status-associated genes may be used to generate a cell status-specific TRE.

A target cell-specific TRE may or may not lack a silencer. The presence of a silencer (i.e., a negative regulatory element) may assist in shutting off transcription (and thus replication) in non-permissive cells (i.e., cell in a normal cell state). Thus, presence of a silencer may confer enhanced target cell-specific replication by more effectively preventing adenoviral vector replication in non-target cells. Alternatively, lack of a silencer may assist in effecting replication in target cells, thus conferring enhanced target cell-specific replication due to more effective replication in target cells.

A target cell-specific TRE can comprise multimers, for example, a tandem series of at least two, at least three, at least four, or at least five target cell-specific response elements. These multimers may also contain heterologous promoter and/or enhancer sequences.

In some embodiments, an E3-containing adenoviral vector of the invention further comprises a first adenoviral gene under transcriptional control of a first target cell-specific TRE and a second gene under transcriptional control of a second target cell-specific TRE. In some of these embodiments, the first adenoviral gene is one essential for adenoviral replication. In other embodiments, the first and the second genes are adenoviral genes. In other embodiments, the first and the second genes are adenoviral genes essential for replication.

The first and the second target cell-specific TREs may or may not be substantially identical to one another. By "substantially identical" is meant a requisite degree of sequence identity between the two TREs. The degree of sequence identity between these TREs is at least about 80%, preferably at least about 85%, more preferably at least about 90%, even more preferably at least about 95%, even more preferably at least about 98%, and most preferably 100%.

Adenoviral constructs in which the first and second target cell-specific TREs are substantially identical, particularly if these TREs control transcription of early genes (such as E1A and E1B), may display an instability which may be desirable in certain contexts, such as when an automatic "self-destruction" property can shut down the virus, thereby controlling the degree of propagation. Conversely, more stable double (or more) constructs may be desirable in yet other contexts. In either case, we have observed that having multiple adenovirus genes essential for propagation (especially early genes, more particularly E1a and E1b), confers significant specificity to the vectors. In some embodiments, the first and second target cell-specific TREs are cell type-specific and are functional in the same cell type.

Sequence identity can be determined by a sequence comparison using, i.e., sequence alignment programs that are known in the art, such as those described in *Current Protocols in Molecular Biology* (F. M. Ausubel et al., eds., 1987) Supplement 30, section 7.7.18, Table 7.7.1 A preferred alignment program is ALIGN Plus (Scientific and Educational Software, Pennsylvania), preferably using default parameters, which are as follows: mismatch=2; open gap=0; and extend gap=2. Another preferred program is the BLAST program for alignment of two nucleotide sequences, using default parameters as follows: open gap=5; extension gap—2 penalties; gap x dropoff=50; expect=10; word size=11. The BLAST program is available at the following Internet address: http://www.ncbi.nlm.nih.gov. Alternatively, hybridization under stringent conditions can also indicate degree of sequence identity.

Hybridization reactions can be performed under conditions of different "stringency". Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water.

"$T_m$" is the temperature in degrees Celsius at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as:

$$T_m=81.5+16.6\log[X^+]+0.41(\%\ G/C)-0.61(\%\ F)-600/L$$

where $[X^+]$ is the cation concentration (usually sodium ion, $Na^+$) in mol/L; (% G/C) is the number of G and C residues as a percentage of total residues in the duplex; (% F) is the percent formamide in solution (wt/vol); and L is the number of nucleotides in each strand of the duplex.

Stringent conditions for both DNA/DNA and DNA/RNA hybridization are as described by Sambrook et al. *Molecular Cloning, A Laboratory Manual,* 2nd Ed., Cold Spring Harbor Laboratory Press, Cold Spring Harbor, N.Y., 1989, herein incorporated by reference. For example, see page 7.52 of Sambrook et al. An example of stringent hybridization conditions are 68° C., 0.2×SSC.

Accordingly, in some embodiments, the invention provides an adenoviral vector comprising, in addition to an E3 sequence, any of the following: (a) E1A under transcriptional control of a PB-TRE and E1B under transcriptional control of a PSA-TRE; (b) E1A under transcriptional control of an AFP-TRE and E1B under transcriptional control of a second (but not necessarily identical or non-identical) AFP-TRE; (c) E1A under transcriptional control of a CEA-TRE. As the discussion of possible TREs below makes clear, these are non-limiting examples of the possible combinations for the E3-containing vectors of the invention.

An example of an adenoviral vector comprising, in addition to an E3 sequence, E1A under transcriptional control of a PB-TRE and E1B under transcriptional control of a PSA-TRE is the construct CN787, the construction of which is described in detail in Example 1. An example of an adenoviral vector comprising, in addition to an E3 sequence, E1A under transcriptional control of an AFP-TRE and E1B under transcriptional control of a second (but not necessarily identical or non-identical) AFP-TRE is the construct CN790, which is described in Example 1. Examples of an adenoviral vector comprising, in addition to an E3 sequence, E1A under transcriptional control of a CEA-TRE are CN798 and CN799, which are described in detail in Example 1. Accordingly, the present invention encompasses, as specific embodiments, CN787, CN790, CN798, and CN799 (alternatively and interchangeably denoted CV787, CV790, CV798, and CV799).

In other embodiments, the adenoviral vector comprises an adenoviral gene essential for adenoviral replication under control of a first target cell-specific TRE, and a transgene under control of a second target cell-specific TRE. The first and the second target cell-specific TREs may or may not be substantially identical to one another.

Figure 19:
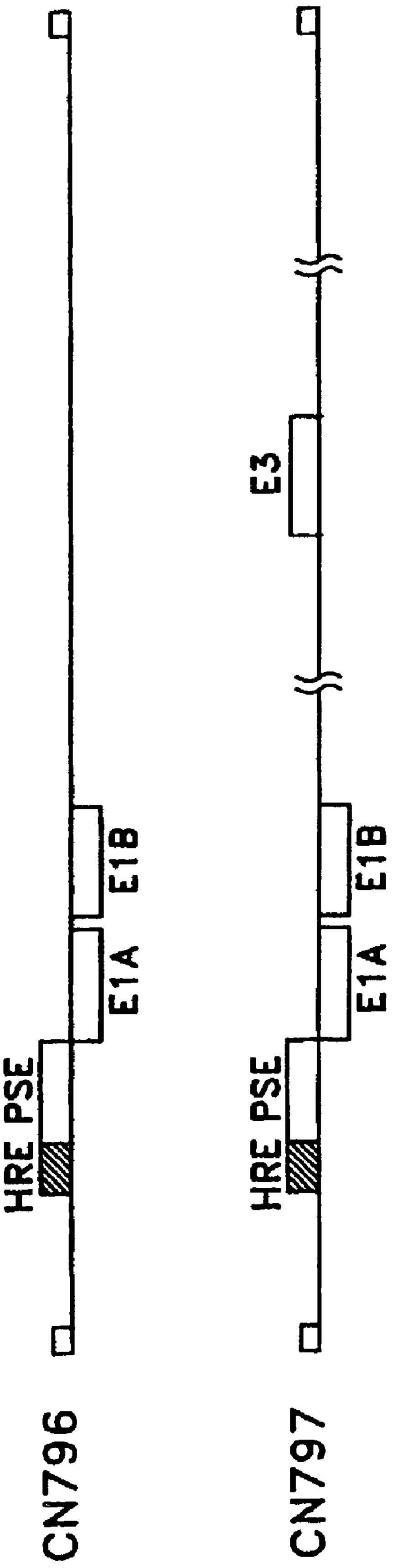
FIG. 19 is a schematic representation of CN796 and CN797.

In some embodiments, a target cell-specific TRE can comprise two or more different types of TREs. For example, a cell status-specific TRE can be juxtaposed with another TRE, such as a different cell status-specific TRE, or, alternatively, a cell type-specific TRE. "Juxtaposed" means a cell status-specific TRE and the second TRE transcriptionally control the same gene. For these embodiments, the cell status-specific TRE and the second TRE may be in any of a number of configurations, including, but not limited to, (a) next to each other (i.e., abutting); (b) both 5' to the gene that is transcriptionally controlled (i.e., may have intervening sequences between them); (c) one TRE 5' and the other TRE 3' to the gene. For example, as described in Example 1 and shown in FIG. 19, a cell type-specific TRE can be juxtaposed with a cell status-specific TRE to control transcription of an operably linked adenoviral gene. The construct CN797 is an example of an E3-containing adenoviral vector comprising the composite TRE described in Example 1. Accordingly, the present invention encompasses, as one embodiment, CN797 (alternatively and interchangeably denoted CV797). Such "composite" TREs can be used to confer both cell status- and cell type-specific expression of an operably linked polynucleotide, and thus may confer significantly greater specificity and/or efficacy. Examples of cell type-specific TREs are provided below. Alternatively, "composite" TREs can be used to confer different, and possibly synergistic, cell status and/or cell type specificity. For example, a composite cell status-specific TRE could confer specificity to hypoxia and heat shock. Example 1 provides a description of an E3-containing adenovirus construct comprising E1A and E1B genes under transcriptional control of a combination transcriptional regulatory element consisting of a hypoxia-responsive element (HRE) and a prostate-specific TRE, PSA-TRE. Accordingly, in one embodiment, an HRE comprises a 67-base fragment depicted in FIG. 20 (SEQ ID NO:7).

As is readily appreciated by one skilled in the art, a target cell-specific TRE is a polynucleotide sequence, and, as such, can exhibit function over a variety of sequence permutations. Methods of nucleotide substitution, addition, and deletion are known in the art, and readily available functional assays (such as the CAT or luciferase reporter gene assay) allow one of ordinary skill to determine whether a sequence variant exhibits requisite target cell-specific transcription function. Hence, the invention also includes functionally-preserved variants of the nucleic acid sequences disclosed herein, which include nucleic acid substitutions, additions, and/or deletions. While not wishing to be bound by a single theory, the inventors note that it is possible that certain modifications will result in modulated resultant expression levels, including enhanced expression levels. Achievement of modulated resultant expression levels, preferably enhanced expression levels, may be especially desirable in the case of certain, more aggressive forms of cancer, or when a more rapid and/or aggressive pattern of cell killing is warranted (due to an immunocompromised condition of the individual, for example).

The activity of a TRE generally depends upon the presence of transcriptional regulatory factors and/or the absence of transcriptional regulatory inhibitors. Transcriptional activation can be measured in a number of ways known in the art (and described in more detail below), but is generally measured by detection and/or quantitation of mRNA or the protein product of the coding sequence under control of (i.e., operatively linked to) the TRE. As discussed herein, a TRE can be of varying lengths, and of varying sequence composition.

Certain point mutations within sequences of TREs have been shown to decrease transcription factor binding and gene activation. One of skill in the art would recognize that some alterations of bases in and around known the transcription factor binding sites are more likely to negatively affect gene activation and cell-specificity, while alterations in bases which are not involved in transcription factor binding are not as likely to have such effects. Certain mutations are also capable of increasing TRE activity. Testing of the effects of altering bases may be performed in vitro or in vivo by any method known in the art, such as mobility shift assays, or transfecting vectors containing these alterations in TRE functional and TRE non-functional cells. Additionally, one of skill in the art would recognize that point mutations and deletions can be made to a TRE sequence without altering the ability of the sequence to regulate transcription.

As an example of how target cell-specific TRE activity can be determined, a polynucleotide sequence or set of such sequences can be generated using methods known in the art, such as chemical synthesis, site-directed mutagenesis, PCR, and/or recombinant methods. The sequence(s) to be tested is inserted into a vector containing an appropriate reporter gene, including, but not limited to, chloramphenicol acetyl transferase (CAT), β-galactosidase (encoded by the lacZ gene), luciferase (encoded by the luc gene), green fluorescent protein, alkaline phosphatase, and horse radish peroxidase. Such vectors and assays are readily available, from, inter alia, commercial sources. Plasmids thus constructed are transfected into a suitable host cell to test for expression of the reporter gene as controlled by the putative target cell-specific TRE using transfection methods known in the art, such as calcium phosphate precipitation, electroporation, liposomes (lipofection), and DEAE-dextran. Suitable host cells include any cell type, including but not limited to, Hep3B, Hep G2, HuH7, HuH1/C12, LNCaP, HBL-100, Chang liver cells, MCF-7, HLF, HLE, 3T3, HUVEC, and HeLa. For a TRE suspected to be a cell status-specific TRE, host cells transfected with the TRE-reporter gene construct to be tested are subjected to conditions which result in a change in cell status (for example, one which result in an aberrant physiological state). The same cells not subjected to these conditions, i.e., which are under normal physiological conditions and therefore in a normal physiological state, serve as controls. Results are obtained by measuring the level of expression of the reporter gene using standard assays. Comparison of expression between cells in a particular state and control indicates presence or absence of transcriptional activation. Generally, to determine cell specific activity of a TRE, the TRE-reporter gene constructs are introduced into a variety of cell types. The amount of TRE activity is determined in each cell type and compared to that of a reporter gene construct without the TRE. A TRE is cell specific when it is preferentially functional in a specific type of cell over a different type of cell. "Transcriptional activation" has been defined above.

Comparisons between or among various target cell-specific TREs can be assessed, for example, by measuring and comparing levels of expression within a single cell line under normal and aberrant physiological conditions (for cell status-specific TREs) or within a single cell line of the appropriate cell type (for cell type-specific TREs). These comparisons may also be made by measuring and comparing levels of expression within a single cell line. It is understood that absolute transcriptional activity of a target cell-specific TRE will depend on several factors, such as the nature of the target cell, delivery mode and form of the target cell-specific TRE, and the coding sequence that is to be selectively transcriptionally activated. To compensate for various plasmid sizes used, activities can be expressed as relative activity per mole of transfected plasmid. Alternatively, the level of transcription (i.e., mRNA) can be measured using standard Northern analysis and hybridization techniques. Levels of transfection (i.e., transfection efficiencies) are measured by co-transfecting a plasmid encoding a different reporter gene under control of a different TRE, such as the cytomegalovirus (CMV) immediate early promoter. This analysis can also indicate negative regulatory regions, i.e., silencers.

As an example of how hypoxia induction can be measured, one can use an assay such as that described in Jiang et al. (1997) *Cancer Research* 57:5328–5335 or Dachs et al. (1997) *Nature Med.* 3:515–520. For example, a construct comprising a putative HRE, or multiple tandem copies thereof, together with a minimal promoter element, operably linked and controlling transcription of a polynucleotide which encodes a protein which is detectable or can be used to give a detectable signal, is introduced into host cells. The host cells are then subjected to conditions of normoxia (e.g., 20% $O_2$), and varying degrees of hypoxia, such as 5%, 2%, 1%, 0.1%, or less, $O_2$. The expression product of the operably linked polynucleotide (reporter gene) is then measured.

As an example of how a prostate cell-specific TRE activity, such as a PSA-TRE, can be determined, a polynucleotide sequence or set of such sequences can be generated using methods known in the art, such as chemical synthesis, site-directed mutagenesis, PCR, and/or recombinant methods. The sequence(s) to be tested can be inserted into a vector containing an appropriate reporter gene encoding a reporter protein, as described above. Plasmids thus constructed are transfected into a suitable host cell to test for expression of the reporter gene as controlled by the putative PSA-TRE using transfection methods known in the art, such as calcium phosphate precipitation, electroporation, liposomes (lipofection), and DEAE dextran. Suitable host cells include any cell type that produces androgen receptor, including but not limited to, prostate cells, including prostate tumor cells such as LNCaP. A gene encoding androgen receptor can be transformed into and expressed in any cell that does not normally express AR; in such a cell, a PSA-TRE will be functional. Non-androgen receptor producing cells, such as HLF, HLE, and 3T3 and the non-AR-producing prostate cancer cells PC3 and DU145 can be used as a control. Results are obtained by measuring the level of expression of the reporter gene using standard assays. The comparison of reporter gene expression between AR-producing cells and the control cell indicates the presence, absence, and/or degree of transcriptional activation.

Alternatively a putative cell status-specific TRE can be assessed for its ability to confer adenoviral replication preference for cells exhibiting the requisite physiological state, such as heat or ionizing radiation. For this assay, constructs containing an adenovirus gene essential to replication operably linked to a putative cell status-specific TRE are transfected into cells which exhibit the requisite physiological state. Viral replication in those cells is compared, for example, to viral replication by the construct in cells under normal physiological conditions (i.e., not exhibiting the requisite physiological state).

When a target cell-specific TRE is used with an adenovirus gene that is essential for propagation replication, competence is preferentially achievable in the target cell type and/or the target cell exhibiting a particular cell status.

Cell Type-specific TREs

In some embodiments, the E3-containing adenoviral vectors of the invention comprise a cell type-specific TRE, such as a prostate cell-specific TRE, a liver cell-specific TRE, a breast cancer cell-specific TRE, or a colon cancer cell-specific TRE. A cell type-specific TRE is preferentially functional in a specific type of cell relative to other types of cells of different functionality. For example, TREs that function preferentially in prostate cells (i.e., are prostate cell-specific) include, but are not limited to, TREs derived from the prostate-specific antigen gene (PSA-TRE) (U.S. Pat. No. 5,648,478), the glandular kallikrein-1 gene (from the human gene, hKLK2-TRE), and the probasin gene (PB-TRE) (International Patent Application No. PCT/US98/04132). All three of these genes are preferentially expressed in prostate cells and the expression is androgen-inducible. Generally, expression of genes responsive to androgen induction requires the presence of an androgen receptor (AR).

In some embodiments, the E3-containing adenovirus vectors of the invention comprise a PSA-TRE. PSA is synthesized exclusively by normal, hyperplastic, and malignant prostatic epithelia; hence, its tissue-specific expression has made it an excellent biomarker for benign prostatic hyperplasia (BPH) and prostatic carcinoma (CaP). Normal serum levels of PSA are typically below 5 ng/ml, with elevated levels indicative of BPH or CaP. Lundwall et al. (1987) *FEBS Lett.* 214: 317; Lundwall (1989) *Biochem. Biophys. Res. Comm.* 161: 1151; and Riegmann et al. (1991) *Molec. Endocrin.* 5: 1921.

The region of the PSA gene that is used to provide cell specificity dependent upon androgens, particular in prostate cells, involves approximately 6.0 kilobases. Schuur et al. (1996) *J. Biol. Chem.* 271:7043–7051. An enhancer region of approximately 1.5 kb in humans is located between nt −5322 and nt −3739, relative to the transcription start site of the PSA gene. The PSA promoter consists of the sequence from about nt −540 to nt +8 relative to the transcription start site. Juxtapositioning of these two genetic elements yield a fully functional, minimal prostate-specific enhancer/promoter (PSA-TRE). Other portions of the approximately 6.0 kb region of the PSA gene can be used in the present invention, as long as requisite functionality is maintained. Accordingly, in some embodiments, a PSA-TRE comprises nucleotides −5322 to −3739 juxtaposed to nucleotides −540 to +8 relative to the transcription start site of the PSA gene.

In Example 1, adenoviral vector CN797 is described which comprises a composite TRE comprising an HRE and a PSA-TRE, the PSA-TRE comprising a PSA enhancer from −5322 to −3738 fused to a PSA promoter from −541 to +12. This PSA-TRE is derived from adenoviral vector CN706. Rodriguez et al. (1997) *Cancer Research* 57:2559–2563. Accordingly, in one embodiment an adenoviral vector comprises and adenovirus E1A gene under transcriptional control of a composite TRE comprising the cell status-specific TRE, HRE, and a cell type-specific TRE, a PSA-TRE.

The PSE and PSA TRE used in the present invention are derived from sequences depicted in and FIG. 22 (SEQ ID NO:9).

In some embodiments, the E3-containing adenovirus vectors of the invention comprise a probasin TRE. The rat probasin (PB) gene encodes a nuclear and secreted protein, probasin, that is only expressed in the dorsolateral prostate. Dodd et al. (1983) *J. Biol. Chem.* 258:10731–10737; Matusik et al. (1986) *Biochem. Cell. Biol.* 64: 601–607; and Sweetland et al. (1988) *Mol. Cell. Biochem.* 84: 3–15.

The PB-TREs used in this invention are derived from mammalian cells, including but not limited to, rodent cells, such as rat. In the Examples provided herein, a PB-TRE is derived from rat cells. In one embodiment, the PB-TRE comprises a promoter of a probasin gene. In one embodiment, the PB-TRE comprises an enhancer from a probasin gene. In another embodiment, the PB-TRE comprises a promoter from a probasin gene and an enhancer from a probasin gene. In certain embodiments wherein the PB-TRE comprises an enhancer from a probasin gene, the enhancer may be in combination with a promoter from a probasin gene or a promoter from another gene. In certain embodiments wherein the PB-TRE comprises a promoter from a probasin gene, the promoter may be in combination with an enhancer from a probasin gene or an enhancer from another gene. In addition, the PB-TRE can comprise multiple promoters and/or multiple enhancers derived from the probasin gene or another gene or other genes.

A DNA fragment comprising the 5'-flanking PB DNA, nt about −426 to about +28 (SEQ ID NO:13), carries sufficient information to direct prostate-specific, developmentally- and hormonally-regulated expression of a heterologous (non-probasin) gene in transgenic mice. Greenberg et al. (1994) *Mol. Endocrinol.* 8: 230–239; Foster et al. (1997) *Cancer Res.* 57:3325–30. Furthermore, this expression was both male-specific and restricted to the epithelial cells of the lateral, dorsal, and ventral prostate lobes. The demonstration that the foreign gene activity approached precastration levels when transgenic mice were supplemented with testosterone indicates that the PB-driven reporter transgene was responding to androgens in vivo. Moreover, a PB-TRE could drive expression of the simian virus 40 large tumor antigen-coding region in the prostate of the transgenic mice. Greenberg et al. (1995) *Proc. Natl. Acad. Sci.* 92: 3439–3443.

Accordingly, in one embodiment, a PB-TRE is the sequence upstream of the probasin coding segment, comprising, for example, the sequence given in SEQ ID NO:13. This sequence, e.g. from about −426 to about +28 relative to the transcriptional start site, comprises protein binding sites believed to be important or essential in cell-specific transcription, including ARE-1, ARE-2, a CAAT box, and a TATAA box.

Alternatively, a PB-TRE comprises, for example, the fragment of DNA upstream of the PB gene between base pairs about −286 and about +28 relative to the transcriptional start (nucleotides about 141 to about 454 of SEQ ID NO:13). Rennie et al. (1993) *Mol. Endocrinol.* 7:23–36. Sequence analysis revealed that this PB-TRE contains two ARE sites (designated ARE-1, also known as ARBS-1, which resembles a glucocorticoid response element, at about −236 to about −223 relative to the transcriptional start (nucleotides about 191 to about 204 of SEQ ID NO:13); and ARE-2, also known as ARBS-2, which is a unique sequence at about −140 to about −117 (nucleotides about 286 to about 310 of SEQ ID NO:13) required for androgen regulation. A single base mutation in ARE-1 or ARE-2 can result in the loss of androgen induction. Rennie et al. (1993) *Mol. Endocrinol.* 7:23–36. A fragment of 5'-flanking PB DNA containing the two ARE sites could drive expression of the bacterial chloramphenicol actyltransferase (CAT); expression was prostate-specific and inducible by androgens, but not by glucocorticoids. Greenberg et al. (1994) *Mol. Endocrinol.* 8:230–239. Like the probasin gene, the AR gene itself is regulated by two ARE sites upstream of the coding segment. The first AR gene ARE site, ARE-1, resembles a half-site of the palindromic hormone response element and the second, ARE-2, is identical to a portion of the probasin sequence. Dai et al. (1996) *Mol. Endocrinol* 10:1582–94. A PB enhancer is exemplified by an ARE site or pair of ARE sites, or any other sequence capable of assisting a promoter in prostate-specific transcription. Proper spacing between ARE sites may also be important in their function.

In some embodiments, the E3-containing adenovirus vectors of the invention comprise a human glandular kallikrein-2 TRE (hKLK2-TRE). The hKLK2 gene encodes human glandular kallikrein-2 (hK2), a protein which is synthesized virtually exclusively in prostate cells and whose synthesis is upregulated by androgens, primarily by transcriptional activation of hKLK2. Wolf et al. (1992) *Molec. Endocrinol.* 6:753–762; Morris (1989) *Clin. Exp. Pharm. Physiol.* 16:345–351; Qui et al. (1990) *J. Urol.* 144:1550–1556; Young et al. (1992) *Biochem.* 31:818–824.

hKLK2 promoter activity has been described. Schedlich et al. (1987) *DNA* 6:429–437; and Murtha et al. (1993) *Biochem.* 32:6459–6464. Promoter activity has been attributed to nucleotides about 11,290 to about 12,047 of SEQ ID NO:11. Accordingly, in some embodiments, an hKLK2 TRE comprises an hKLK2 promoter comprising nucleotides about 11,290 to about 12,047 of SEQ ID NO:11.

hKLK2 enhancer activity is found within nucleotides 1 through 9765 of SEQ ID NO:11 (corresponding to −12,014 to −2257 relative to the transcription start site). Portions of this region have been identified which retain enhancer function. Enhancer activity has been demonstrated in the region from nucleotides 8021 to 8371 of SEQ ID NO:11 (corresponding to −3993 to −3643 relative to the transcription start site), as described in PCT/US98/16312. Accordingly, the invention includes an isolated polynucleotide sequence comprising nucleotides about 8021 to about 8371 of SEQ ID NO:11. Enhancer activity has also been demonstrated in the region from nucleotides 7200 to 8371 of SEQ ID NO:11 (corresponding to −4814 to −3643 relative to the transcription start site), as described. Accordingly, the invention includes an isolated polynucleotide sequence comprising about 7200 to about 8371 of SEQ ID NO:11. Enhancer activity has further been demonstrated in the region from 6859 to 8627 of SEQ ID NO:11 (−5155 to −3387 relative to the transcription start site). Accordingly, the invention includes an isolated polynucleotide sequence comprising about 6859 to about 8627 of SEQ ID NO:11. Enhancer activity has been demonstrated in the region from 5976 to 9620 of SEQ ID NO:11 (−6038 to −2394 relative to the transcription start site). Accordingly, the invention includes an isolated polynucleotide sequence comprising about 5976 to about 9620 of SEQ ID NO:11. An active enhancer lies within an XhoI-ApaI fragment spanning a region from about 2 to about 6 kb upstream of the hKLK2 structural gene. Accordingly, the invention further includes an isolated polynucleotide comprising nucleotides about 1 through about 9765 of SEQ ID NO:11. For each of these embodiments, the polynucleotide has enhancer activity.

In the present invention, cell type-specific TREs may be preferentially functional in particular tumor cells. Non-limiting examples of tumor cell-specific TREs, and non-limiting examples of respective potential target cells, include TREs from the following genes: α-fetoprotein (AFP) (liver cancer), mucin-like glycoprotein DF3 (MUC1) (breast carcinoma), carcinoembryonic antigen (CEA) (colorectal, gastric, pancreatic, breast, and lung cancers), plasminogen activator urokinase (uPA) and its receptor gene (breast, colon, and liver cancers), HER-2/neu (c-erbB2/neu) (breast, ovarian, stomach, and lung cancers).

Other cell type-specific TREs may be derived from the following exemplary genes (cell type in which the TREs are specifically functional are in parentheses): vascular endothelial growth factor receptor (endothelium), albumin (liver), factor VII (liver), fatty acid synthase (liver), von Willebrand factor (brain endothelium), alpha-actin and myosin heavy chain (both in smooth muscle), synthetase I (small intestine), Na—K—Cl transporter (kidney). Additional cell type-specific TREs are known in the art, and some exemplary TREs are discussed below.

In some embodiments, the E3-containing adenovirus vectors of the invention comprise an AFP-TRE. AFP is an oncofetal protein, the expression of which is primarily restricted to developing tissues of endodermal origin (yolk sac, fetal liver, and gut), although the level of its expression varies greatly depending on the tissue and the developmental stage. AFP is of clinical interest because the serum concentration of AFP is elevated in a majority of hepatoma patients, with high levels of AFP found in patients with advanced disease. The serum AFP levels in patients appear to be regulated by AFP expression in hepatocellular carcinoma but not in surrounding normal liver. Thus, the AFP gene appears to be regulated to hepatoma cell-specific expression.

Cell type-specific TREs from the AFP gene have been identified. For example, the cloning and characterization of human AFP-specific enhancer activity is described in Watanabe et al. (1987) *J. Biol. Chem.* 262:4812–4818. The entire 5' AFP flanking region (containing the promoter, putative silencer, and enhancer elements) is contained within approximately 5 kb upstream from the transcription start site.

The AFP enhancer region in human is located between about nt −3954 and about nt −3335, relative to the transcription start site of the AFP gene. The human AFP promoter encompasses a region from about nt −174 to about nt +29. Juxtapositioning of these two genetic elements yields a fully functional AFP-TRE. This AFP-TRE is depicted in FIG. 27. Ido et al. (1995) describe a 259 bp promoter fragment (nt −230 to nt +29) that is specific for HCC. *Cancer Res.* 55:3105–3109. The AFP enhancer contains two regions, denoted A and B, located between nt −3954 and nt −3335 relative to the transcription start site. The promoter region contains typical TATA and CAAT boxes. Accordingly, in some embodiments, an AFP-TRE comprises nucleotides −3954 to −3335 relative to the AFP gene transcription start site and a promoter. In other embodiments, an AFP-TRE comprises nucleotides −174 to +29 relative to the AFP gene transcription start site. In other embodiments, an AFP-TRE comprises nucleotides −3954 to −3335 juxtaposed to −174 to +29 relative to the AFP gene transcription start site.

Suitable target cells for adenoviral vectors containing AFP-TREs are any cell type that allow an AFP-TRE to function. Preferred are cells that express, or produce, AFP, including, but not limited to, tumor cells expressing AFP. Examples of such cells are hepatocellular carcinoma cells, gonadal and other germ cell tumors (especially endodermal sinus tumors), brain tumor cells, ovarian tumor cells, acinar cell carcinoma of the pancreas (Kawamoto et al. (1992) *Hepatogastroenterology* 39:282–286), primary gall bladder tumor (Katsuragi et al. (1989) *Rinsko Hoshasen* 34:371–374), uterine endometrial adenocarcinoma cells (Koyama et al. (1996) *Jpn. J. Cancer Res.* 87:612–617), and any metastases of the foregoing (which can occur in lung, adrenal gland, bone marrow, and/or spleen). In some cases, metastatic disease to the liver from certain pancreatic and stomach cancers produce AFP. Especially preferred are hepatocellular carcinoma cells and any of their metastases. AFP production can be measured using assays standard in the art, such as RIA, ELISA or Western blots (immunoassays) to determine levels of AFP protein production or Northern blots to determine levels of AFP mRNA production. Alternatively, such cells can be identified and/or characterized by their ability to activate transcriptionally an AFP-TRE (i.e., allow an AFP-TRE to function).

In some embodiments, the E3-containing adenovirus vectors of the invention comprise a urokinase plasminogen activator TRE. The protein urokinase plasminogen activator (uPA) and its cell surface receptor, urokinase plasminogen activator receptor (uPAR), are expressed in many of the most frequently occurring neoplasia and appear to represent important proteins in cancer metastasis. Both proteins are implicated in breast, colon, prostate, liver, renal, lung and ovarian cancer. Transcriptional regulatory elements that regulate uPA and uPAR transcription have been extensively studied. Riccio et al. (1985) *Nucleic Acids Res.* 13:2759–2771; Cannio et al. (1991) *Nucleic Acids Res.* 19:2303–2308.

In some embodiments, the E3-containing adenovirus vectors of the invention comprise a carcinoembryonic antigen TRE. CEA is a 180,000-Dalton glycoprotein tumor-associated antigen present on endodermally-derived neoplasia of the gastrointestinal tract, such as colorectal, gastric (stomach) and pancreatic cancer, as well as other adenocarcinomas such as breast and lung cancers. CEA is of clinical interest because circulating CEA can be detected in the great majority of patients with CEA-positive tumors. In lung cancer, about 50% of total cases have circulating CEA, with high concentrations of CEA (greater than 20 ng/ml) often detected in adenocarcinomas. Approximately 50% of patients with gastric carcinoma are serologically positive for CEA.

The 5' upstream flanking sequence of the CEA gene has been shown to confer cell-specific activity. The CEA promoter region, approximately the first 424 nucleotides upstream of the translational start site in the 5' flanking region of the gene, was shown to confer cell-specific activity when the region provided higher promoter activity in CEA-producing cells than in non-producing HeLa cells. Schrewe et al. (1990) *Mol. Cell. Biol.* 10:2738–2748. In addition, cell-specific enhancer regions have been found. WO 95/14100. The entire 5' CEA flanking region (containing the promoter, putative silencer, and enhancer elements) appears to be contained within approximately 14.5 kb upstream from the translation start site. Richards et al. (1995); WO 95/14100. Further characterization of the 5' flanking region of the CEA gene by Richards et al. (1995) indicated two upstream regions, −13.6 to −10.7 kb or −6.1 to −4.0 kb, when linked to the multimerized promoter resulted in high-level and selective expression of a reporter construct in CEA-producing LoVo and SW1463 cells. Richards et al. (1995) also localized the promoter region to nt −90 and nt +69 relative to the translational start site, with region nt −41 to nt −18 as essential for expression. WO95/14100 describes a series of 5' flanking CEA fragments which confer cell-specific activity, such as about nt −299 to about nt +69; about nt −90 to about nt +69; nt −14,500 to nt −10,600; nt −13,600 to nt −10,600, nt −6100 to nt −3800. In addition, cell specific transcription activity is conferred on an operably linked gene by the CEA fragment from nt −402 to nt +69, depicted in (SEQ ID NO:10). In the above-described CEA-TREs, numbering is relative to the translation start site.

Figure 16:
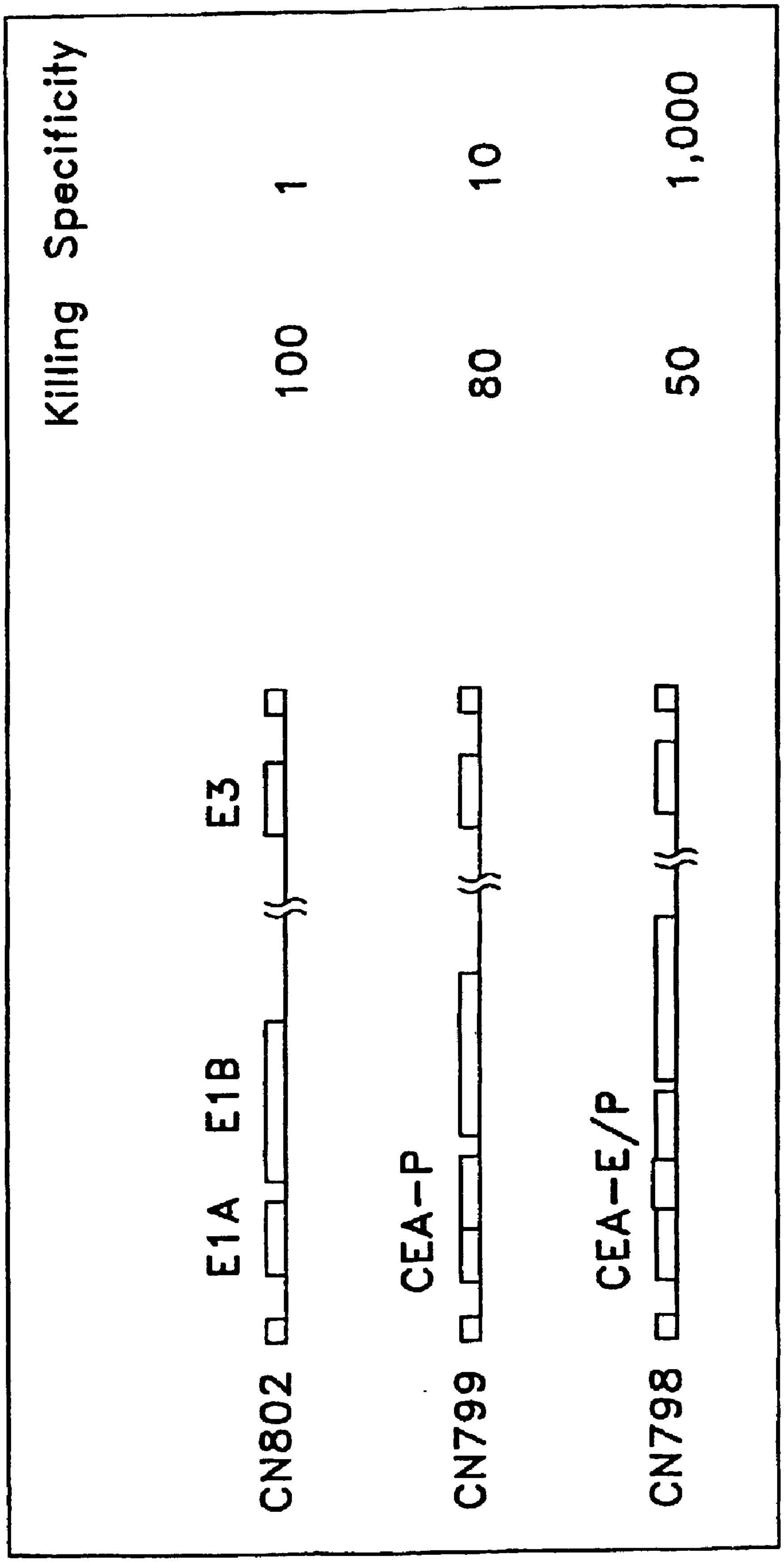
FIG. 16 is a schematic representation of adenoviral constructs CN802, CN799, and CN798, all of which contain E3. Specificity and extent of killing are also indicated for each virus.

As shown in Example 4, cell type-specific transcription activity is also conferred on an operably linked gene by a CEA promoter fragment from nucleotide (nt) −300 to +70 relative to the CEA gene transcription start site (nucleotides 14161 to 14532 of the sequence depicted in FIG. 23 (SEQ ID NO:10)). Accordingly, in some embodiments, an E3-containing adenoviral vector of the invention comprises a CEA-TRE comprising a nucleotide sequence from about 14161 to about 14532 of SEQ ID NO:10), i.e., CN799, shown in FIG. 16. This promoter fragment can be used alone or in combination with one or more enhancer fragments derived from a CEA gene 5' flanking region. Thus, as shown in Example 4, cell type-specific transcription activity is also conferred on an operably linked gene by a CEA-TRE comprising a promoter fragment from −300 to +70 relative to the CEA gene transcription start site juxtaposed to a CEA enhancer fragment comprising nucleotides −6072 to −3815 relative to the CEA transcription start site (nucleotides 8392 to 10548 of the sequence depicted in FIG. 23 (SEQ ID NO:10). Accordingly, in some embodiments, an E3-containing adenoviral vector of the invention comprises a CEA-TRE comprising a nucleotide sequence from about 14161 to about 14532 of SEQ ID NO:10) operably linked to a nucleotide sequence from about 8392 to about 10548 of SEQ ID NO:10), i.e., CN798, shown in FIG. 16. In other embodiments, a CEA-TRE comprises a CEA promoter fragment from about −300 to about +70 relative to the CEA transcription start site operably linked to a CEA enhancer fragment from about −6072 to about −3815 and about −13.6 kb to about −10.7 kb relative to the CEA gene transcription start site. Any of the CEA-TREs used in the present invention are derived from mammalian cells, including but not limited to, human cells. Thus, any of the CEA-TREs may be used in the invention as long as requisite desired functionality is displayed in the adenovirus vector. The cloning and characterization of CEA sequences have been described in the literature and are thus made available for practice of this invention and need not be described in detail herein.

In some embodiments, the E3-containing adenovirus vectors of the invention comprise a mucin TRE. The protein product of the MUC1 gene (known as mucin or MUC1 protein; episialin; polymorphic epithelial mucin or PEM; EMA; DF3 antigen; NPGP; PAS-O; or CA15.3 antigen) is normally expressed mainly at the apical surface of epithelial cells lining the glands or ducts of the stomach, pancreas, lungs, trachea, kidney, uterus, salivary glands, and mammary glands. Zotter et al. (1988) *Cancer Rev.* 11–12: 55–101; and Girling et al. (1989) *Int. J. Cancer* 43: 1072–1076. However, mucin is overexpressed in 75–90% of human breast carcinomas. Kufe et al. (1984) *Hybridoma* 3: 223–232. For reviews, see Hilkens (1988) *Cancer Rev.* 11–12: 25–54; and Taylor-Papadimitriou, et al. (1990) *J. Nucl. Med. Allied Sci.* 34: 144–150. Mucin protein expression correlates with the degree of breast tumor differentiation. Lundy et al. (1985) *Breast Cancer Res. Treat.* 5: 269–276. This overexpression appears to be controlled at the transcriptional level.

Overexpression of the MUC1 gene in human breast carcinoma cells MCF-7 and ZR-75-1 appears to be regulated at the transcriptional level. Kufe et al. (1984); Kovarik (1993) *J. Biol. Chem.* 268:9917–9926; and Abe et al. (1990) *J. Cell. Physiol.* 143: 226–231. The regulatory sequences of the MUC1 gene have been cloned, including the approximately 0.9 kb upstream of the transcription start site which contains a TRE that appears to be involved in cell-specific transcription. Abe et al. (1993) *Proc. Natl. Acad. Sci. USA* 90: 282–286; Kovarik et al. (1993); and Kovarik et al. (1996) *J. Biol. Chem.* 271:18140–18147.

Any MUC1-TREs used in the present invention are derived from mammalian cells, including but not limited to, human cells. Preferably, the MUC1-TRE is human. In one embodiment, the MUC1-TRE may contain the entire 0.9 kb 5' flanking sequence of the MUC1 gene. In other embodiments, the MUC1-TREs comprise the following sequences (relative to the transcription start site of the MUC1 gene): about nt −725 to about nt +31, nt −743 to about nt +33, nt −750 to about nt +33, and nt −598 to about nt +485 (operably-linked to a promoter).

In some embodiments, the E3-containing adenovirus vectors of the invention comprise a c-erbB2/neu TRE. The c-erbB2/neu gene (HER-2/neu or HER) is a transforming gene that encodes a 185 kD epidermal growth factor receptor-related transmembrane glycoprotein. In humans, the c-erbB2/neu protein is expressed during fetal development, however, in adults, the protein is weakly detectable (by immunohistochemistry) in the epithelium of many normal tissues. Amplification and/or over-expression of the c-erbB2/neu gene has been associated with many human cancers, including breast, ovarian, uterine, prostate, stomach and lung cancers. The clinical consequences of the c-erbB2/neu protein over-expression have been best studied in breast and ovarian cancer. c-erbB2/neu protein over-expression occurs in 20 to 40% of intraductal carcinomas of the breast and 30% of ovarian cancers, and is associated with a poor prognosis in subcategories of both diseases. Human, rat and mouse c-erbB2/neu TREs have been identified and shown to confer c-erbB2/neu expressing cell specific activity. Tal et al. (1987) *Mol. Cell. Biol.* 7:2597–2601; Hudson et al. (1990) *J. Biol. Chem.* 265:4389–4393; Grooteclaes et al. (1994) *Cancer Res.* 54:4193–4199; Ishii et al. (1987) *Proc. Natl. Acad. Sci. USA* 84:4374–4378; Scottetal. (1994) *J. Biol. Chem.* 269:19848–19858.

The cell type-specific TREs listed above are provided as non-limiting examples of TREs that would function in the instant invention. Additional cell type-specific TREs are known in the art, as are methods to identify and test cell specificity of suspected cell type-specific TREs.

Cell Status-specific TREs

Cell status-specific TREs for use in the E3-containing adenoviral vectors of the present invention can be derived from any species, preferably a mammal. A number of genes have been described which are expressed in response to, or in association with, a cell status. Any of these cell status-associated genes may be used to generate a cell status-specific TRE.

An example of a cell status is cell cycle. An exemplary gene whose expression is associated with cell cycle is E2F-1, a ubiquitously expressed, growth-regulated gene, which exhibits peak transcriptional activity in S phase. Johnson et al. (1994) *Genes Dev.* 8:1514–1525. The RB protein, as well as other members of the RB family, form specific complexes with E2F-1, thereby inhibiting its ability to activate transcription. Thus, E2F-1-responsive promoters are down-regulated by RB. Many tumor cells have disrupted RB function, which can lead to de-repression of E2F-1-responsive promoters, and, in turn, de-regulated cell division.

Accordingly, in one embodiment, the invention provides an E3-containing adenoviral vector in which an adenoviral gene (preferably a gene necessary for replication) is under transcriptional control of a cell status-specific TRE, wherein the cell status-specific TRE comprises a cell cycle-activated TRE. In one embodiment, the cell cycle-activated TRE is an E2F1 TRE. In one embodiment, this TRE comprises the sequence depicted in FIG. 21 (SEQ ID NO:8).

Another group of genes that are regulated by cell status are those whose expression is increased in response to hypoxic conditions. Bunn and Poyton (1996) *Physiol. Rev.* 76:839–885; Dachs and Stratford (1996) *Br. J. Cancer* 74:5126–5132; Guillemin and Krasnow (1997) *Cell* 89:9–12. Many tumors have insufficient blood supply, due in part to the fact that tumor cells typically grow faster than the endothelial cells that make up the blood vessels, resulting in areas of hypoxia in the tumor. Folkman (1989) *J. Natl. Cancer Inst.* 82:4–6; and Kallinowski (1996) *The Cancer J.* 9:37–40. An important mediator of hypoxic responses is the transcriptional complex HIF-1, or hypoxia inducible factor-1, which interacts with a hypoxia-responsive element (HRE) in the regulatory regions of several genes, including vascular endothelial growth factor, and several genes encoding glycolytic enzymes, including enolase-1. Murine HRE sequences have been identified and characterized. Firth et al. (1994) *Proc. Natl. Acad. Sci. USA* 91:6496–6500. An HRE from a rat enolase-1 promoter is described in Jiang et al. (1997) *Cancer Res.* 57:5328–5335. An HRE from a rat enolase-1 promoter is depicted in FIG. 20 (SEQ ID NO:7).

Accordingly, in one embodiment, an E3-containing adenovirus vector comprises an adenovirus gene, preferably an adenoviral gene essential for replication, under transcriptional control of a cell status-specific TRE comprising an HRE. In one embodiment, the cell status-specific TRE comprises the HRE depicted in FIG. 20 (SEQ ID NO:7).

Other cell status-specific TREs include heat-inducible (i.e., heat shock) promoters, and promoters responsive to radiation exposure, including ionizing radiation and UV radiation. For example, the promoter region of the early growth response-1 (Egr-1) gene contains an element(s) inducible by ionizing radiation. Hallahan et al. (1995) *Nat. Med.* 1:786–791; and Tsai-Morris et al. (1988) *Nucl. Acids. Res.* 16:8835–8846. Heat-inducible promoters, including heat-inducible elements, have been described. See, for example Welsh (1990) in "Stress Proteins in Biology and Medicine", Morimoto, Tisseres, and Georgopoulos, eds. Cold Spring Harbor Laboratory Press; and Perisic et al. (1989) *Cell* 59:797–806. Accordingly, in some embodiments, the cell status-specific TRE comprises an element(s) responsive to ionizing radiation. In one embodiment, this TRE comprises a 5' flanking sequence of an Egr-1 gene. In other embodiments, the cell status-specific TRE comprises a heat shock responsive element.

The cell status-specific TREs listed above are provided as non-limiting examples of TREs that would function in the instant invention. Additional cell status-specific TREs are known in the art, as are methods to identify and test cell status specificity of suspected cell status-specific TREs.

Adenovirus Genes Under Control of a Target Cell-specific TRE

In the E3-containing adenoviral vectors of the present invention, an adenovirus gene, preferably an adenovirus gene essential for replication, is under control of a target cell-specific TRE.

Preferably, the gene(s) is an early gene, such as E1A, E1B, E2, and/or E4. Embodiments in which E3 is under transcriptional control of a target cell-specific TRE have been discussed above. More preferably, the early gene(s) under target cell-specific TRE control is E1A and/or E1B. More than one early gene can be placed under control of an target cell-specific TRE. Example 1 provides a more detailed description of such constructs.

The E1A gene is expressed immediately after viral infection (0–2 hours) and before any other viral genes. E1A protein acts as a trans-acting positive-acting transcriptional regulatory factor, and is required for the expression of the other early viral genes E1B, E2, E3, E4, and the promoter-proximal major late genes. Despite the nomenclature, the promoter proximal genes driven by the major late promoter are expressed during early times after Ad5 infection. Flint (1982) *Biochem. Biophys. Acta* 651:175–208; Flint (1986) *Advances Virus Research* 31:169–228; Grand (1987) *Biochem. J.* 241:25–38. In the absence of a functional E1A gene, viral infection does not proceed, because the gene products necessary for viral DNA replication are not produced. Nevins (1989) *Adv. Virus Res.* 31:35–81. The transcription start site of Ad5 E1A is at nucleotide 498 and the ATG start site of the E1A protein is at nucleotide 560 in the virus genome.

The E1B protein functions in trans and is necessary for transport of late mRNA from the nucleus to the cytoplasm. Defects in E1B expression result in poor expression of late viral proteins and an inability to shut off host cell protein synthesis. The promoter of E1B has been implicated as the defining element of difference in the host range of Ad40 and Ad5: clinically Ad40 is an enterovirus, whereas Ad5 causes acute conjunctivitis. Bailey, Mackay et al. (1993) *Virology* 193:631; Bailey et al. (1994) *Virology* 202:695–706). The E1B promoter of Ad5 consists of a single high-affinity recognition site for Spl and a TATA box.

The E2 region of adenovirus codes for proteins related to replication of the adenoviral genome, including the 72 kDa DNA-binding protein, the 80 kD precursor terminal protein and the viral DNA polymerase. The E2 region of Ad5 is transcribed in a rightward orientation from two promoters, termed E2 early and E2 late, mapping at 76.0 and 72.0 map units, respectively. While the E2 late promoter is transiently active during late stages of infection and is independent of the E1A transactivator protein, the E2 early promoter is crucial during the early phases of viral replication.

The E2 late promoter overlaps with the coding sequences of a gene encoded by the counterstrand and is therefore not amenable to genetic manipulation. However, the E2 early promoter overlaps only for a few base pairs with sequences coding for a 33 kD protein on the counterstrand. Notably, the SpeI restriction site (Ad5 position nt 27082) is part of the stop codon for the above mentioned 33 kD protein and conveniently separates the major E2 early transcription initiation site and TATA-binding protein site from the upstream transcription factor biding sites E2F and ATF. Therefore, insertion of a target cell-specific TRE having SpeI ends into the SpeI site in the +-strand would disrupt the endogenous E2 early promoter of Ad5 and should allow target cell-restricted expression of E2 transcripts.

The E4 gene has a number of transcription products. The E4 region codes for two polypeptides which are responsible for stimulating the replication of viral genomic DNA and for stimulating late gene expression. The protein products of open reading frames (ORFS) 3 and 6 can both perform these functions by binding the 55 kD protein from E1B and heterodimers of E2F-1 and DP-1. The ORF 6 protein requires interaction with the E1B 55 kD protein for activity while the ORF 3 protein does not. In the absence of functional protein from ORF 3 and ORF 6, plaques are produced with an efficiency less than $10^{-6}$ that of wild type virus. To further restrict viral replication to cells exhibiting a requisite physiological condition or state, E4 ORFs 1–3 can be deleted, making viral DNA replication and late gene synthesis dependent on E4 ORF 6 protein. By combining such a mutant with sequences in which the E1B region is regulated by a target cell-specific TRE, a virus can be obtained in which both the E1B function and E4 function are dependent on a target cell-specific TRE driving E1B.

The major late genes relevant to the subject invention are genes L1, L2, L3, L4, and L5 which encode proteins of the adenovirus virion. All of these genes (typically coding for structural proteins) are probably required for adenoviral replication. The late genes are all under the control of the major late promoter (MLP), which is located in Ad5 at nucleotides +5986 to +6048.

Transgenes

In addition to conferring selective cytotoxic and/or cytolytic activity by virtue of preferential replication competence in target cells, the adenovirus vectors of this invention can further include a heterologous gene (transgene) under the control of a heterologous TRE. In this way, various genetic capabilities may be introduced into target cells, particularly cancer cells. For example, in certain instances, it may be desirable to enhance the degree and/or rate of cytotoxic activity, due to, for example, the relatively refractory nature or particular aggressiveness of the cancerous target cell. This could be accomplished by coupling the target cell-specific cytotoxic activity with cell-specific expression of, for example, HSV-tk and/or cytosine deaminase (cd), which renders cells capable of metabolizing 5-fluorocytosine (5-FC) to the chemotherapeutic agent 5-fluorouracil (5-FU). Using these types of transgenes may also confer a bystander effect.

Other desirable transgenes that may be introduced via an adenovirus vector(s) include genes encoding cytotoxic proteins, such as the A chains of diphtheria toxin, ricin or abrin (Palmiter et al. (1987) *Cell* 50: 435; Maxwell et al. (1987) *Mol. Cell. Biol.* 7: 1576; Behringer et al. (1988) *Genes Dev.* 2: 453; Messing et al. (1992) *Neuron* 8: 507; Piatak et al. (1988) *J. Biol. Chem.* 263: 4937; Lamb et al. (1985) *Eur. J. Biochem.* 148: 265; Frankel et al. (1989) *Mol. Cell. Biol.* 9: 415), genes encoding a factor capable of initiating apoptosis, sequences encoding antisense transcripts or ribozymes, which among other capabilities may be directed to mRNAs encoding proteins essential for proliferation, such as structural proteins, or transcription factors; viral or other pathogenic proteins, where the pathogen proliferates intracellularly; genes that encode an engineered cytoplasmic variant of a nuclease (e.g. RNase A) or protease (e.g. awsin, papain, proteinase K, carboxypeptidase, etc.), or encode the Fas gene, and the like. Other genes of interest include cytokines, antigens, transmembrane proteins, and the like, such as IL-1, -2, -6, -12, GM-CSF, G-CSF, M-CSF, IFN-α, -β, -γ, TNF-α, -β, TGF-α, -β, NGF, and the like. The positive effector genes could be used in an earlier phase, followed by cytotoxic activity due to replication.

Preparation of the Adenoviral Vectors of the Invention

The adenovirus vectors of this invention can be prepared using recombinant techniques that are standard in the art. Any of the various serotypes of adenovirus can be used in the present invention, such as Ad2, Ad5, Ad12 and Ad40. For purposes of illustration, serotype Ad5 is exemplified herein.

Polynucleotides used for making adenoviral vectors of this invention may be obtained using standard methods in the art, such as chemical synthesis, by recombinant methods, and/or by obtaining the desired sequence(s) from biological sources.

Adenoviral vectors are conveniently prepared by employing two plasmids, one plasmid providing for the left hand region of adenovirus and the other plasmid providing for the right hand region, where the two plasmids share at least about 500 nucleotides of middle region for homologous recombination. In this way, each plasmid, as desired, may be independently manipulated, followed by cotransfection in a competent host, providing complementing genes as appropriate. Plasmids are generally introduced into a suitable host cell such as 293 cells using appropriate means of transduction, such as lipid-containing agents (e.g., cationic liposomes). Alternatively, in vitro ligation of the right and left-hand portions of the adenovirus genome can also be used to construct recombinant adenovirus derivative containing all the replication-essential portions of adenovirus genome. Berkner et al. (1983) *Nucleic Acids Research* 11: 6003–6020; Bridge et al. (1989) *J. Virol.* 63: 631–638.

For convenience, plasmids are available that provide the necessary portions of adenovirus. Plasmid pXC.1

(McKinnon (1982) *Gene* 19:33–42) contains the wild-type left-hand end of Ad5. pBHGE3 (Microbix Biosystems Inc., Toronto) provides the right-hand end of Ad5, including E3.

For manipulation of the early genes, the transcription start site of Ad5 E1A is at nt 498 and the ATG start site of the E1A protein is at nt 560 in the virus genome. This region can be used for insertion of a target cell-specific TRE. A restriction site may be introduced by employing polymerase chain reaction (PCR), where the primer that is employed may be limited to the Ad5 genome, or may involve a portion of the plasmid carrying the Ad5 genomic DNA. For example, where pBR322 is used, the primers may use the EcoRI site in the pBR322 backbone and the XbaI site at nt 1339 of Ad5. By carrying out the PCR in two steps, where overlapping primers at the center of the region introduce a nucleotide sequence change resulting in a unique restriction site, one can provide for insertion of target cell-specific TRE at that site. Example 1 provides a more detailed description of an adenoviral vector in which E1A is under target cell-specific TRE control.

A similar strategy may also be used for insertion of a heterologous TRE to regulate E1B. The E1B promoter of Ad5 consists of a single high-affinity recognition site for Spl and a TATA box. This region extends from nt 1636 to nt 1701. By insertion of a heterologous TRE in this region, one can provide for target cell-specific transcription of the E1B gene. By employing the left-hand region modified with a heterologous TRE regulating E1A as the template for introducing a heterologous TRE to regulate E1B, the resulting adenovirus vector will be dependent upon the target cell-specific transcription factors for expression of both E1A and E1B.

Similarly, a heterologous TRE can be inserted upstream of the E2 gene to make its expression target cell specific. The E2 early promoter, mapping in Ad5 from nt 27050–27150, consists of a major and a minor transcription initiation site, the latter accounting for about 5% of the E2 transcripts, two non-canonical TATA boxes, two E2F transcription factor binding sites and an ATF transcription factor binding site. For a detailed review of the E2 promoter architecture see Swaminathan et al., *Curr. Topics in Microbiol. and Immunol.* (1995) 199 (part 3):177–194.

For E4, one must use the right hand portion of the adenovirus genome. The E4 transcription start site is predominantly at 35609, the TATA box at nt 35638 and the first ATG/CTG of ORF 1 is at nt 35532. Virtanen et al. (1984) *J. Virol.* 51: 822–831. Using any of the above strategies for the other genes, a heterologous TRE may be introduced upstream from the transcription start site. For the construction of mutants in the E4 region, the co-transfection and homologous recombination are performed in W162 cells (Weinberg et al. (1983) *Proc. Natl. Acad. Sci. USA* 80:5383–5386) which provide E4 proteins in trans to complement defects in synthesis of these proteins. Alternatively, these constructs can be produced by in vitro ligation.

Adenoviral constructs containing an E3 sequence can be generated as described in Example 1, wherein homologous recombination between an E3-containing adenoviral plasmid, for example, BHGE3 (Microbix Biosystems Inc., Toronto) and a non-E3-containing adenoviral plasmid, is carried out.

Alternatively, an adenoviral vector comprising an E3 sequence can be introduced into cells, for example 293 cells, along with an adenoviral construct or an adenoviral plasmid construct, where they can undergo homologous recombination to yield adenovirus containing an E3 region (or portion of E3). In this case, the E3-containing adenoviral vector and the adenoviral construct or plasmid construct contain complementary regions of adenovirus, for example, one contains the left-hand and the other contains the right-hand region, with sufficient sequence overlap as to allow homologous recombination.

Alternatively, an E3-containing adenoviral vector of the invention can be constructed using other conventional methods including standard recombinant methods (e.g., using restriction nucleases and/or PCR), chemical synthesis, or a combination of any of these. Further, deletions of portions of the E3 region can be created using standard techniques of molecular biology.

Host Cells Comprising the Adenoviral Vectors of the Invention

The present invention also provides host cells comprising (i.e., transformed with) the adenoviral vectors described herein. Both prokaryotic and eukaryotic host cells can be used as long as sequences requisite for maintenance in that host, such as appropriate replication origin(s), are present. For convenience, selectable markers are also provided. Prokaryotic host cells include bacterial cells, for example, *E. coli* and mycobacteria. Among eukaryotic host cells are yeast, insect, avian, plant and mammalian cells. Host systems are known in the art and need not be described in detail herein.

Compositions of the Invention

The present invention also provides compositions, including pharmaceutical compositions, containing an adenoviral vector(s) described herein. Such compositions (especially pharmaceutical compositions) are useful for administration in vivo, for example, when measuring the degree of transduction and/or effectiveness of cell killing in an individual. Pharmaceutical compositions, comprised an adenoviral vector of this invention in a pharmaceutically acceptable excipient (generally an effective amount of the adenoviral vector), are suitable for systemic or localized administration to individuals in unit dosage forms, sterile parenteral solutions or suspensions, sterile non-parenteral solutions or oral solutions or suspensions, oil in water or water in oil emulsions and the like. Formulations for parenteral and nonparenteral drug delivery are known in the art and are set forth in *Remington's Pharmaceutical Sciences,* 18th Edition, Mack Publishing (1990). Pharmaceutical compositions also include lyophilized and/or reconstituted forms of the adenoviral vectors (including those packaged as a virus, such as adenovirus) of the invention.

Other compositions are used, and are useful for, detection methods described herein. For these compositions, the adenoviral vector usually is suspended in an appropriate solvent or solution, such as a buffer system. Such solvent systems are well known in the art.

Kits of the Invention

The present invention also encompasses kits containing an adenoviral vector(s) of this invention. These kits can be used for diagnostic and/or monitoring purposes, preferably monitoring. Procedures using these kits can be performed by clinical laboratories, experimental laboratories, medical practitioners, or private individuals. Kits embodied by this invention allow detection of the presence of cells which allow a target cell-specific TRE to function, including, for example, neoplastic cells, in a suitable biological sample, such as biopsy specimens.

The kits of the invention comprise an adenoviral vector described herein in suitable packaging. The kit may optionally provide additional components that are useful in the procedure, including, but not limited to, buffers, developing reagents, labels, reacting surfaces, means for detection, control samples, instructions, and interpretive information.

Methods Using the Adenovirus Vectors of the Invention

The adenoviral vectors of the invention can be used for a wide variety of purposes, which will vary with the desired or intended result. Accordingly, the present invention includes methods using the adenoviral vectors described above.

In one embodiment, methods are provided for conferring selective cytotoxicity in target cells (i.e., cells which allow a target cell-specific TRE to function) comprising contacting the cells with an adenovirus vector described herein, such that the adenovirus vector enters the cell (and subsequently replicates). Cytotoxicity can be measured using standard assays in the art, such as dye exclusion, $^3$H-thymidine incorporation, and/or lysis.

In another embodiment, methods are provided for propagating an adenovirus specific for mammalian cells which allow a target cell-specific TRE to function. These methods entail combining an adenovirus vector with mammalian cells, whereby said adenovirus enters the cell and is propagated.

The invention further provides methods of suppressing tumor cell growth comprising contacting a tumor cell with an adenoviral vector of the invention such that the adenoviral vector enters the tumor cell and exhibits selective cytotoxicity for the tumor cell (and/or whereby introduction of the adenoviral vector results in suppression of tumor growth). Tumor cell growth can be assessed by any means known in the art, including, but not limited to, measuring tumor size, determining whether tumor cells are proliferating using a $^3$H-thymidine incorporation assay, or counting tumor cells.

The invention also includes methods for detecting target cells in a biological sample. These methods are particularly useful for monitoring the clinical and/or physiological condition of an individual (i.e., mammal), whether in an experimental or clinical setting. For these methods, cells of a biological sample are contacted with an adenovirus vector, and replication of the adenoviral vector is detected. A suitable biological sample is one in which target cells, for example, cancerous cells, may be or are suspected to be present. Generally, in mammals, a suitable clinical sample is one in which cancerous cells exhibiting a requisite physiological state, such as cells within a solid tumor which are under hypoxic conditions, or cancerous or non-cancerous cells of a particular cell type, are suspected to be present. Such cells can be obtained, for example, by needle biopsy or other surgical procedure. Cells to be contacted may be treated to promote assay conditions, such as selective enrichment, and/or solubilization. In these methods, target cells can be detected using in vitro assays that detect adenoviral proliferation, which are standard in the art. Examples of such standard assays include, but are not limited to, burst assays (which measure virus yield) and plaque assays (which measure infectious particles per cell). Propagation can also be detected by measuring specific adenoviral DNA replication, which are also standard assays.

The adenoviral vectors of the invention can be used alone or in conjunction with other active agents, such as chemotherapeutics, that promote the desired objective.

The adenoviral vectors can be used in a variety of forms, including, but not limited to, naked polynucleotide (usually DNA) constructs; polynucleotide constructs complexed with agents to facilitate entry into cells, such as cationic liposomes or other cationic compounds such as polylysine; packaged into infectious adenovirus particles (which may render the adenoviral vector(s) more immunogenic); packaged into other particulate viral forms such as HSV or AAV; complexed with agents (such as PEG) to enhance or dampen an immune response; complexed with agents that facilitate in vivo transfection, such as DOTMA™, DOTAP™, and polyamines.

If an adenoviral vector is packaged into an adenovirus, the adenovirus itself may also be selected to further enhance targeting. For example, adenovirus fibers mediate primary contact with cellular receptor(s) aiding in tropism. See, e.g., Amberg et al. (1997) *Virol.* 227:239–244. If a particular subgenus of an adenovirus serotype displayed tropism for a target cell type and/or reduced affinity for non-target cell types, such subgenus (or subgenera) could be used to further increase cell-specificity of cytotoxicity and/or cytolysis.

The adenoviral vectors may be delivered to the target cell in a variety of ways, including, but not limited to, liposomes, general transfection methods that are well known in the art (such as calcium phosphate precipitation or electroporation), direct injection, and intravenous infusion. The means of delivery will depend in large part on the particular adenoviral vector (including its form) as well as the type and location of the target cells (i.e., whether the cells are in vitro or in vivo).

If used as a packaged adenovirus, adenovirus vectors may be administered in an appropriate physiologically acceptable carrier at a dose of about $10^4$ to about $10^{14}$. The multiplicity of infection will generally be in the range of about 0.001 to 100. If administered as a polynucleotide construct (i.e., not packaged as a virus) about 0.01 $\mu$g to about 1000 $\mu$g of an adenoviral vector can be administered. The adenoviral vector(s) may be administered one or more times, whether systemically or locally, depending upon the intended use and the immune response potential of the host, and may also be administered as multiple, simultaneous injections. If an immune response is undesirable, the immune response may be diminished by employing a variety of immunosuppressants, so as to permit repetitive administration, without a strong immune response. If packaged as another viral form, such as HSV, an amount to be administered is based on standard knowledge about that particular virus (which is readily obtainable from, for example, published literature) and can be determined empirically.

The following examples are provided to illustrate but not limit the invention.

EXAMPLES

Example 1

Construction of Target Cell-specific Adenoviral Constructs Containing an E3 Region Target cell-specific adenoviral vectors were constructed by first generating target cell-specific adenoviral vectors and/or adenoviral plasmid vectors lacking an E3 region, then recombining these vectors with E3-containing adenoviral constructs.

With respect to adenoviral constructs (as opposed to precursor plasmid constructs), it is understood that "CN" and "CV" designations may be used interchangeably. For example, CN787 and CV787 refer to the same adenoviral construct.

Generation of Adenoviruses and Adenoviral Plasmid Vectors that Contain Target Cell-specific TREs Driving Expression of E1A and/or E1B A human embryonic kidney cell line, 293, efficiently expresses E1A and E1B genes of Ad5 and exhibits a high transfection efficiency with adenovirus DNA. For these experiments, 293 cells were co-transfected with one left end Ad5 plasmid and one right end Ad5 plasmid. Homologous recombination generates adenoviruses with the required genetic elements for replication in 293 cells which provide E1A and E1B proteins in trans to complement defects in synthesis of these proteins.

The plasmids to be combined were co-transfected into 293 cells using cationic liposomes such as Lipofectin (DOTMA:DOPE™, Life Technologies) by combining the two plasmids, then mixing the plasmid DNA solution (10 μg of each plasmid in 500 μl of minimum essential medium (MEM) without serum or other additives) with a four-fold molar excess of liposomes in 200 μl of the same buffer. The DNA-lipid complexes were then placed on the cells and incubated at 37° C., 5% $CO_2$ for 16 hours. After incubation the medium was changed to MEM with 10% fetal bovine serum and the cells are further incubated at 37° C., 5% $CO_2$, for 10 days with two changes of medium. At the end of this time the cells and medium were transferred to tubes, freeze-thawed three times, and the lysate was used to infect 293 cells at the proper dilution to detect individual viruses as plaques.

Plaques obtained were plaque purified twice, and viruses were characterized for presence of desired sequences by PCR and occasionally by DNA sequencing. For further experimentation, the viruses were purified on a large scale by cesium chloride gradient centrifugation.

CN739

An adenovirus vector in which expression of the E1A gene is under control of the PB-TRE and expression of the E1B gene is under control of the prostate specific antigen transcriptional regulatory element (PSA-TRE) was constructed as follows. The PSA-TRE region has been described in detail in, inter alia, U.S. Pat. Nos. 5,648,478 and 5,698,443; Lundwall (1989) *Biochim. Biophys Res. Commun.* 161:1151–1159; and Zhang et al. (1997) *Nucleic Acids Res.* 25:3143–50.

The PinAI PB-TRE fragment was inserted into CN125 digested with PinAI, which cleaves just upstream of E1A, to create construct CN257, which is a plasmid containing a PB-TRE (from −426 to +28 relative to the rat probasin gene transcription start site) operably linked to the E1A gene and a PSA-TRE (from −5322 to −3738 and −541 to +12 relative to the human PSA gene transcription start site) operably linked to the E1B gene.

Adenoviruses that contain two heterologous TREs were generated by homologous recombination in 293 cells. Briefly, 5 μg of CN257 and 5 μg of BHG10, which contains the right hand end of Ad5, was co-transfected into 293 cells. The cells were overlaid with medium, and infectious virus, generated by in vivo recombination, was detected by cytopathic effect and isolated. Plaque-purified stocks of an adenovirus vector, designated CN739, were established. The structure of the recombinant virus was characterized by PCR, restriction endonuclease digestion and Southern blot. The viral genome of CN739 has the E1A transcription unit of Ad5 under the control of PB-TRE while E1B is under the control of PSA-TRE.

CN732

CN732 (also referred to as CV732) which contains AFP-TRE driving expression of the E1A gene, was constructed by PCR as described below. CN732 contains the AFP enhancer domain (−3954 to −3335) and the promoter (−174 to +29) cloned into an engineered AgeI site at nt 547 of Ad5 to drive Ad5 E1a expression.

pXC.1 contains the left 16 mu of Ad5. pBHGE3 from Microbix, Inc., Toronto, Canada contains the circularized Ad5 genome with an E1 deletion extending to the packaging signal. Bett et al. (1994) *Proc. Natl. Acad. Sci. USA* 91:8802–8806; and McKinnon et al. (1982) *Gene* 19:33–42. A platform plasmid (CP124) with two unique restriction sites was constructed from pXC.1. CP124 has an AgeI site at bp 547 between the E1a mRNA cap site and E1a translation initiation site, and an EagI site at bp 1681 between the E1b promoter and E1b mRNA cap site. To construct viruses that preferentially replicate in $AFP^+$ cells, a composite AFP TRE of the enhancer and promoter was assembled by overlap PCR and cloned into CP124. The enhancer element (−3856 to −3267) was amplified from human genomic DNA (Clontech, Palo Alto, Calif.) with primers (SEQ ID NO:16)
5' GTGACCGGTG CATTGCTGTG AACTCTGTA 3' (39.055B);
and (SEQ ID NO:17)
5' ATAAGTGGCC TGGATAAAGC TGAGTGG 3' (38.055D).

The promoter (−163 to +34) was amplified with primers (SEQ ID NO:18)
5' GTCACCGGTC TTTGTTATTG GCAGTGGT 3' (39.055J);
and (SEQ ID NO:19)
5' ATCCAGGCCA CTTATGAGCT CTGTGTCCTT 3' (39.055M).

Underlined regions in primers 39.055B and 39.055J indicate AgeI sites. The two products were annealed and used as the template for PCR with primers 39.055B and 39.055J. This overlap product was digested with PinAI (an AgeI isoschizomer) and ligated to PinAI cut CP124.

The resulting plasmid, CN219, contains the AFP TRE driving the E1A gene. CN732 was generated via homologous recombination by cotransfecting 293 cells with CN219 with pBHG10. pBHG10 is a plasmid that contains all of the Ad5 sequences except the E1 region as well as a deletion in the E3 region from Ad5 bp 28133 to 30818.

CN733

CN733 (also referred to as CV733) which contains two AFP-TREs driving expression of the E1A and E1B genes, was constructed by using the following two PCR primers to amplify the enhancer/promoter element described above (−3954 to −3335 and −174 to +29):

(SEQ ID NO:1)
5' TATCGGCCGG CATTGCTGTG AACTCT 3' (39.077A): and (SEQ ID NO:2)
5' TTACGGCCGC TTTGTTATTG GCAGTG 3' (39.077C).

The PCR product was digested with EagI and ligated into similarly cut CN219. The resulting plasmid, CN224, contains two identical AFP regulatory elements, one each modulating expression of the E1A gene and the E1B gene. CN733 was generated by homologous recombination in 293 cells by cotransfecting CN224 and BHG10.

CN796

Adenoviral vector CN796 comprises a composite TRE comprising an HRE and a PSA-TRE, the PSA-TRE comprising a PSA enhancer from −5322 to −3738 fused to a PSA promoter from −541 to +12. This PSA-TRE is derived from adenoviral vector CN706. Rodriguez et al. (1997) *Cancer Research* 57:2559–2563.

CN796 was made by co-transfecting CN515 with pBHG10. CN515 was constructed by inserting a 67 base pair fragment from HRE enol (Jiang et al. (1997) *Cancer Research* 57:5328–5335) (SEQ ID NO:7; FIG. 20) into CN65 at the BglII site. CN65 is a plasmid containing an enhancer and promoter from the human PSA gene, consisting of an enhancer from −5322 to −3738 fused to a PSA promoter from −541 to +12. This is the PSA-TRE contained within plasmid CN706.

CN532

CEA-TRE-containing adenoviral vector CN532 was generated as follows. The native E1A promoter was deleted (as a 64 bp fragment) from CN124 (wild-type left-hand end of Ad5) to generate CN306. CN143 is a pBluescript (Stratagene, La Jolla, Calif.) derivative containing a PSA-TRE fragment. The PSA-TRE fragment from CN143 was then inserted upstream of the promoter-less E1A coding segment of CN306 to generate CN321.

CN532 was constructed from CN321 by replacing the PSA-TRE of CN321 with a CEA promoter. The CEA promoter was amplified from human genomic DNA by PCR using two primers:

```
                                       (SEQ ID NO:3)
5' GATCTCGAGA CCCGGGACCC TGCTGGGTTT C 3'
(76.13.1); and

                                       (SEQ ID NO:4)
5' GATCACCGGT GCTTGAGTTC CAGGAACGTT TTG 3'
(76.13.2).
```

The PCR product was enzymatically digested with PinAI, then ligated to PinAI-cut CN321 vector portion. The CEA promoter fragment amplified by these primers corresponds to −300 to +70 relative to the CEA gene transcription start site.

CN525

As with CN532, CN525 was generated from CN321 by replacing the PSA-TRE with a CEA promoter and enhancer. The CEA enhancer was amplified from human genomic DNA by PCR using two synthetic oligonucleotide primers:

```
                                       (SEQ ID NO:5)
5' GATCAACCGG TACCGACTTC TGTAGCTTTG GGAAGG 3'
(76.13.3); and

                                       (SEQ ID NO:6)
5' GATCCTCGAG CCCGGGTTCA AGCAATTCTC CTGC 3'
(76.13.4).
```

The PCR product was cut with PinAI, ligated to the CEA promoter fragment described above, and ligated to PinAI-cut CN321. The orientation of the enhancer fragment is 3' to 5' relative to the promoter. The CEA enhancer fragment amplified by 76.13.3 and 76.13.4 corresponds to −6072 to −3815 relative to the CEA gene transcription start site. Thus, CN525 contains a CEA-TRE comprising a CEA enhancer from −6072 to −3815 juxtaposed to a CEA promoter from −300 to +70 relative to the CEA gene transcription start site.

Generation of Recombinant Adenoviruses Containing E3

Figure 2:
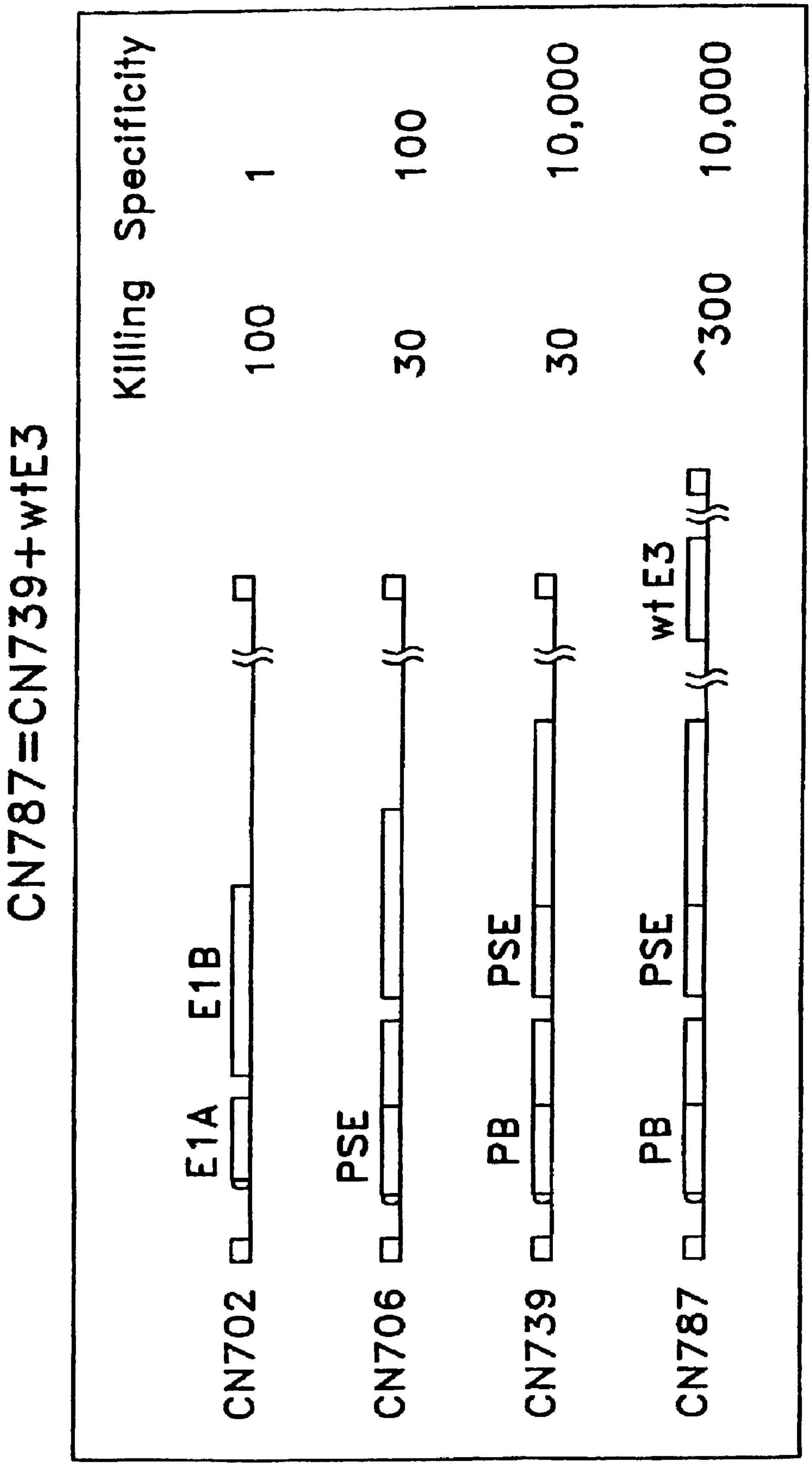
FIG. 2 is a schematic representation of adenovirus vector CN702, which is wild-type but E3-deleted, and recombinant adenovirus vectors CN706 (lacking E3), CN739 (lacking E3), and CN787 (containing E3). With respect to adenoviral constructs (as opposed to precursor plasmid constructs), it is understood that "CN" and "CV" designations may be used interchangeably. For example, CN787 and CV787 refer to the same adenoviral construct.

Adenovirus containing E3 were generated by homologous recombination in 293 cells. Briefly, CN257 was co-transfected with pBHGE3 (Microbix) into 293 cells. The cells were overlaid with media, and infectious virus generated by in vivo recombination was detected by cytopathic effect and isolated. Plaque-purified stocks of an adenovirus vector, designated CN787, were established. The structure of the recombinant virus was characterized by PCR, restriction endonuclease digestion and Southern blot. The resulting recombinant virus, CN787 (also referred to as CV787), is a full-length Ad5 with a PB-TRE driving the expression of E1A and a PSA-TRE driving expression of E1B, and which also contains an E3 gene. Thus, CN787 is analogous to CN739, except that it contains an E3 region. This construct is depicted schematically in FIG. 2.

Figure 11:
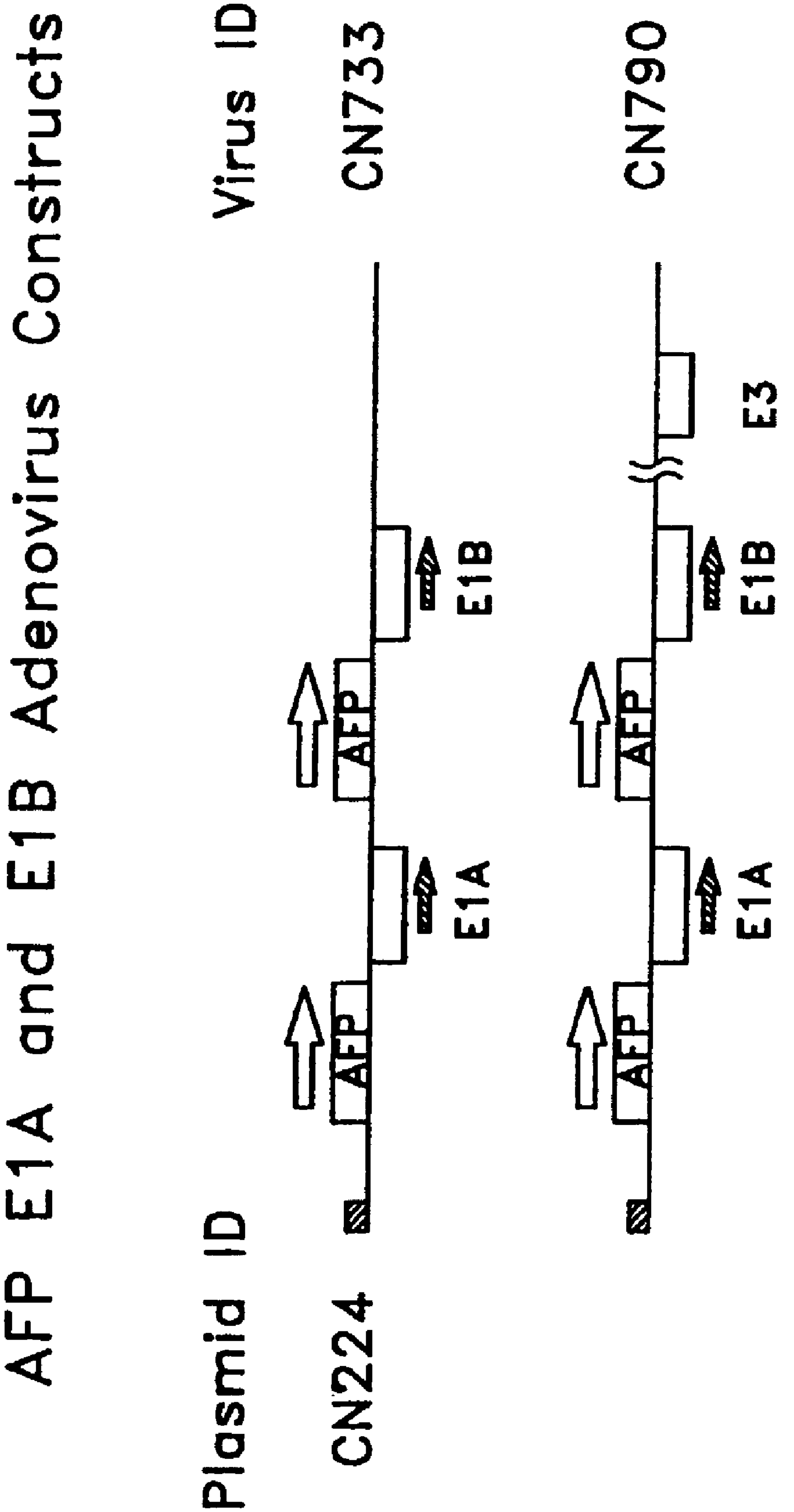
FIG. 11 is a schematic representation of adenoviral vectors CN733 and CN790.

Using this method, CN790, CN797, CN798, CN799, and CN802 (also referred to as CV790, CV797, CV798, CV799 and CV802, respectively) were generated by recombination between BHGE3 and CN733, CN796, CN532, CN525, and pXC.1, respectively. Plasmid pXC.1 (Microbix) is wild-type adenovirus Type 5. CN790 is the same as CN733 but with the addition of the Ad5 full-length E3 region. CN790 is depicted schematically in FIG. 11; CN798, CN799, and CN802 are depicted schematically in FIG. 16; and CN797 is depicted schematically in FIG. 19.

Structure, Genomic Stability, and Self-Inactivation of Viruses

Virus genetic structures were confirmed by PCR and Southern blot analysis.

Southern Blot Analysis. 10 ng of viral DNA (QIAmp blood kit, Qiagen) was digested with AflII or AflII and ClaI. DNA was fractionated through a 1% agarose gel and transferred by capillary transfer to a Nytran nylon membrane (Schleicher and Schuell). Viral DNA was probed with [$\alpha$-$^{32}$P] dCTP labeled PCR products specific for E1a or E1b sequences. The E1A probe was made by PCR from CN706 DNA amplifying a 938 bp fragment of Ad5 DNA with primers

```
                                       (SEQ ID NO:20)
5' GAGACATATT ATCTGCCACG G 3' (18.184.1);
and

                                       (SEQ ID NO:21)
5' CGTTAAGCAA GTCCTCGATA C 3' (18.184.2),
```

and the E1b probe was made from CN706 DNA using primers

```
                                       (SEQ ID NO:22)
(5' TTGGTTTTGG AGGTTTCTGT GGGG 3' (46.135B);
and

                                       (SEQ ID NO:23)
(5' AAAGGCCACC CTATCCTCCG TATC 3' (46.135E)
(881bp product).
```

Blots were hybridized overnight at 45° C. in ZipHyb solution (Ambion), washed two times in 2×SSC, 0.1% SDS at room temperature and two times in 0.1×SSC, 0.1% SDS at 65° C. Blots were visualized by exposure in a GS-525 Molecular Imager (BioRad Laboratories). The proportion of CN733 or CN790 deletion mutant (ΔE1a CN733 or ΔE1a CN790) in each stock was estimated by determining the amount of radioactivity in bands corresponding to the CN733 or CN790 (5.2 kb band, AflII digest and E1b probe) and the ΔE1a CN733 or ΔE1a CN790 (3.2 kb band) using the Molecular Imager and Multi-Analyst imaging software (Bio-Rad, version 1.0.2).

Figure 29B:
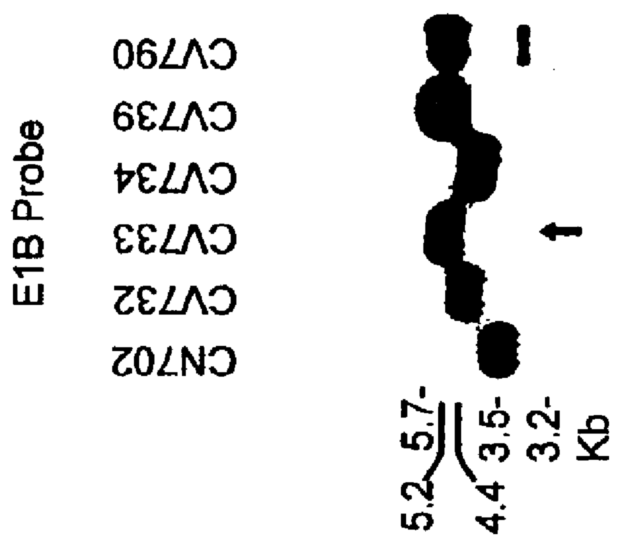
FIG. 29 is a half-tone reproduction of Southern blots of viruses hybridized with a 938 bp $^{32}$P-labeled E1a probe (FIG. 29A), or with an 881 bp $^{32}$P-labeled E1b probe (FIG. 29B).
Figure 29A:
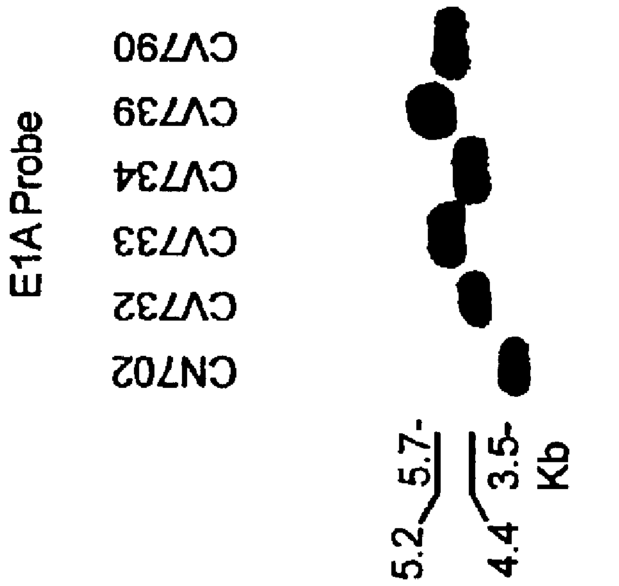

Results. Viral DNA was digested with AflII to release the E1 region and probed with [$\alpha$-$^{32}$P] dCTP labeled DNA specific for the E1a gene (FIG. 29A) and the E1b gene (FIG. 29B). The expected fragment sizes are shown in Table 1.

TABLE 1

| | Expected Fragment Sizes (kb) | |
|---|---|---|
| Virus | E1A Probe AflII | E1B Probe AflII |
| CN702 | 3.5 | 3.5 |
| CN732 | 4.4 | 4.4 |
| CN733 | 5.2 | 5.2 |
| ΔE1a CN733 | — | 3.2 |
| CN734 | 4.4 | 4.4 |
| CN739 | 5.7 | 5.7 |
| CN790 | 5.2 | 5.2 |
| ΔE1a CN790 | — | 3.2 |

Figure 30:
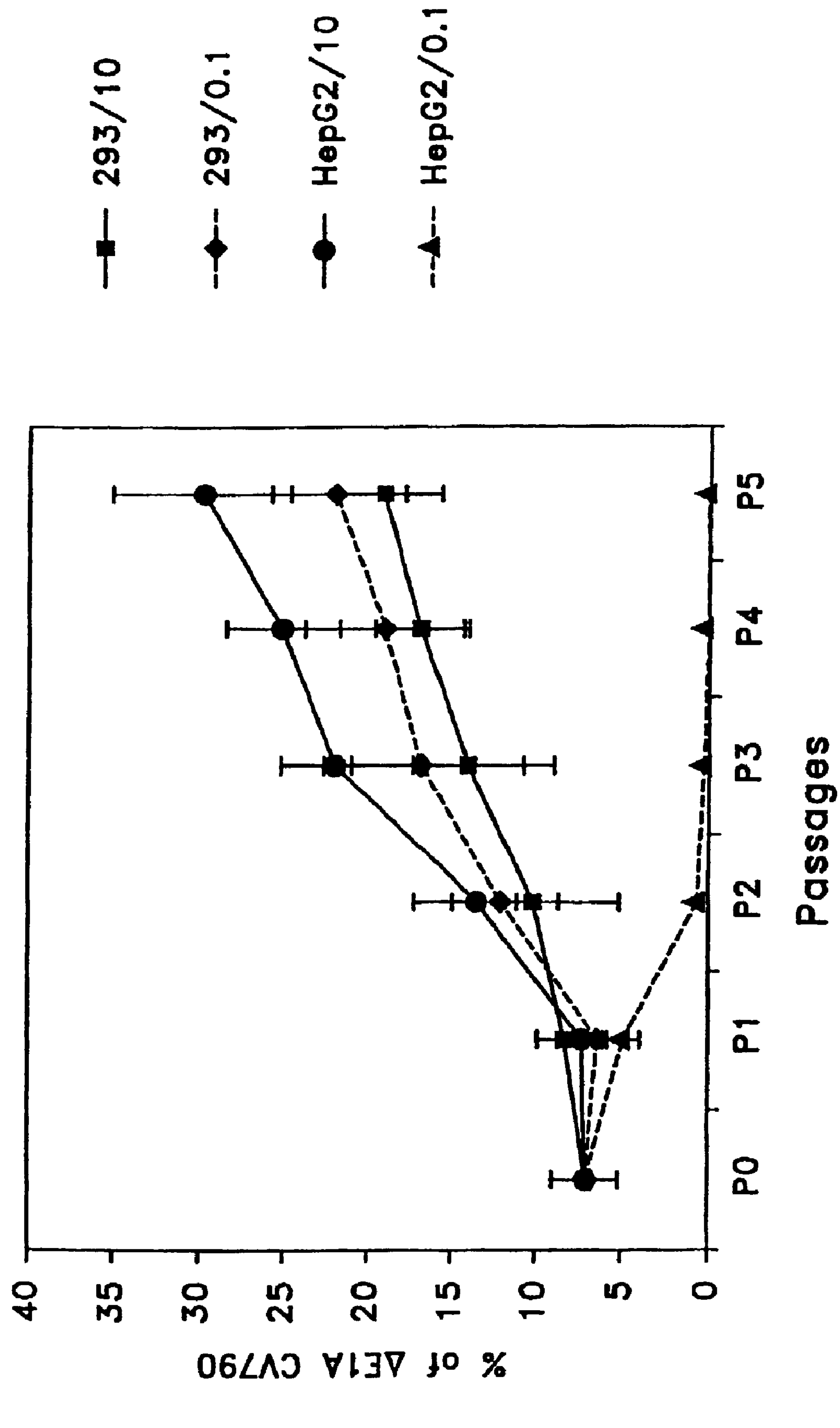
FIG. 30 is a graph depicting accumulation of deletion mutants, as measured by Molecular Imager scans of Southern blot radiograms as prepared in FIG. 29B. CN790 was prepared serially through 5 passages in 293 cells at MOI=10 (square) and MOI=0.1 (diamond), and in HepG2 cells at MOI=10 (closed circles) and MOI=0.1 (triangles).

All the viruses had the expected structure and CN702, CN732, CN734 and CN739 were stable through three passages. However, preparations of CN733 and CN790 showed the expected virus, indicated by a 5.2 kb band, but also contained an additional 3.2 kb band (FIG. 29B). This band did not appear in Southern blots probed with E1a but did appear in Southern blots probed with E1b. The DNA of individual clones of CN733 and CN790 were cloned and their DNAs sequenced. DNA sequence analysis of individual clones indicated homologous recombination occurred between the two AFPs and the AFP DNA segments during propagation, resulting in the deletion of the E1a gene and one copy of the AFP TRE. These deletion viruses were named ΔE1a CN733 and ΔE1a CN790 respectively. The rate of accumulation of ΔE1a CN733 and ΔE1a CN790 in stocks of CN733 and CN790 was evaluated by performing Southern blot analysis on several viral stocks prepared in series. Data presented in FIG. 30 indicate that ΔE1a CN790 was 7% at the first passage and accumulated to about 14% of the total viral particles by the third passage in 293 cells. ΔE1a CN790 accumulated rapidly in cells that did not select against the replication defective mutant like 293 cells or in cells that had been infected at an MOI=10. However, CN790 prepared at low MOI=0.1 in $AFP^+$ HepG2 cells that did not support replication defective adenovirus replication was devoid of the deletion mutant after three passages (FIG. 30).

Example 2

In vitro and in vivo Characterization of CN787, an E3-containing Adenoviral Construct Comprising a PB-TRE Driving Expression of E1A and a PSA-TRE Driving Expression of E1B Cells and Culture Methods LNCaP cells were obtained at passage 9 from the American Type Culture Collection (Rockville, Md.). LNCaP cells were maintained in RPMI 1640 medium (RPMI) supplemented with 10% fetal bovine serum (FBS; Intergen Corp.), 100 units/mL of penicillin, and 100 units/mL streptomycin. LNCaP cells being assayed for luciferase expression were maintained in 10% strip-serum (charcoal/dextran treated fetal bovine serum to remove T3, T4, and steroids; Gemini Bioproduct, Inc., Calabasas, Calif.) RPMI. The cells were periodically tested for the production of PSA which was consistently above 20 ng/mL per day.

Transfections of LNCaP Cells

For transfections, LNCaP cells were plated out at a cell density of $5\times10^5$ cells per 6-cm culture dish (Falcon, N.J.) in complete RPMI. DNAs were introduced into LNCaP cells after being complexed with a 1:1 molar lipid mixture of N-[1-(2,3-dioleyloxy)propyl-N,N,N-trimethylammonium chloride (DOTAP™; Avanti Polar Lipids, Ala.) and dioleoyl-phosphatidylethanolamine (DOPE™; Avanti Polar Lipids, Ala.); DNA/lipid complexes were prepared in serum-free RPMI at a 2:1 molar ratio. Typically, 8 μg (24.2 nmole) of DNA was diluted into 200 μL of incomplete RPMI and added dropwise to 50 nmole of transfecting, lipids in 200 μL of RPMI with gentle vortexing to insure homogenous mixing of components. The DNA/lipid complexes were allowed to anneal at room temperature for 15 minutes prior to their addition to LNCaP cells. Medium was removed from LNCaP cells and replaced with 1 mL of serum-free RPMI followed by the dropwise addition of DNA/lipid complexes. Cells were incubated with complexes for 4–5 hours at 37° C., 5% $CO_2$. Medium was removed and cells washed once with PBS. The cells were then trypsinized and resuspended in 10% strip-serum RPMI (phenol red free). Cells were replated into an opaque 96-well tissue culture plate (Falcon, NJ) at a cell density of 40,000 cells/well per 100 μL media and assayed. Varying amounts of drugs (e.g. androgens and anti-androgens) were added 16 hours later and assayed for luciferase activity 32 hours thereafter.

Plaque Assays

To determine whether the adenoviral constructs described above replicate preferentially in prostate cells, plaque assays were performed. Plaquing efficiency was evaluated in the following cell types: prostate tumor cell lines (LNCaP), breast normal cell line (HBL-100), ovarian tumor cell line (OVCAR-3, SK-OV-3), and human embryonic kidney cells (293). LNCaP cells express both androgen receptor and PSA, while the other cell lines tested do not. 293 cells serve as a positive control for plaquing efficiency, since this cell line expresses Ad5 E1A and E1B proteins. For analyzing constructs comprising a CEA-TRE, cells that allow a CEA-TRE to function, such as NCIH508, LoVo, SW1463, MKN1, MKN28, MKN45 and cells that do not allow such function, such as HuH7, HeLa, PA-1, or G361, are used. For analyzing constructs comprising an AFP-TRE, cell lines which express AFP, such as HepG2 and Hep3B, are compared with cell lines which do not express AFP, including HBL-100, OVCAR-3, and LNCaP. The plaque assay was performed as follows: Confluent cell monolayers were seeded in 6-well dishes eighteen hours before infection. The monolayers were infected with 10-fold serial dilutions of each virus. After infecting monolayers for four hours in serum-free media (MEM), the media was removed and replaced with a solution of 0.75% low melting point agarose and tissue culture media. Plaques were scored two weeks after infection. CN702 has no modifications in its E1 region, but is devoid of E3, and thus serves as a wild type control for left end modifications lacking E3. CN706 demonstrates selective cytotoxicity toward PSA-expressing cells in vitro and in vivo. Rodriguez et al. (1997) *Cancer Res.* 57:2559–2563.

In vitro Characterization of CN787

Various parameters of CN787 were measured, including cell type specificity, plaque size, extracellular virus yield, kinetics of cell killing, and total viral yield per cell.

Cell Type Specificity of CN787

Figure 3:
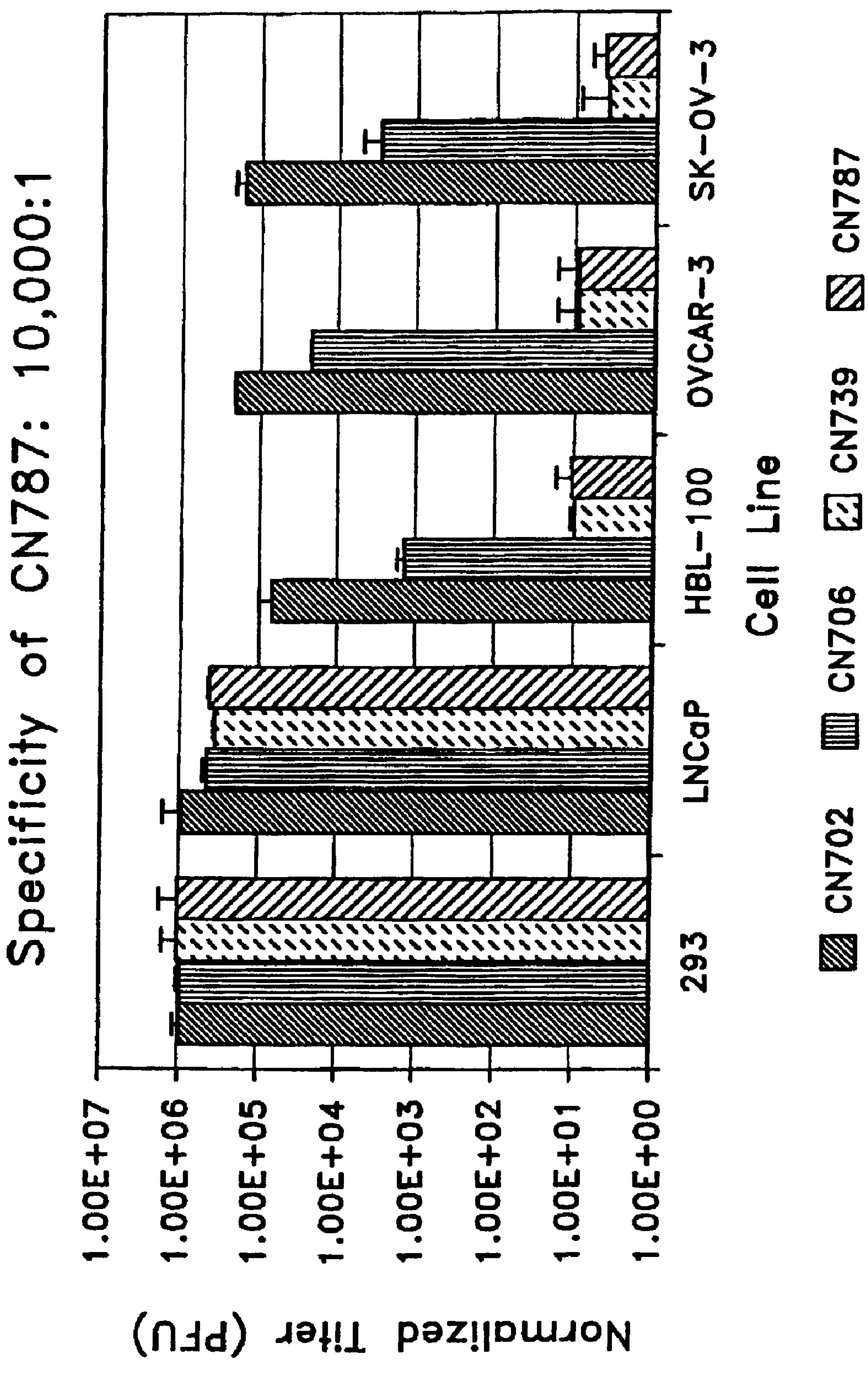
FIG. 3 is a bar graph depicting the titer, normalized to the titer of CN702 on 293 cells, of CN702 (first bars), CN706 (second bars), CN739 (third bars), and CN787 (fourth bars) in various cell lines.

To determine whether adenoviral construct CN787, described above, replicate preferentially in prostate cells, plaque assays were performed as described above. The results are shown in FIG. 3. The results are also summarized in FIG. 2, where they are expressed as percent of wild-type adenovirus plaque-forming units (PFU) per ml. The average titer of duplicate samples for the viruses tested. The titer for a particular virus in all cell lines was normalized to its titer on 293 cells. Once the titers on a cell type were normalized to 293 cells, the normalized numbers of the recombinant viruses were compared to CN702. A ratio of less than 100 suggests that the virus tested plaques less efficiently than CN702. Conversely, a ratio greater than 100 suggests that the virus plaques more efficiently than CN702. The ratio of specificity of CN787 to that of CN702 is 10,000:1.

These results indicate that CN787 exhibits a specificity for prostate cells comparable to that of CN739.

Viral Production

Figure 4:
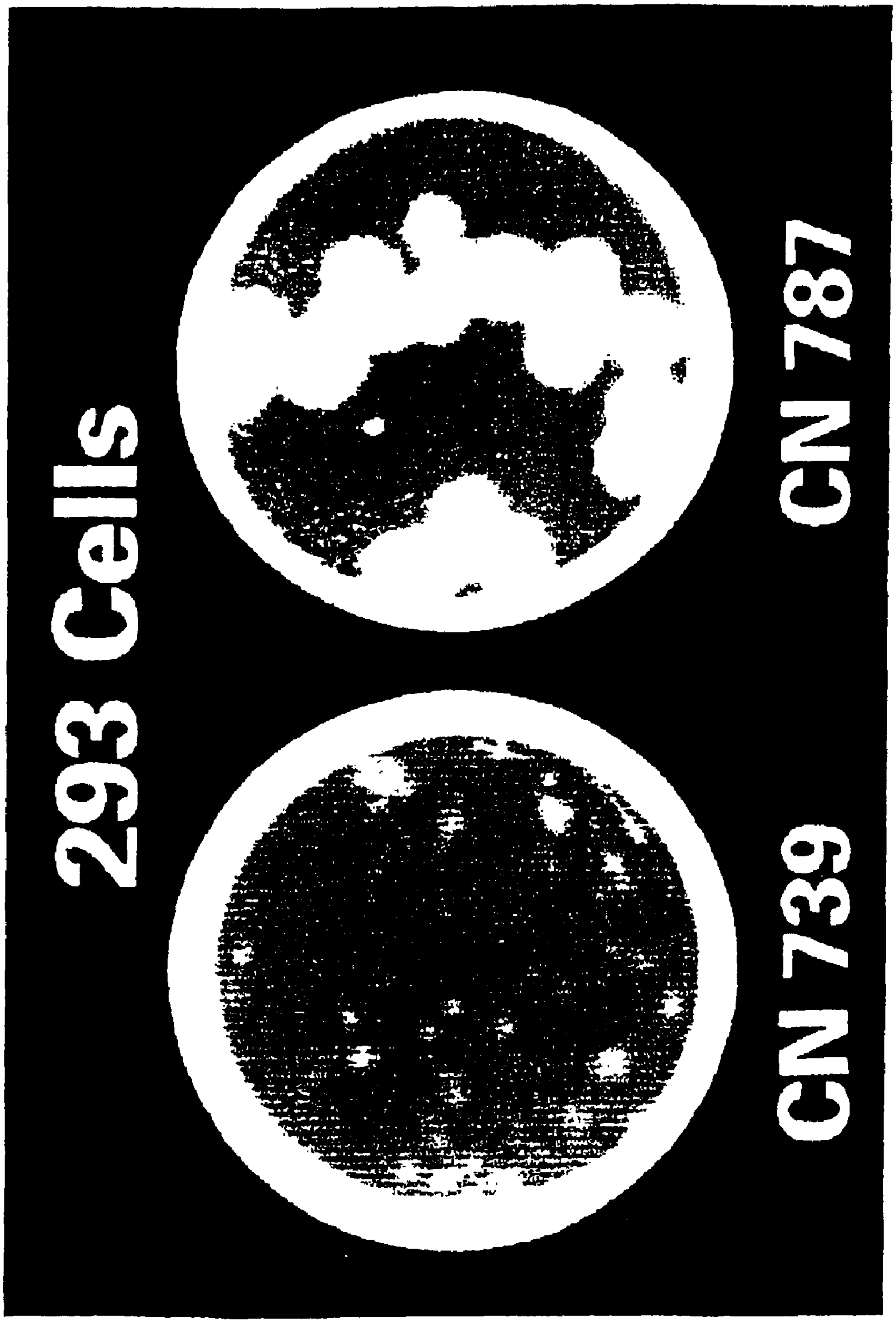
FIG. 4 is a half-tone reproduction of plaques formed by CN739 and CN787 on 293 cells.

While CN787 and CN739 demonstrate comparable cell-type specificity, CN787 gave much larger plaques than did CN739, as shown in FIG. 4.

Figure 5:
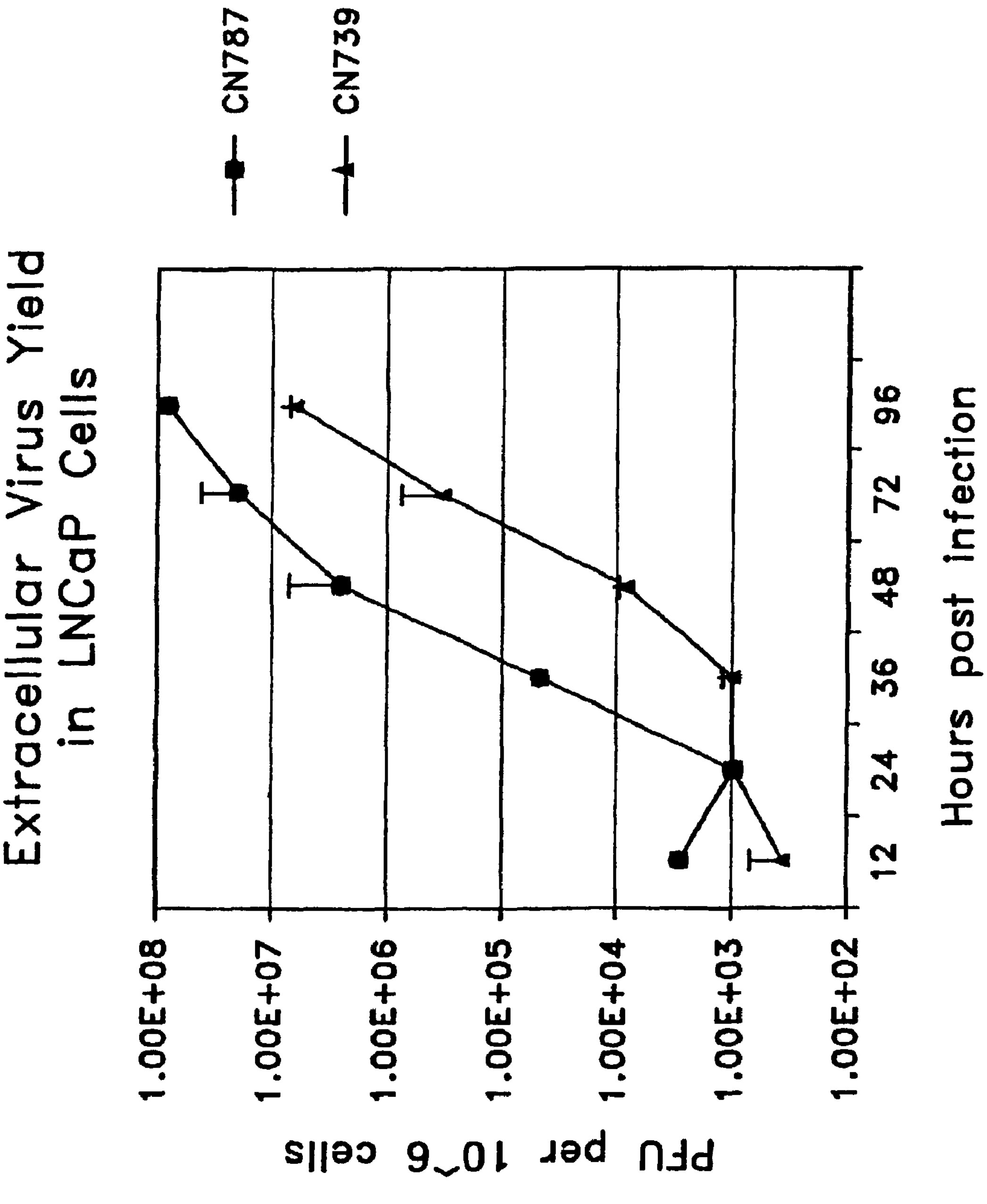
FIG. 5 is a graph depicting the extracellular viral yield, expressed as plaque-forming units (PFU), from LNCaP cells at various times post-infection, of adenoviral vectors CN739 (triangles) and CN787 (squares).

One measure of viral production is extracellular virus yield per cell. CN787 and CN739 were plated on LNCaP cells at 2 PFU/cell, and plated at $10^6$ cells per well. At various times after infection, the cell supernatant was tested on 293 cells to measure the number of plaque-forming units. The results, presented in FIG. 5, show that CN787 gave a significantly higher viral yield than did CN739.

Figure 6:
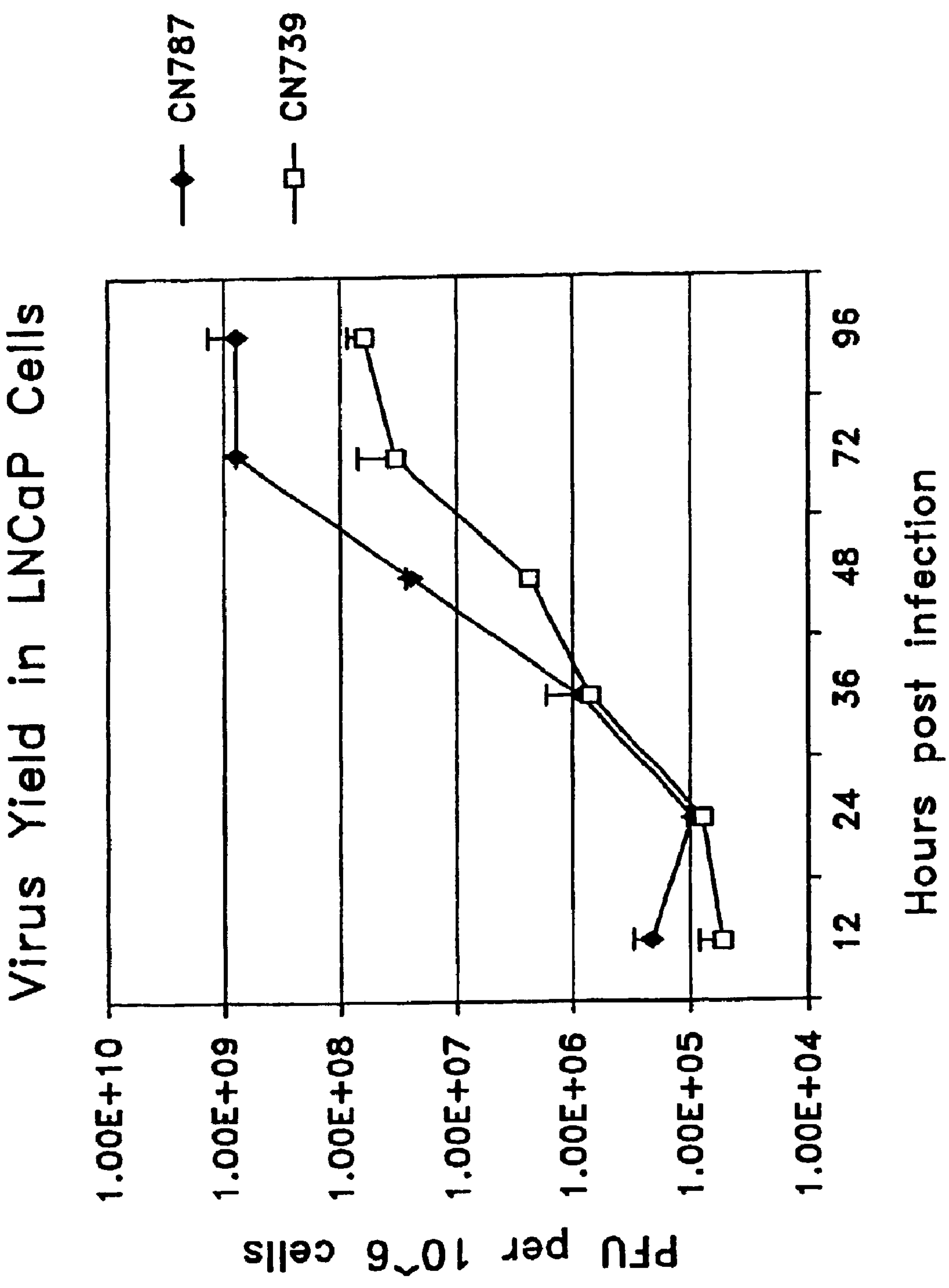
FIG. 6 is a graph depicting, at various times post-infection, the total virus yield, expressed as plaque-forming units (PFU), in LNCaP cells infected with CN739 (squares) or CN787 (diamonds).

When total virus yield was examined, it was found that, at 96 hours post infection, CN787 yielded at least one log higher number of plaque forming units per cell, as shown in FIG. 6. The total viral yield per cell is the extracellular viral yield per cell plus the intracellular viral yield per cell. CN787 yielded more extracellular virus per cell than did CN739, indicating that that E3 mediates a fast release of viruses from the infected cells. The total viral yield per cell from cells infected with CN787 is higher than that of cells infected with CN739, suggesting that CN787-infected cells produce more viruses. The higher total yield could be due to virus replication/DNA replication, or a higher efficiency of viral DNA packaging.

Figure 7:
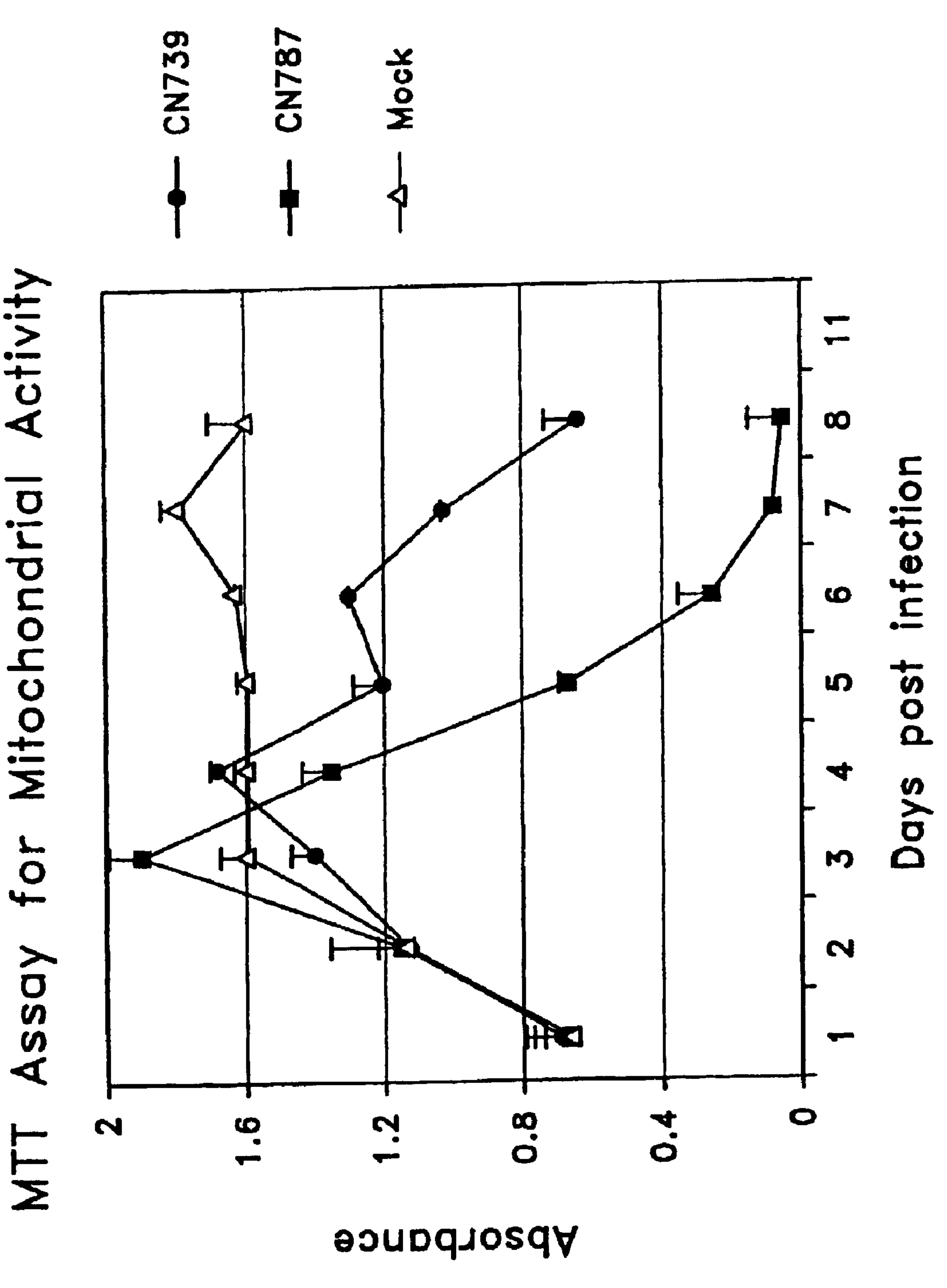
FIG. 7 is a graph depicting the results of an MTT assay for cytotoxicity, versus days post infection, of CN739-infected (circles), CN787-infected (squares), and mock-infected (triangles) LNCaP cells.

To examine the kinetics of cell killing by CN787, two different assays for cell viability, the MTT assay and the trypan blue dye exclusion assay, were performed. The MTT (3-(4,5-Dimethylthiazol-2-yl)-2,5-diphenyl-2H-tetrazolium bromide) assay was performed as follows. 293 cells were infected with CN787 or CN739 at a concentration of 2 PFU/cell and plated at a cell density of $10^4$ cells per well at various times post-infection. At the indicated times post-infection, 25 $\mu$l MTT (Sigma Chemical Co., St. Louis, Mo.) in PBS at a concentration of 5 mg/ml was added to each well. After 2 hours, lysis buffer (20% sodium dodecyl sulfate in 50:50 dimethyl formamide:double-distilled $H_2O$, pH 4.7) was added to each well and plates were incubated overnight at 37° C. Plates were read on a microplate reader at 570 nm. Samples were in triplicate. The results, shown in FIG. 7, indicate that when cells were infected with CN787, the absorbance dropped sharply after 4 days post infection, and by 7 days post-infection, virtually all cells were killed. In contrast, cells were killed less rapidly by CN739, which is analogous to CN787 but lacks an E3 region.

Figure 8:
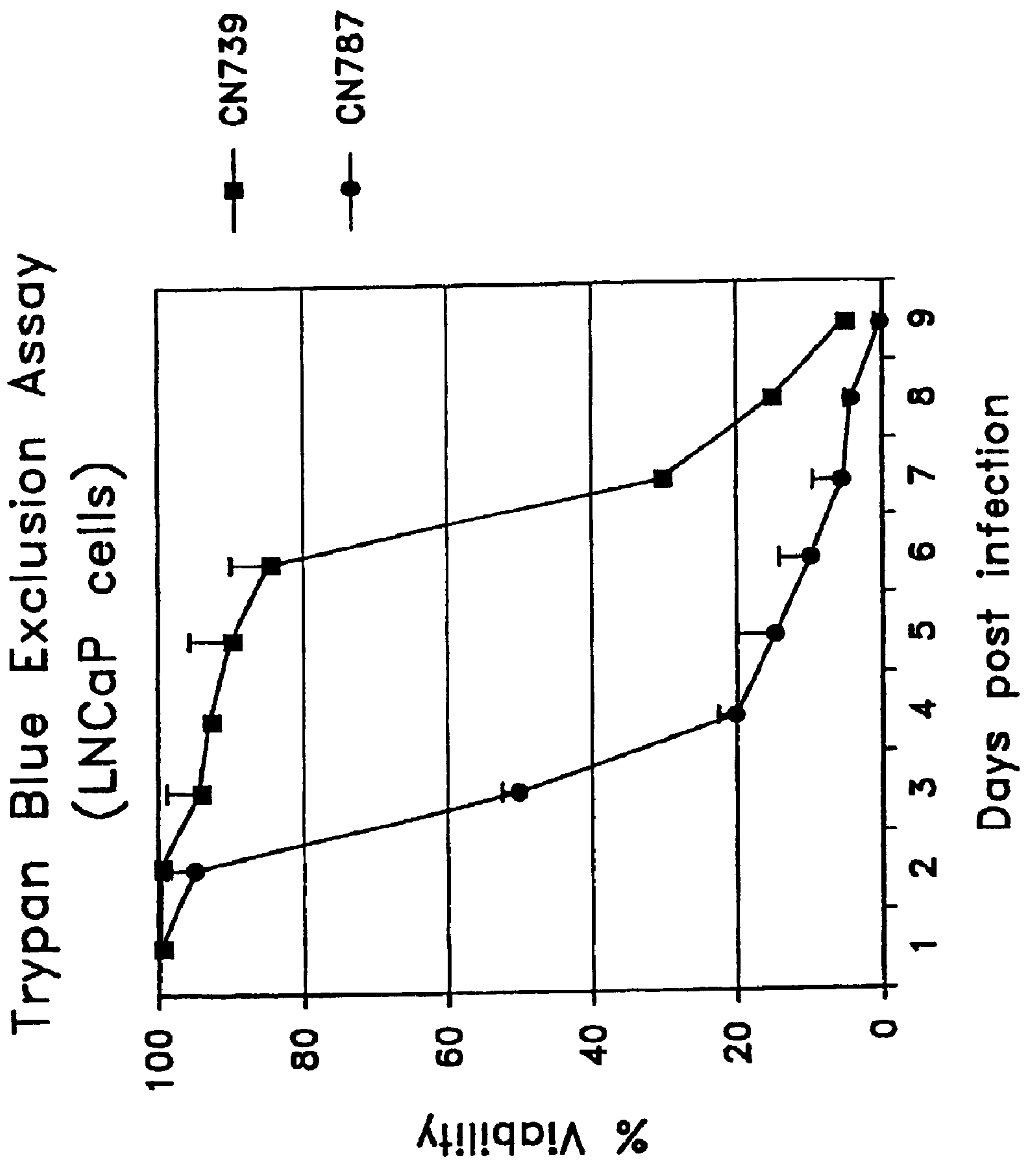
FIG. 8 is a graph depicting viability, as measured by trypan blue exclusion, versus days post infection of LNCaP cells infected with CN739 (squares) or CN787 (circles).

As a second assay for cell viability, trypan blue exclusion was performed. At various times after infection, a sample of cells $10^6$ LNCaP cells was removed. Cells were separated from the medium and trypsinized. Trypan blue (Gibco BRL, Gaithersberg, Md.) was added to a final concentration of 0.02%. Cells were counted on a hemacytometer. As with the MTT assay, the trypan blue exclusion assay (FIG. 8) showed that a reduction in viability to 50% viability of LNCaP cells was achieved in 3 days by CN787, compared with 6.5 days by CN739. Thus, by two different assays, LNCaP cells were killed more rapidly by CN787 than by CN739.

In vivo Characterization of CN787

An especially useful objective in the development of prostate-specific adenoviral vectors is to treat patients with prostate carcinoma. An initial indicator of the feasibility is to test the vectors using a technique known in the art, such as testing the vectors for cytotoxicity against cancer cells such as tumor xenografts grown subcutaneously in Balb/c nu/nu mice. Mice are given subcutaneous injections with $1\times10^7$ carcinoma cells, such as LNCaP or HepG2, in PBS. Tumor cells can be tested for secretion of a tumor-specific product, such as, for example, PSA or AFP, by assaying for the product in serum using standard assays (for example, ELISA). Alternatively, as described below, tumor volume can be measured.

Figure 9:
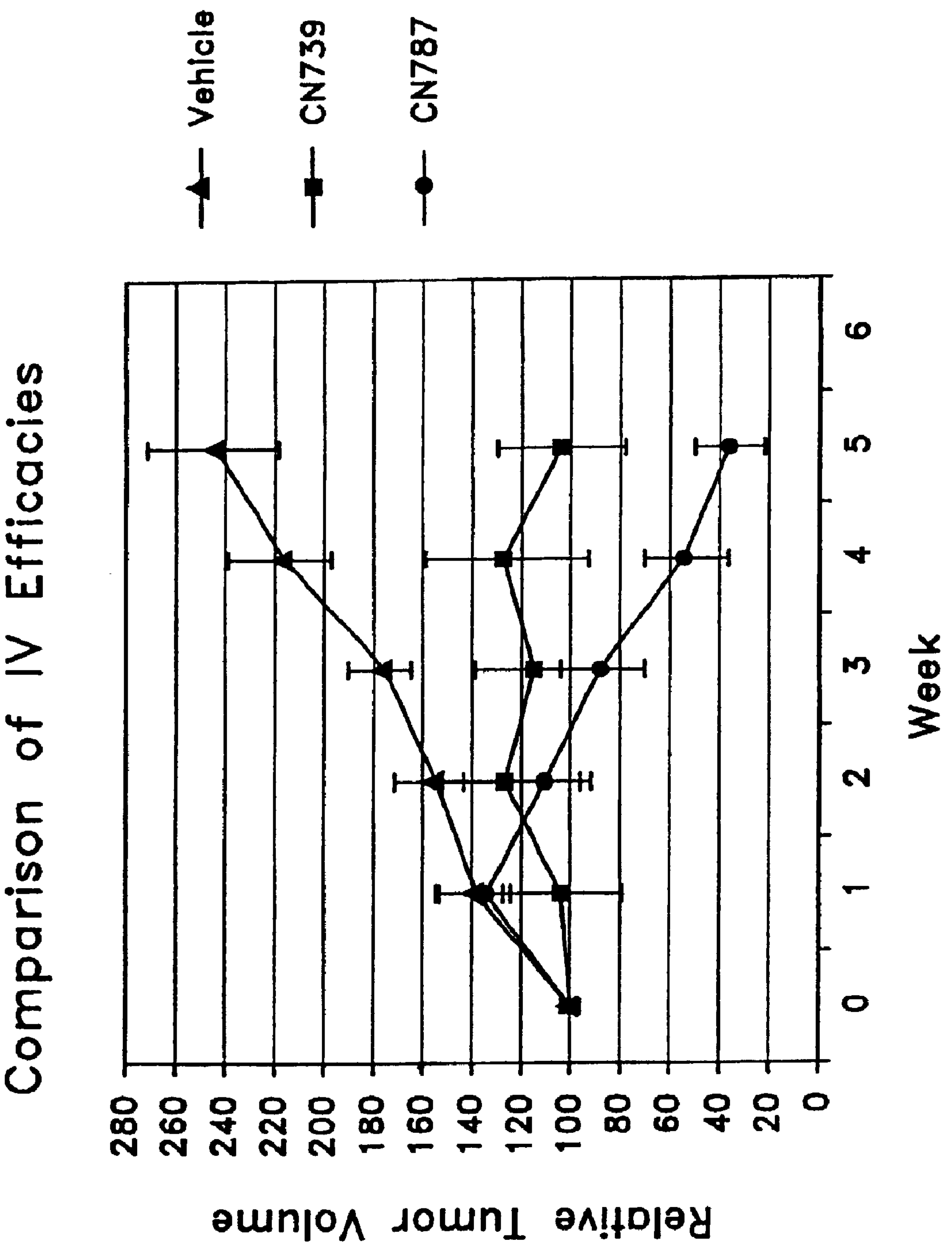
FIG. 9 is a graph depicting relative tumor volumes over a period of five weeks in mice with tumor xenografts. The mice were treated with CN739 (squares), CN787 (circles), or vehicle alone (triangles).

LNCaP nude mouse xenografts were challenged with a single intratumoral dose ($1\times10^4$ particles/$mm^3$ tumor) of either CN787, a vector containing the E3 gene, or CN739, a vector lacking the gene. A third group of tumors was treated with buffer alone. The tumors were monitored weekly for six weeks and their relative volume was graphed against time. The results are shown in FIG. 9. Error bars represent the standard error for each sample group. The initial average tumor volume for CN787 treated animals (n=7) was 270 $mm^3$, 295 $mm^3$ for CN739 treated (n=7), and 270 $mm^3$ for buffer treated (n=7). The data suggest that CN787 kills tumor cells more effectively than CN739. On average, tumors challenged with CN739 remained the same size throughout the course of the experiments. Those treated with vehicle alone more than doubled in size. Tumors challenged with CN787 were reduced in size by 40% by week 5. The Students T-test indicates that the difference in tumor size between CN787 and CN739 treated tumors was statistically significant from week 3 through the end of the experiment (p=0.00209).

Figure 10:
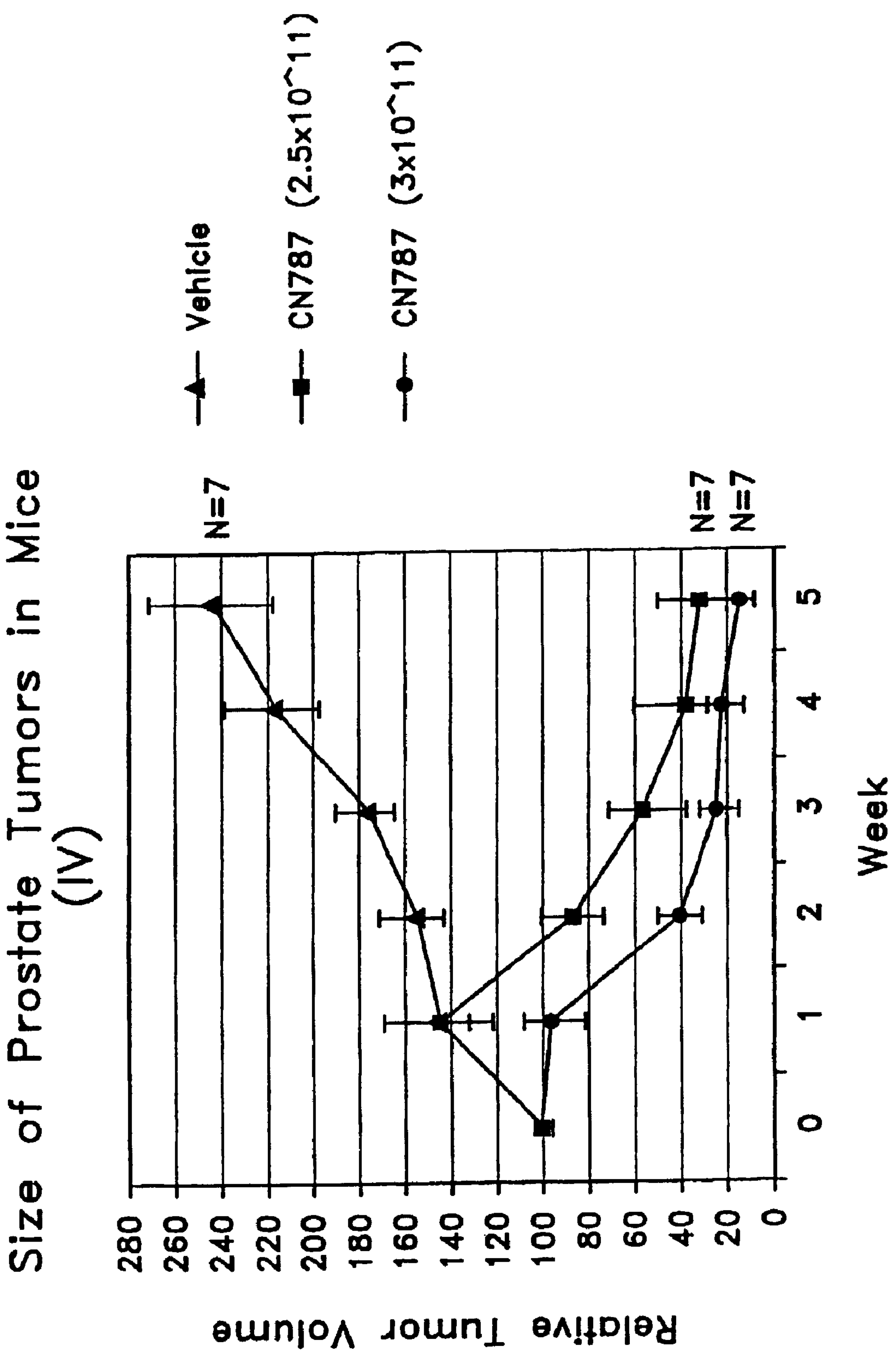
FIG. 10 is a graph depicting relative tumor volumes over a period of four weeks in mice with tumor xenografts. The mice were treated with $2.5\times10^{11}$ PFU CN787 (squares), $3\times10^{11}$ PFU CN787 (circles), or vehicle alone (triangles).

FIG. 10 presents the results of regimen optimization efforts. LNCaP nude mouse xenografts were challenged with $5\times10^{10}$ CN787 viral particles per day for 5 days (total of $2.5\times10^{10}$ particles CN787) ($p=1.47\times10^{-5}$) or $1\times10^{11}$ CN787 viral particles per day for 3 days (total of $3\times10^{11}$ CN787 viral particles)($p=9.2\times10^{-7}$).

Example 3

In vitro and in vivo Characterization of CN790, an E3-containing Adenoviral Construct Comprising AFP-TREs Driving Expression of E1A and E1B In vitro Characterization of CN790

Figure 12:
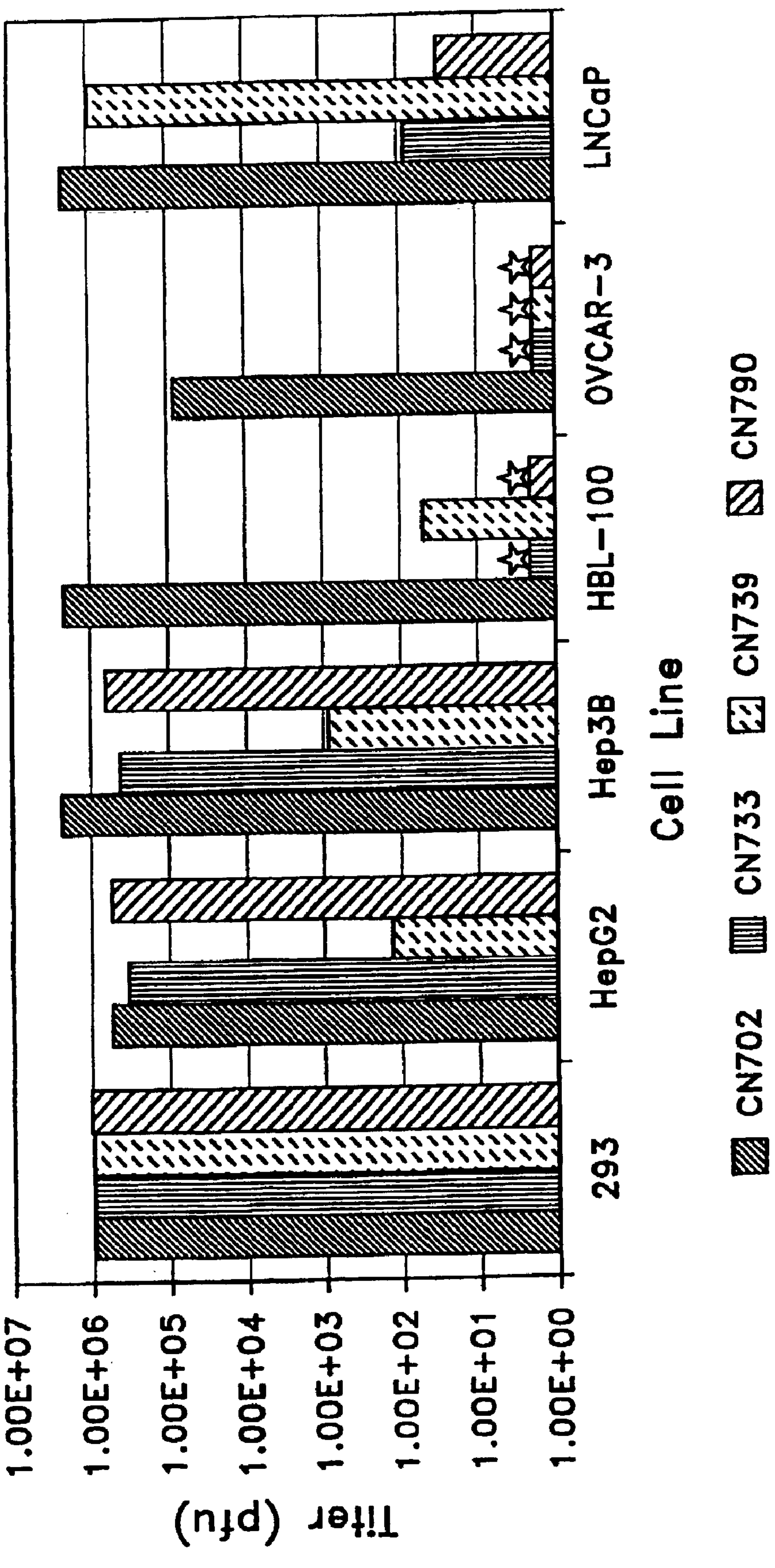
FIG. 12 is a bar graph depicting the plaquing efficiency of CN702, CN733, CN739, and CN790 in various cell lines. For each cell line tested, the first, second, third and fourth bars represent the results obtained with CN702, CN733, CN739, and CN790, respectively. A star over a bar indicates no detectable plaques.

To determine whether adenoviral construct CN790, described above, replicates preferentially in liver cells, plaque assays were performed as described in Example 2. The results, shown in FIG. 12, are expressed as percent of wild-type (CN702) adenovirus plaque-forming units (PFU) per ml. The average titer of duplicate samples for the viruses tested. The titer for a particular virus in all cell lines was normalized to its titer on 293 cells. Once the titers on a cell type were normalized to 293 cells, the normalized numbers of the recombinant viruses were compared to CN702. A ratio of less than 100 suggests that the virus tested plaques less efficiently than CN702. Conversely, a ratio greater than 100 suggests that the virus plaques more efficiently than CN702.

CN790 showed a plaquing efficiency comparable to that of CN733 on HepG2 and Hep3B cells. The results indicate that CN790 demonstrates specificity for hepatic cells comparable to that of CN733.

Virus yield assay. Twenty-four well dishes (Falcon) were seeded with 200,000 cells per well of Hep3B, HepG2, LNCaP, OVCAR-3, or SK-Hep-1 cells 24 hr prior to infection. Cells were infected at an MOI of 2 PFU/cell for three hours in serum-free media. After the infection was complete, the virus containing media was removed, monolayers were washed three times with PBS, and one ml of complete media was added to each well. 72 hrs post infection, cells were scraped into the culture medium and lysed by three cycles of freeze-thaw. Two independent infections of each virus cell-combination were titered in duplicate on 293 cells.

Figure 32:
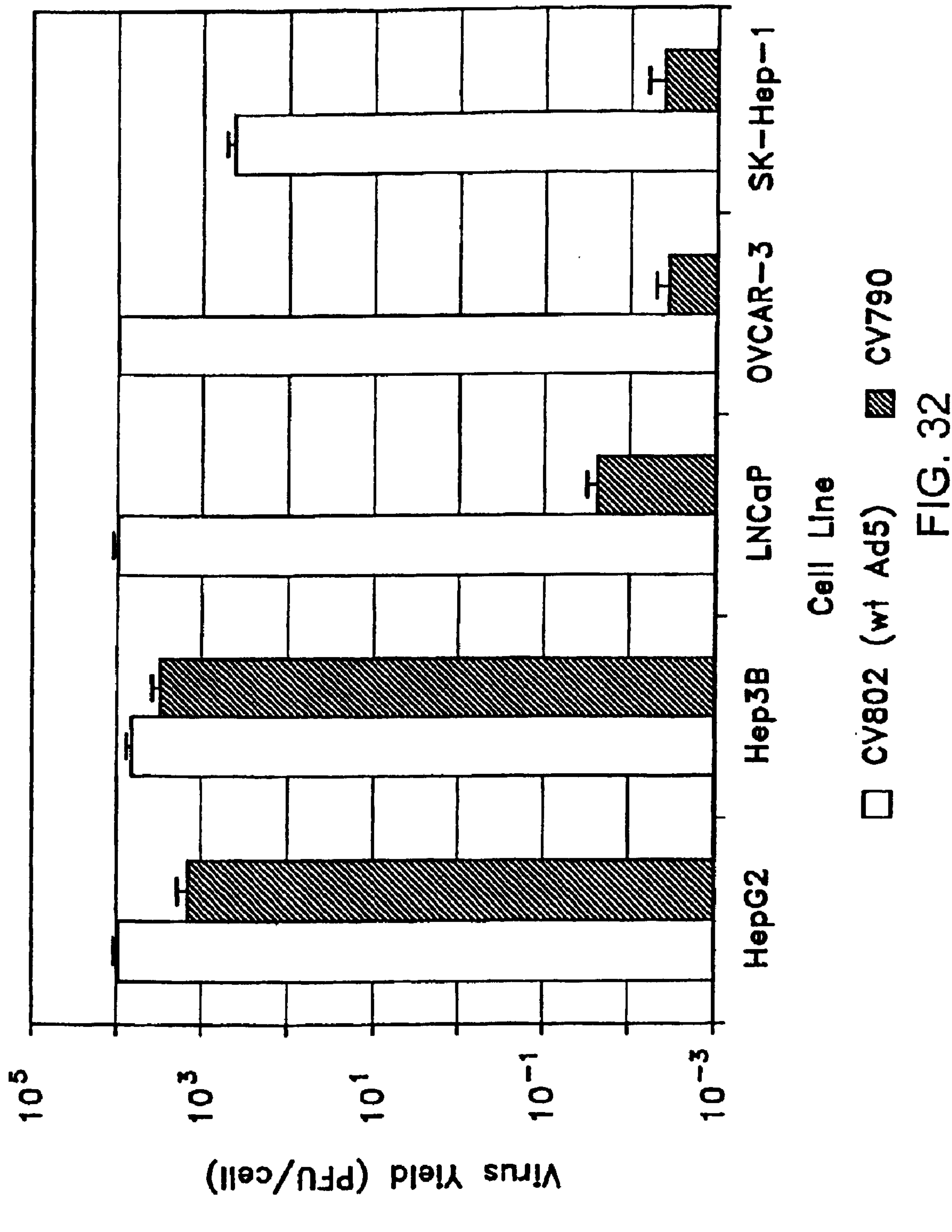
FIG. 32 is a bar graph depicting the virus yield of CN790 (shaded bars) and wt Ad5 (open bars, CN802) in various cell lines.

Results. The addition of the Ad E3 region did not alter virus cell tropism. Cell lines were infected with either CN790 or CN802 (wt Ad5) at a multiplicity of infection (MOI) of 2 PFU/cell. Progeny virus yield was determined 72 hrs after infection by plaque assay on 293 cells (FIG. 32). In $AFP^+$ cells (Hep3B, HepG2) CN790 replicated similarly to the wild-type control; only a 2–6 fold difference in virus yield was observed. However, CN790 replicated poorly in all $AFP^-$ cells tested (LNCaP, OVCAR-3, SK-Hep-1), producing a $10^5$- to $10^6$-fold lower virus yield than CN802. These data indicate that CN790 replicates efficiently in $AFP^+$ cells, but is significantly attenuated in $AFP^-$ cells. Comparison of CN733 and CN790 in the one-step growth curve in Hep3B and OVCAR-3 cells showed CN790 had the same level of specificity as CN733.

Cytopathic Effect of CN790

Cytopathic effect (CPE) assay was carried out to visually assess the specificity of CN790 cytolytic activity. Six well dishes (Falcon) were seeded at 300,000 cells per well with HepG2, Hep3B, Huh-7, LNCaP, OVCAR-3 and SK-Hep-1 cells 24 hr prior to infection. Cells were infected with CN790 or CN802 at an MOI of 10 PFU/cell, except for SK-Hep-1 cells, which were infected at an MOI of 20 PFU/cell. Virus adsorption was for three hours in 1 ml of serum-free media. Following adsorption, the virus containing media was removed and replaced with 3 ml of RPMI, 10% FBS. Seven days post infection, cells were stained with crystal violet.

Figure 33:
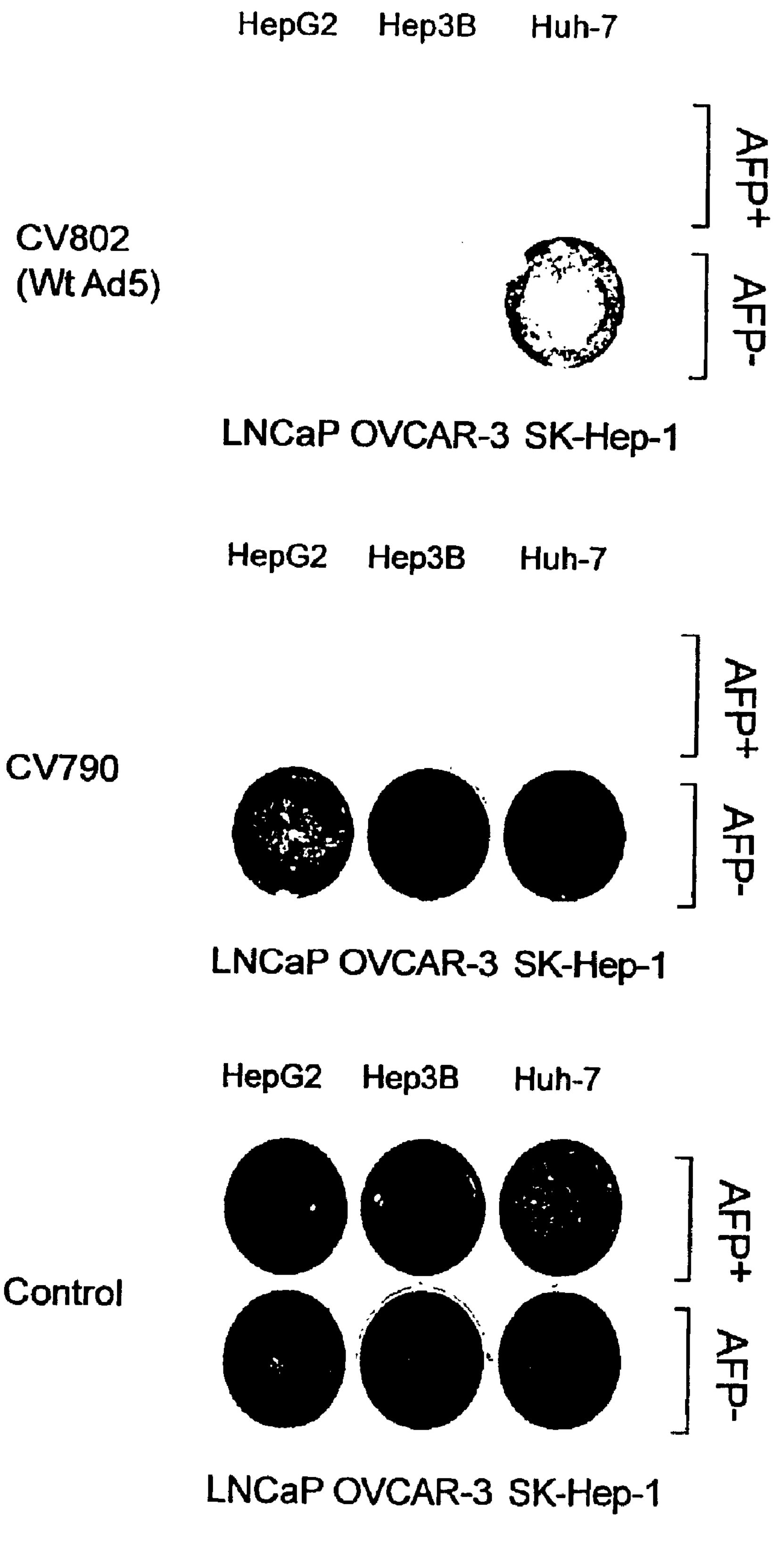
FIG. 33 is a half-tone reproduction of cells stained with crystal violet comparing cytotoxicity of CN790 and CN802 in various cell lines.

Three $AFP^+$ cell lines (Hep3B, HepG2, Huh-7) and three $AFP^-$ cell lines (LNCaP, OVCAR-3, SK-Hep-1) were mock infected (control) or infected with either CN790 or CN802 (wt Ad5) at an MOI of 10 PFU/cell. SK-Hep-1 cells were infected at an MOI of 20 PFU/cell. Cytopathic effect (CPE) seven days post-infection was monitored by staining remaining cells with crystal violet. The results are shown in FIG. 33.

The results indicate that CN790 caused complete CPE in the three AFP expressing cells, but caused little CPE in the three $AFP^-$ cells tested, including the $AFP^-$ hepatoma line SK-Hep-1. In contrast, wt Ad5 caused significant CPE in all cell lines tested regardless of AFP status. Thus, the cytolytic activity of CN790 is specific for $AFP^+$ cell lines and CN790 causes little toxicity to $AFP^-$ cells.

In vivo Characterization of CN790

The effect of CN790 on HepG2 tumors was tested using the tumor xenograft assay system. Six to eight week old athymic Balb/c nu/nu mice were obtained from Simonson Laboratories (Gilroy, Calif.). Xenografts were established by injecting 1–3x$10^6$ Hep3B or HepG2 cells subcutaneously near the small of the back suspended in 100 $\mu$l of RPMI. When tumors reached between 200 $\mu$l and 300 $\mu$l, mice were randomized and treated with 100 $\mu$l of CN790 by tail vein injection. Two treatment regimens were tested. First, Hep3B tumors were treated with 4x$10^9$ PFU of CN790 or vehicle alone (PBS+10% glycerol) on days 1, 4 and 8. Second, HepG2 tumors were treated with 5x$10^8$ PFU of CN790 or vehicle on days 1, 2, 3, 4, 5, 8, 9, 10, 11, and 12. Tumors were measured in two dimensions by external caliper and volume was estimated by the formula [length (mm)xwidth $(mm)^2$]/2. Animals were sacrificed when tumor burdens became excessive. Serum was harvested weekly by retro-orbital bleed.

Figure 13:
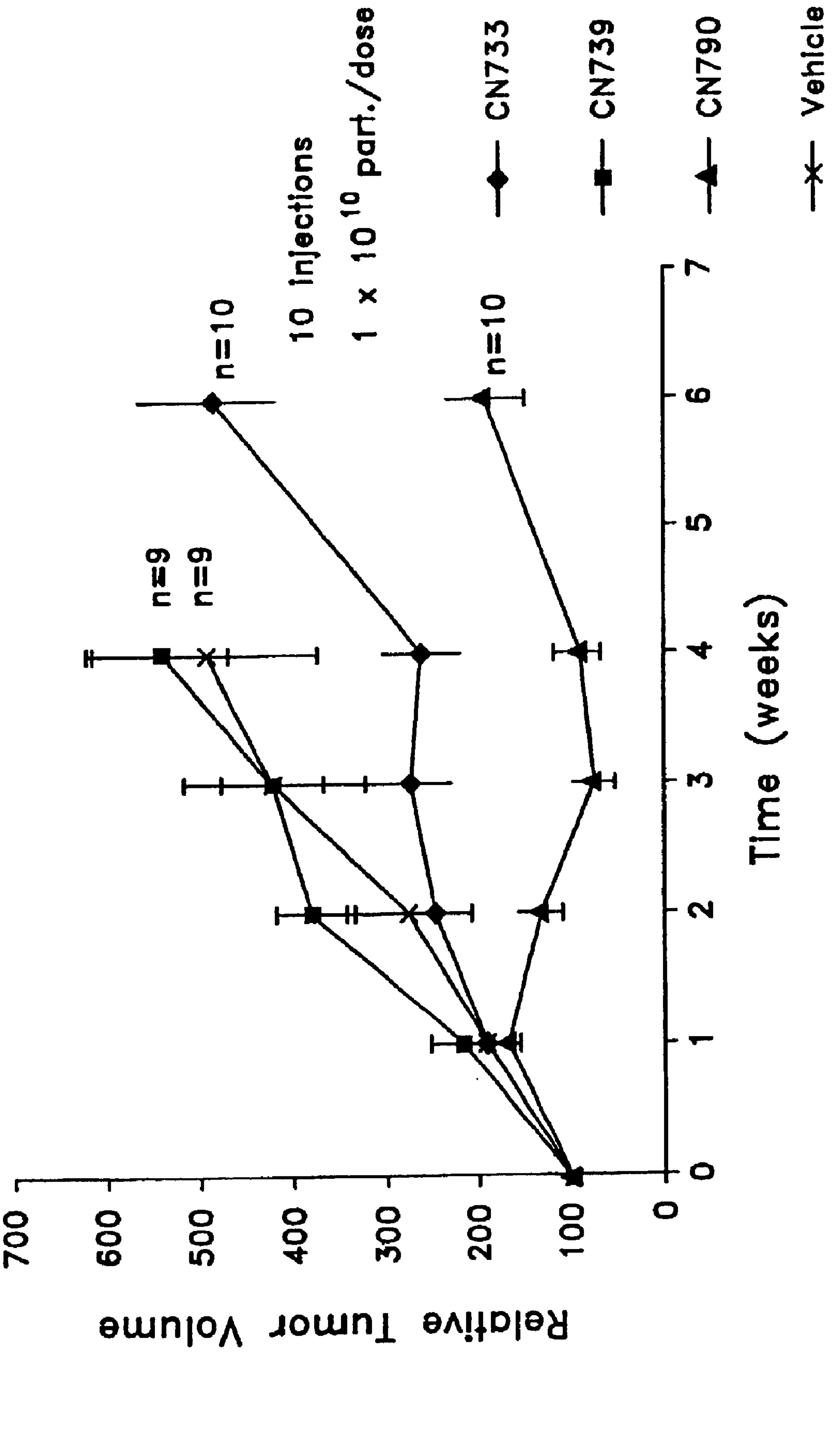
FIG. 13 is a graph depicting the relative tumor volumes over a period of six weeks in mice with HepG2 tumor xenografts. Mice were treated with 10 injections of $1\times10^{10}$ particles per dose of CN733 (diamonds), CN739 (squares), CN790 (triangles), or vehicle alone (crosses).

HepG2 tumors. On days 1–5 and 8–12 after introducing the HepG2 cells into the mice, CN733, CN739, or CN790, at a concentration of 1x$10^{10}$ particles in a volume of 50 $\mu$l, or, as a control, vehicle alone, was injected into the mice intravenously. There were 10 mice per test group and in the vehicle-only control group. The results are shown in FIG. 13. On average, tumors treated with CN733 or CN790 four weeks after treatment were 857 $mm^3$ and 256 $mm^3$, respectively. Tumors treated with either CN739 or vehicle were 1521 $mm^3$ and 1601 $mm^3$, respectively. Even though both CN733 and CN790 were able to delay tumor progression, CN790 produced a greater tumor response. Both CN733- and CN790-treated tumors increased in size from four to six weeks after the start of treatment. As expected, CN739, a prostate-specific virus, had no effect on tumor growth. CN739-treated tumors, unlike CN733- and CN790-treated tumors, appeared well vascularized. In contrast, CN733- and CN790-treated tumors had a mottled appearance indicative of tumor necrosis.

Figure 34B:
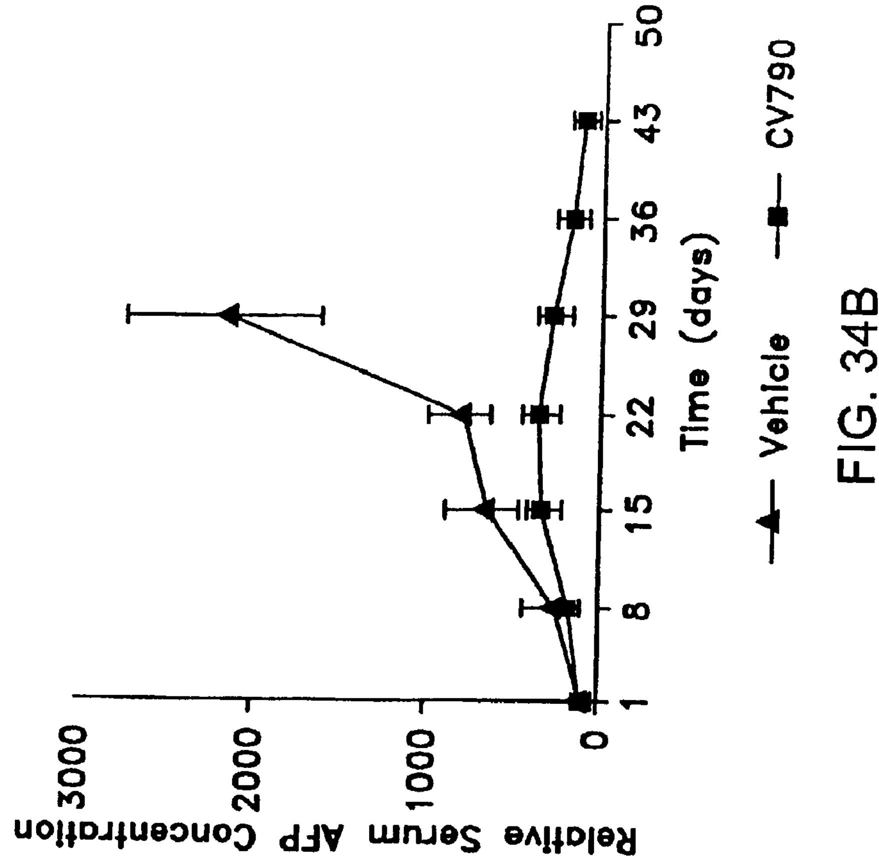
FIGS. 34A and 34B are bar graphs depicting the relative tumor volumes (FIG. 34A) and relative serum AFP concentrations (FIG. 34B) in nude mice bearing Hep3B tumor xenografts.
Figure 34A:
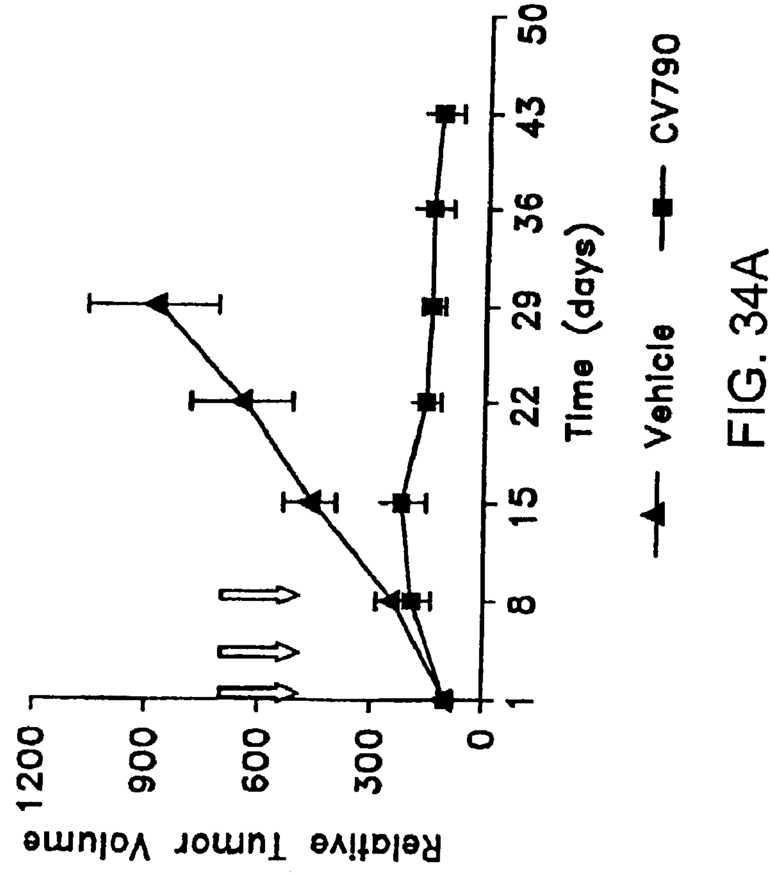

Hep3B tumors. Subcutaneous Hep3B xenografts in nude mice were treated with intravenously administered CN790. Mice were treated with either 4x$10^9$ PFU of CN790 (particle/PFU=20/1) or vehicle alone on days 1, 4, and 8 via tail vein injection. There were 7 mice per test group and 8 in the vehicle-only control group. Tumor size and the concentration of serum AFP were monitored weekly. Control buffer treated mice were sacrificed at four weeks due to excessive tumor burden. Average tumor volumes and serum AFP levels were normalized to 100% at day 1. The results are shown in FIG. 34A. The data demonstrate significant tumor killing from CN790. At day 29, the average relative tumor volume of CN790 treated mice was 142%, whereas vehicle treated was 899%. At day 43, one mouse was tumor-free and two others exhibited tumor regression out of seven total animals. Statistical analysis of the results was conducted using the unpaired, two-tailed t-test. The differences in mean relative tumor volumes between CN790 treated and buffer treated tumors are significant at days 15, 22 and 29 ($p<0.05$).

Serum AFP Levels in Mice Treated with CN790

Figure 14:
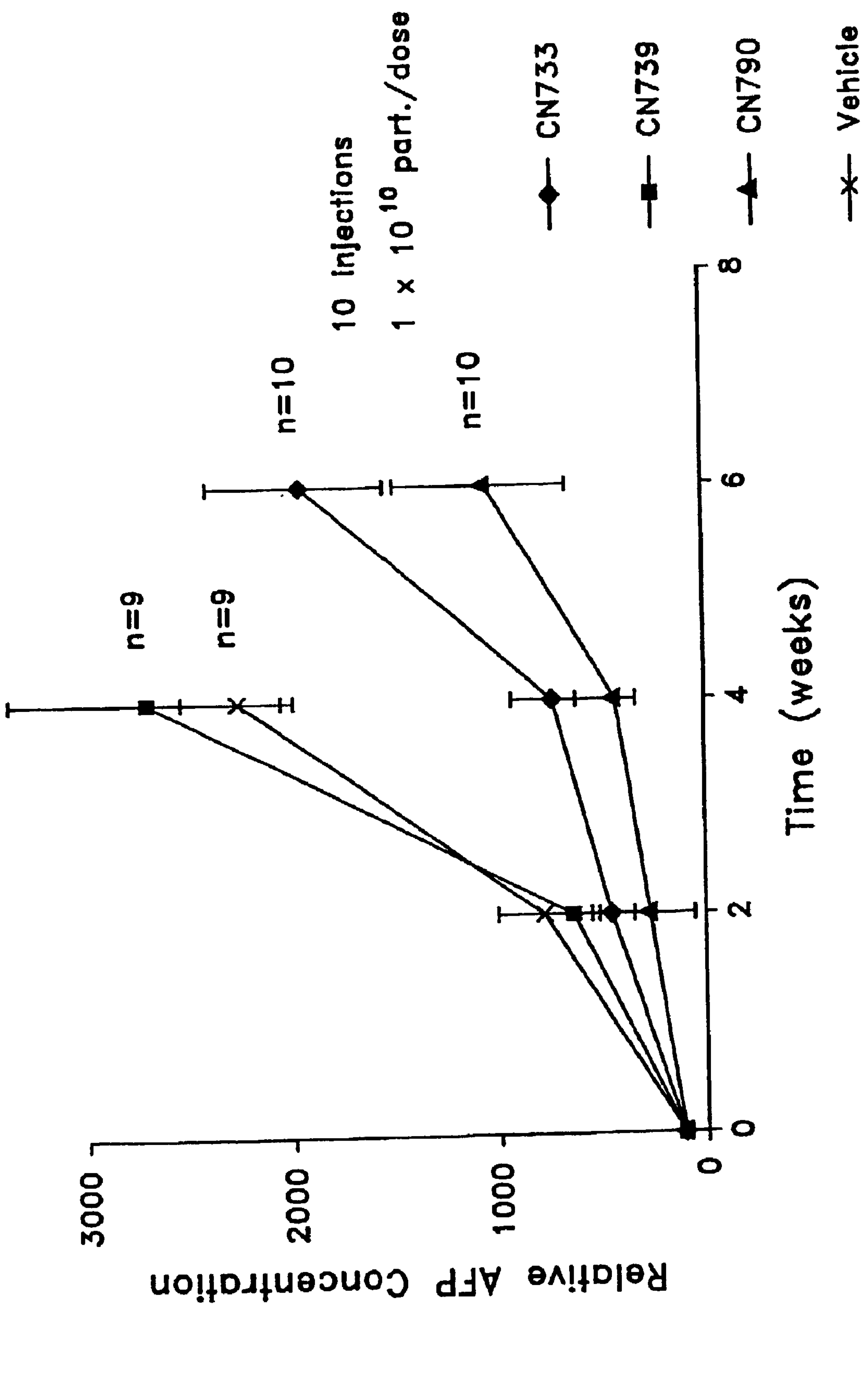
FIG. 14 is a graph depicting relative serum concentrations of AFP in mice with tumor xenografts, after treatment with 10 injections of $1\times10^{10}$ particles per dose of CN733 (diamonds), CN739 (squares), CN790 (triangles), or vehicle alone (crosses).
Figure 15:
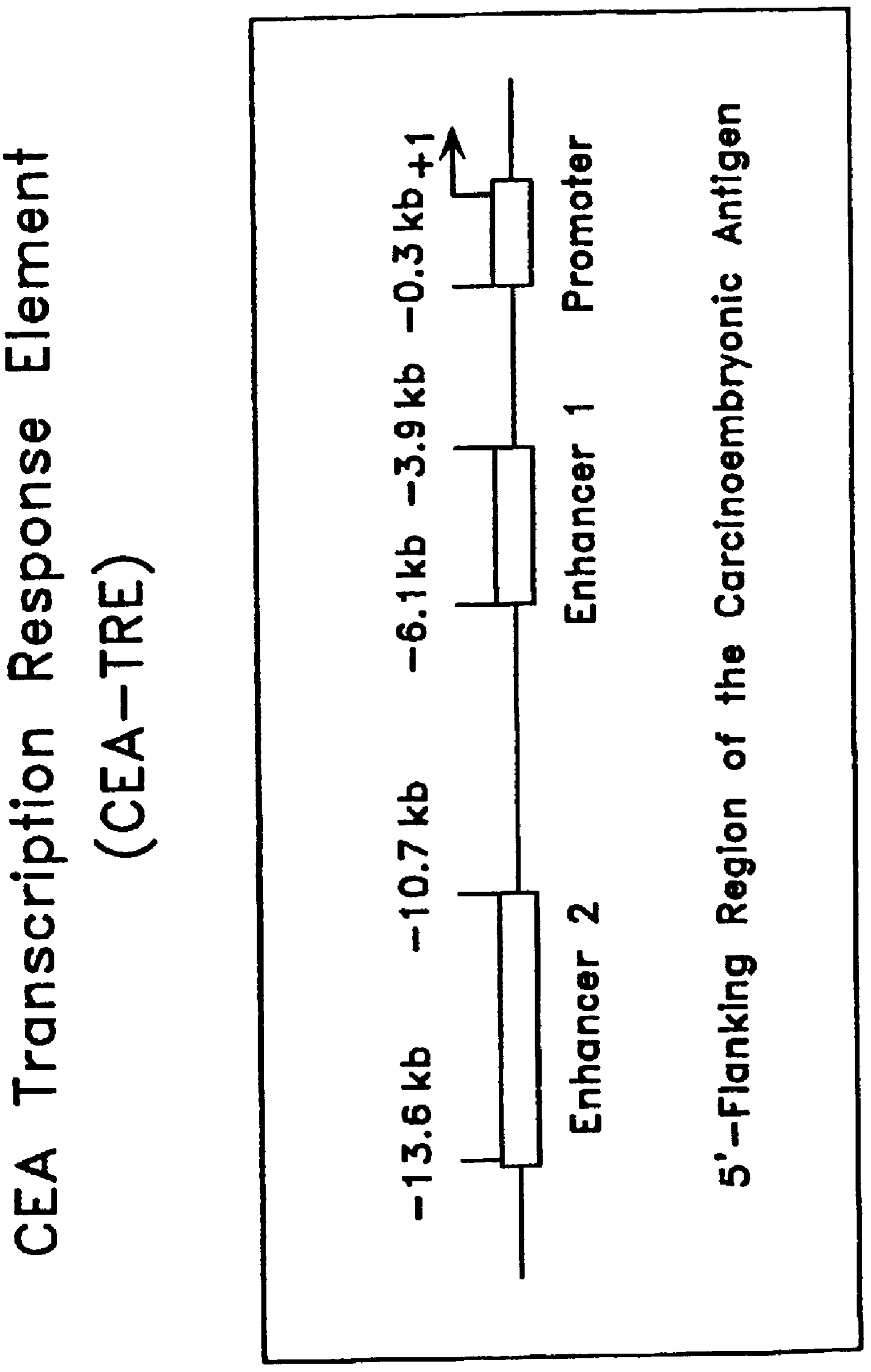
FIG. 15 is a schematic representation of the 5' flanking region of the carcinoembryonic antigen (CEA) gene.

Besides tumor volume, another measure of the efficacy of treatment of tumors is serum concentration of a tumor marker. Serum AFP levels were measured at various times after treatment with adenoviral vectors. The results are shown in FIG. 14. HepG2 mice (i.e., mice harboring a HepG2 xenograft) treated as described above with either CN733 or CN790 had average serum AFP concentrations of 214 $\mu$g/ml and 79 $\mu$g/ml, respectively, at four weeks after the start of treatment. In contrast, mice treated with either vehicle or CN739 had serum AFP concentrations of 443 $\mu$g/ml and 619 $\mu$g/ml, respectively. In general, CN733 and CN790 slowed the rise in serum AFP concentration compared to CN739 or buffer. The difference in mean AFP concentration between vehicle-treated and CN733-treated and between vehicle-treated and CN790-treated is significant beginning at week 4.

The levels of serum AFP in treated Hep3B mice provide additional evidence of CN790 antitumor activity. At day 29, CN790 treated mice had an average serum AFP concentration of 269%, and vehicle treated mice were 2161%. At day 43, the concentration in CN790 treated mice was 110%. Three mice had decreased serum AFP levels after dosing (FIG. 34B). Statistical analysis of the results was conducted using the unpaired, two-tailed t-test. The differences in mean serum AFP concentrations between CN790 treated and buffer treated tumors are significant at days 15, 22 and 29 ($p<0.05$).

In summary, intravenously administered CN790 is more effective at delaying the growth of HepG2 tumors and slowing the rise of serum AFP levels in a nude mouse model for primary liver cancer, when compared to $E3^-$ CN733. Furthermore, CN790 not only delayed the growth of Hep3B tumors but eradicated the tumor in one of the mice tested. The greater anti-tumor effective, $E3^+$, CN790 indicates that adenoviral vectors that contain an E3 region or portion of E3 are more cytotoxic than those that are deleted for E3. Cells infected with E3-containing virus also release more progeny virus and can be lysed sooner than cells infected with E3-deleted viruses.

Mechanism of Tumor Cytolysis by CN790

Immunohistochemistry

Hep3B tumors were established in nu/nu mice. Three mice treated with buffer and three mice treated with CN790 ($4\times10^9$ PFU/dose) on days 1, 4, and 8 were sacrificed on day 9. Tumors were fixed in 10% neutral buffered formalin, embedded in paraffin and sectioned using standard procedures. To detect adenovirus, tissue sections were blocked with normal rabbit serum (Biogenex, San Carlos, Calif.) for 20 min and incubated with goat anti-Ad antibody (Biodesign International, Kennebunkport, Me.) diluted 1:200 in PBS for 30 min. Alkaline phosphatase staining was performed using Super Sensitive streptaviden-biotin alkaline phosphatase reagents and Fast Red chromogen (Biogenex) as suggested by the manufacturer. Sections were counterstained with Gill's hematoxylin and mounted with Gel Mount (Biomedia, Foster City, Calif.) aqueous mounting media.

Apoptosis Assay

Apoptotic cells were detected using TdT labeling (ApopTag Peroxidase In Situ Apoptosis Detection Kit, Intergen, Purchase, N.Y.). Sections were pretreated with 20 μg/ml of protinase K for 15 min, counterstained with methyl green and mounted with Permount (Fisher). To evaluate the number of apoptotic cells in virus-treated and un-treated control tumors, the tumors were sectioned through their largest diameter and slices were prepared from each half of the resected tumor. The apoptotic index was estimated by the number of positive cells/100× field, eight sections per tumor. A minimum of five 100× fields were counted for each section. The mean of the sections was used for the apoptotic assay, and representative sections presented.

Figure 35:
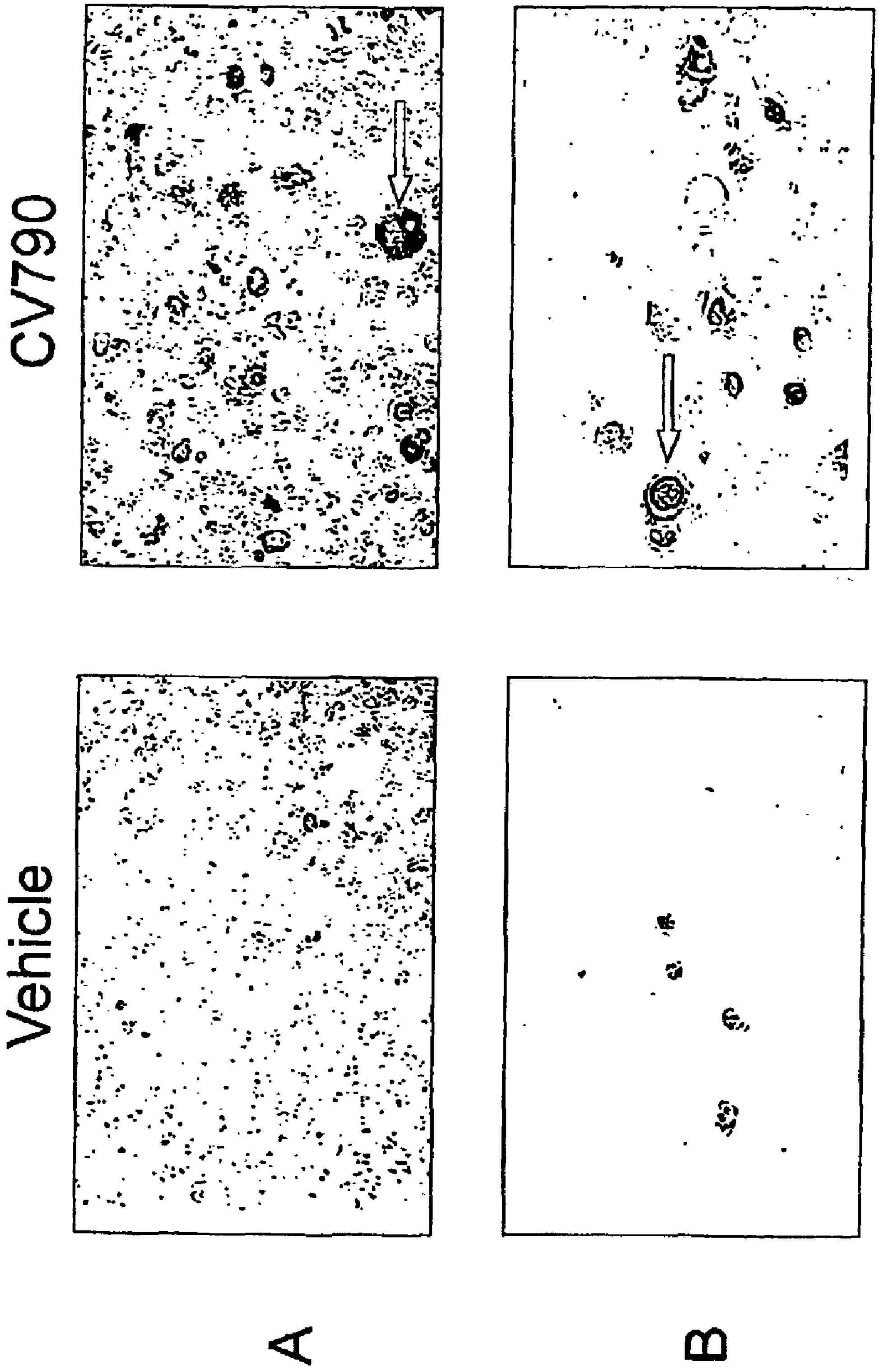
FIG. 35 is a half-tone reproduction of immunohistochemical analysis of Hep3B xenograft tumors in nude mice treated with CN790. Adenovirus infected cells were detected by polyclonal rabbit antibody to Ad5 hexon and indicated by a filled arrow (FIG. 35A). Apoptotic bodies were detected by TdT labeling and indicated by the filled arrow (FIG. 35B). Photos at 400×.

Results. To investigate mechanisms of CN790 tumor destruction, Ad5 hexon staining for virus replication and the apoptotic index by TdT labeling of treated tumors was determined. Virus replication in Hep3B tumors was confirmed by immunohistochemical staining of tumor sections using polyclonal antibodies to Ad5 hexon. Ad5 hexon is not found immediately or several days after intravenous virus administration. However, Ad5 hexon can be detected by immunohistochemistry late in the virus replication cycle. FIG. 35A shows Hep3B xenograft tumors stained for Ad5 hexon 9 days following treatment intravenously with CN790. While positively stained cells were visible throughout the tumor, infected cells were predominantly located near the tumor periphery. No adenovirus was detected in vehicle treated tumors.

To estimate CN790 induced apoptosis, three CN790 treated and three control tumors were analyzed nine days after initial dosing (FIG. 35B). Treated tumors had a 70% higher apoptotic index than control tumors. Because apoptosis is short-lived, even modest increases in the apoptotic index of a tumor may result in a significant antitumor effect. Bursch et al. (1992) *Trends Pharmacological Science* 13:245–251; and Bursch et al. (1990) *Carcinogenesis* 11:847–853. Apoptotic bodies were observed both adjacent to infected cells and uninfected areas, indicating that apoptosis may augment virus mediated killing. Thus, the immunohistochemical analysis of CN790 treated tumors suggests that both virus replication-dependent cytolysis and apoptosis contribute to the CN790 antitumor effect.

Figure 31:
FIG. 31 is a half-tone reproduction of plaques formed by CN733 and CN790 on 293 cells.

Furthermore, CN790 caused plaques that were estimated to be 5 times larger than those lysed by CN733 on 293 cells 6 days after infection (FIG. 31), indicating that CN790 possesses higher potency to induce apoptosis than CN733.

In summary, CN790 grows at least 100,000 fold less efficiently than the wild-type E1 viruses CN702 and CN802 in $AFP^-$ cells (OVCAR-3 cells). Most importantly, intravenous administration of CN790 inhibited the growth of HCC xenografts and stabilized the concentration of serum tumor marker AFP to a greater extent than CN733. Immunohistochemical analysis of treated tumors confirmed that systemically administered CN790 productively infected the tumor mass and caused tumor killing. Furthermore, our analysis revealed that treated tumors had a higher apoptotic index than control tumors, suggesting that virus replication-dependent cytolysis and apoptosis were mechanisms of tumor destruction.

Example 4

Figure 17:
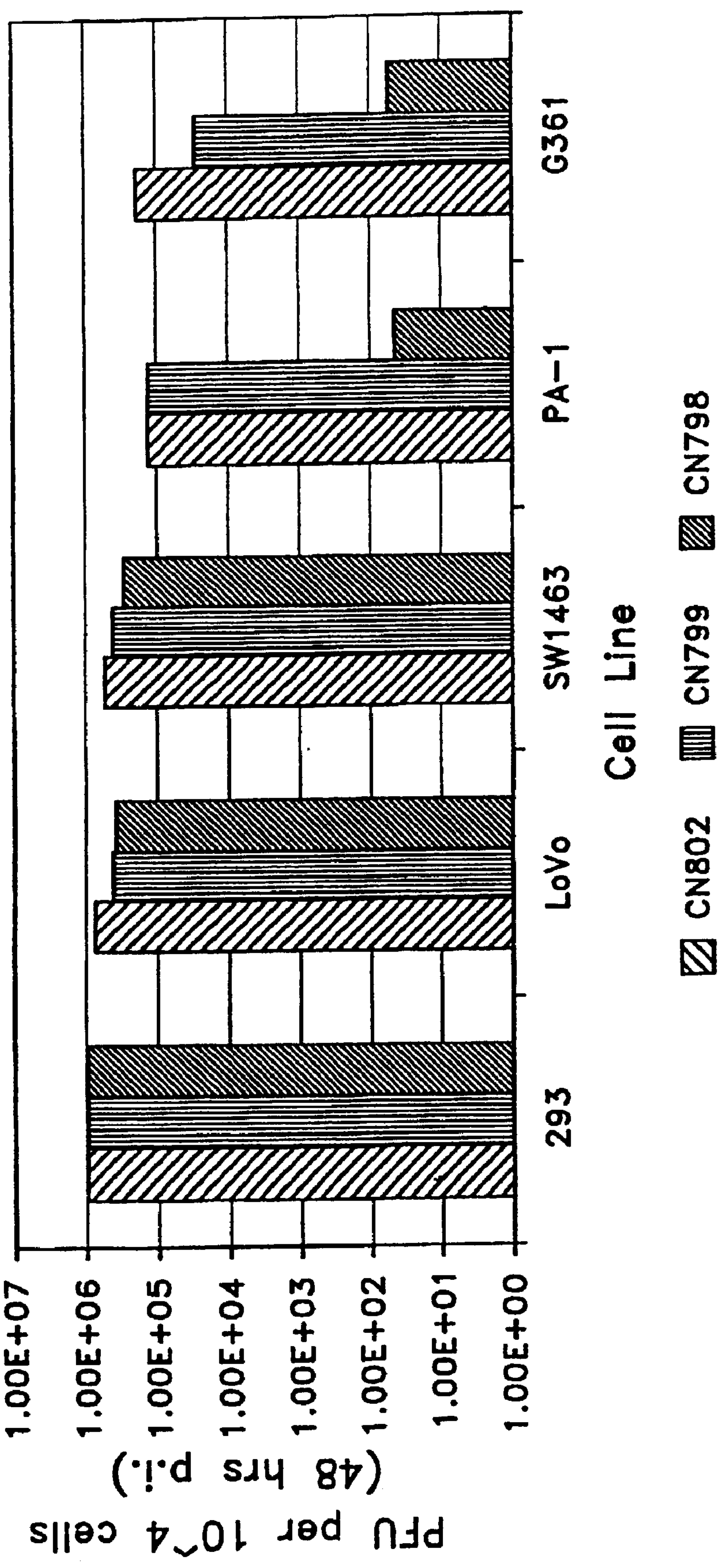
FIG. 17 is a bar graph depicting the number of plaque-forming units 48 hours after infection of various cell lines with CN802 (left bars), CN799 (middle bars), or CN798 (right bars).

In vitro Characterization of E3-containing Adenoviral Constructs Comprising a CEA-TRE Driving Expression of E1A To examine the cell-type specificity of CN802, CN799, and CN798, various cell lines were infected at a concentration of 2 PFU per cell with the constructs. The number of plaque-forming units was determined 48 hours post-infection, as described above. As shown in FIG. 17, CN798, which contains an E3 region, plaqued efficiently on LoVo, and SW1463 cells, which synthesize CEA, but inefficiently on PA-1 and G361 cells, which do not. In contrast, CN799 and CN802 plaqued efficiently on all cell lines tested. Thus, CN798 appears to specific for CEA-expressing cell lines.

Figure 18:
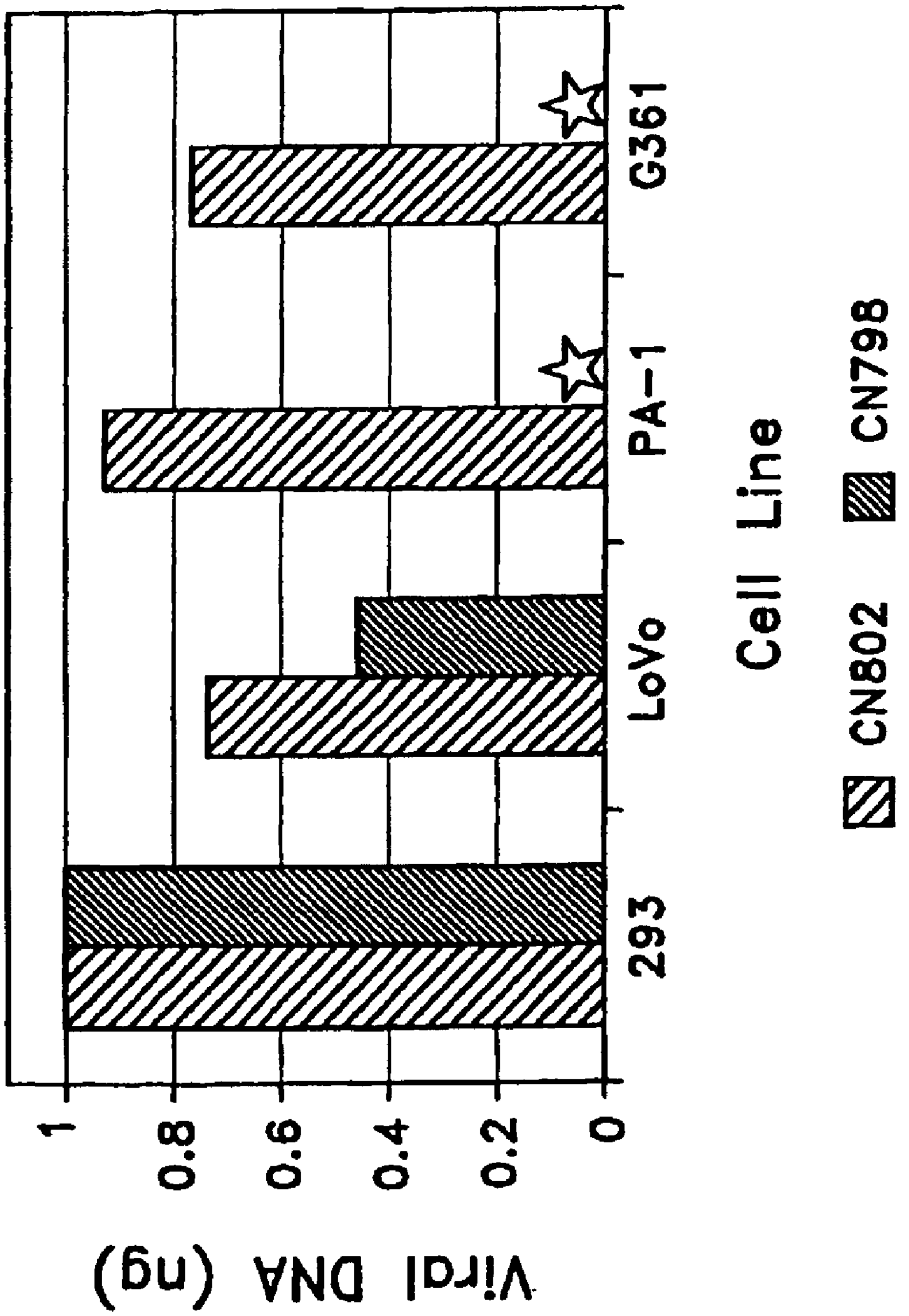
FIG. 18 is a bar graph depicting the relative viral DNA yield obtained when various cell lines were infected with CN802 (stippled bars) or CN798 (solid bars). Stars indicate no detectable virus.

As another measure of cell specificity, LoVo, PA-1, and G361 cells were infected with CN802 or CN798, and viral DNA was measured. Equal amounts of cellular DNA were added to wells and quantitated by a slot blot assay. As shown in FIG. 18, viral DNA was undetectable in PA-1 or G361 cells infected with CN798, while approximately 0.4 ng CN798 DNA was measured in infected LoVo cells. In contrast, CN802 viral DNA was detected in all four cell lines infected with this construct.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

What is claimed is:

1. A replication competent adenovirus vector for selective cytolysis of a target cell, comprising (a) an intact E3 region; (b) an adenovirus early gene essential for adenovirus replication under transcriptional control of a first tumor cell-specific transcriptional response element (TRE); and (c) a transgene.

2. The adenovirus vector according to claim 1, wherein said adenovirus early gene essential for adenovirus replication is E1A, E1B or E4.

3. The adenovirus vector according to claim 1, wherein said transgene is under transcriptional control of a second tumor cell-specific transcriptional response element (TRE).

4. The adenovirus vector according to claim 3, wherein said first and second tumor cell-specific TREs are functional in the same cell.

5. The adenovirus vector according to claim 1, wherein the transgene is a cytotoxic gene.

6. The adenovirus vector according to claim 5, wherein said cytotoxic gene is the Herpes Simplex Virus thymidine kinase (HSV-TK) gene or the cytosine deaminase (cd) gene.

7. The adenovirus vector according to claim 6, wherein said cytotoxic gene is HSV-TK.

8. The adenovirus vector according to claim 1, wherein the transgene is a cytokine gene selected from the group consisting of Interleukin (IL)-1, IL-2, IL-6, IL-12 and GM-CSF.

9. The adenovirus vector according to claim 8, wherein said cytokine gene is GM-CSF.

10. The adenovirus vector according to claim 1, wherein the transgene encodes a factor capable of initiating apoptosis.

11. An adenovirus vector comprising (a) an intact E3 region; (b) an adenovirus gene essential for adenovirus replication under transcriptional control of a first tumor cell-specific transcriptional response element (TRE); and (c) an adenovirus death protein gene (ADP).

12. An adenovirus vector comprising (a) at least one intact open reading frame from the adenovirus E3 region selected from the group consisting of gp19k protein, 14.7k protein and 10.4k/14.5k protein complex; (b) an adenovirus gene essential for adenovirus replication under transcriptional control of a first tumor cell-specific transcriptional response element (TRE); and (c) a transgene.

13. The adenovirus vector according to claim 12, wherein said transgene is under transcriptional control of a second tumor cell-specific transcriptional response element (TRE).

14. The adenovirus vector according to claim 13, wherein said first and second tumor cell-specific TREs are functional in the same cell.

15. The adenovirus vector according to claim 12, wherein the transgene is a GM-CSF.

16. The adenovirus vector according to claim 12, wherein the transgene is a HSV-TK.

17. An isolated host cell comprising the adenovirus vector of claim 1.

18. An isolated host cell comprising the adenovirus vector of claim 12.

19. A pharmaceutical composition comprising the adenovirus vector of claim 1 and a pharmaceutically acceptable excipient.

* * * * *